(12) United States Patent
Yorke-Smith et al.

(10) Patent No.: US 7,871,979 B2
(45) Date of Patent: Jan. 18, 2011

(54) CSF3R POLYPEPTIDES AND USES THEREOF

(75) Inventors: Melanie Yorke-Smith, Bernex (CH); Andreas Pigni, Carouge (CH)

(73) Assignee: Merck Serono SA, Coinsins, Vaud (CH)

( * ) Notice: Subject to any disclaimer, the term of this patent is extended or adjusted under 35 U.S.C. 154(b) by 0 days.

(21) Appl. No.: 12/304,427

(22) PCT Filed: Jul. 5, 2007

(86) PCT No.: PCT/EP2007/056846

§ 371 (c)(1), (2), (4) Date: Dec. 11, 2008

(87) PCT Pub. No.: WO2008/003763

PCT Pub. Date: Jan. 10, 2008

(65) Prior Publication Data

US 2010/0004167 A1 Jan. 7, 2010

Related U.S. Application Data

(60) Provisional application No. 60/832,177, filed on Jul. 19, 2006.

(30) Foreign Application Priority Data

Jul. 6, 2006 (EP) .................................. 06116704

(51) Int. Cl.
*A61K 38/00* (2006.01)
*C07K 14/00* (2006.01)

(52) U.S. Cl. ........................................ 514/7.6; 530/350

(58) Field of Classification Search ....................... None
See application file for complete search history.

(56) References Cited

PUBLICATIONS

Ku et al., 1996, Blood, vol. 88, pp. 4124-4131 (see abstract).*
Fukunaga, R. et al. "Three different mRNAs encoding human granulocyte colony-stimulating factor receptor", *Proc. Natl. Acad. Sci. USA*, Nov. 1990, pp. 8702-8706, vol. 87, XP-002398193.
Seto, Y. et al. "Chromosomal Gene Organization of the Human Granulocyte Colony-Stimulating Factor Receptor", *Journal of Immunology*, Jan. 1, 1992, pp. 259-266, vol. 148, No. 1, XP-002398198.
Hiraoka, O. et al. "Requirement for the Immunoglobulin-like Domain of Granulocyte Colony-stimulating Factor Receptor in Formation of a 2:1 Receptor-Ligand Complex", *Journal of Biological Chemistry*, Oct. 27, 1995, pp. 25928-25934, vol. 270, No. 43, XP-002398196.
Barreda, D.R. et al. "Regulation of myeloid development and function by colony stimulating factors", *Development and Comparative Immunology*, 2004, pp. 509-554, vol. 28, XP-002398199.
Rutella, S. et al. "Granulocyte Colony-Stimulating Factor: A Novel Mediator of T Cell Tolerance", *Journal of Immunology*, 2005, pp. 7085-7091, vol. 175.
Iwasaki, H. et al. "Production of Soluble Granuloctye Colony-Stimulating Factor Receptors from Myelomonocytic Cells", *Journal of Immunology*, 1999, pp. 6907-6911, vol. 163.
Asano, Y. et al. "Effect of the Chimeric Soluble Granulocyte Colony-Stimulating Factor Receptor on the Proliferation of Leukemic Blast Cells from Patients with Acute Myeloblastic Leukemia", *Cancer Res.*, Aug. 15, 1997, pp. 3395-3397, vol. 57, No. 16.
Druhan, L. J. et al. "Novel Mechanism of G-CSF Refractoriness in Patients with Severe Congenital Neutropenia", *Blood*, 2005, pp. 584-591, vol. 105.
Database EMBL, Accession No. DB321299, "*Homo sapiens* cDNA clone LIVER2004777, 3' end, mRNA sequence", Oct. 25, 2003, XP-002398203, p. 1.
Database EMBL, Accession No. AY148100, "*Homo sapiens* colony stimulating factor 3 receptor (granulocyte) (CSF3R) gene, complete CDS", Sep. 18, 2002, XP-002398204, pp. 1-14.
Layton, J. E. et al. "Identification of Ligand-binding Site III on the Immunoglobulin-like Domain of the Granulocyte Colony-stimulating Factor Receptor", *Journal of Biological Chemistry*, Sep. 28, 2001, pp. 36779-36787, vol. 276, No. 39.

* cited by examiner

*Primary Examiner*—Robert Landsman
*Assistant Examiner*—Ian Dang
(74) *Attorney, Agent, or Firm*—Saliwanchik, Lloyd & Saliwanchik

(57) ABSTRACT

The present invention relates to CSF3R polypeptide variants and their uses, particularly for therapeutic or prophylactic treatment in human subjects. The invention also relates to nucleic acids encoding said polypeptides, vectors comprising such nucleic acids and recombinant cells containing the same. The invention further discloses methods of producing such polypeptides, as well as methods and tools for detecting or dosing these polypeptides in any sample.

12 Claims, 3 Drawing Sheets

Figure 1

```
                                        sCSF3R-F1
                                  ─────────────────────────▶         ─▶
  1   GTGAACATCA AGTTGGTGCT ATGGCAAGGC TGGGAAACTG CAGCCTGACT
               sCSF3R-F1 nest         M  A  R    L  G  N    C  S  L  T
       ──────────────────────────▶
 51   TGGGCTGCCC TGATCATCCT GCTGCTCCCC GGAAGTCTGG AGGAGTGCGG
       W  A  A    L  I  I    L  L  L  P  G  S  L    E  E  C 101   GCACATCAGT GTCTCAGCCC CCATCGTCCA CCTGGGGGAT CCCATCACAG
       G  H  I  S  V  S  A    P  I  V    H  L  G    D  P  I  T 151   CCTCCTGCAT CATCAAGCAG AACTGCAGCC ATCTGGACCC GGAGCCACAG
       A  S  C    I  I  K  Q    N  C  S    H  L  D    P  E  P  Q 201   ATTCTGTGGA GACTGGGAGC AGAGCTTCAG CCCGGGGGCA GGCAGCAGCG
       I  L  W    R  L  G    A  E  L  Q    P  G  G    R  Q  Q 251   TCTGTCTGAT GGGACCCAGG AATCTATCAT CACCCTGCCC CACCTCAACC
       R  L  S  D  G  T  Q    E  S  I    I  T  L  P    H  L  N 301   ACACTCAGGC CTTTCTCTCC TGCTGCCTGA ACTGGGGCAA CAGCCTGCAG
       H  T  Q    A  F  L  S    C  C  L    N  W  G    N  S  L  Q 351   ATCCTGGACC AGGTTGAGCT GCGCGCAGGC TGTAAGTCCT TCCAGCCATC
       I  L  D    Q  V  E    L  R  A  G    C  K  S    F  Q  P 401   CAACTACTCT GCCTCCAACA CCCTCCTGCC AATACTAATA AGAATATTAC
       S  N  Y  S  A  S  N    T  L  L    P  I  L  I    R  I  L 451   CAGCCGGGCA CGTTGGCTCA CGCCTGTATT CCCAGCACTT TGGGAGGCCG
       P  A  G    H  V  G  S    R  L  Y    S  Q  H    F  G  R  P
                                                         sCSF3R-R1 nest
                                        ◀────────────────────────────
501   AGGCAGGCGG ATCACCTGAG GTCAGGAGTT CATGATCAGC CTGGCCAGCA
       R  Q  A    D  H  L    R  S  G  V    H  D  Q    P  G  Q
               sCSF3R-R1
       ◀───────────────────
551   AGGCGAAACC CCGCCTCTAC TAAAAATACA AAAAAATTAG CCAGGCATA
       Q  G  E  T  P  P  L    L  K  I    Q  K  N
```

───▶    Position and sense of PCR primers.

Figure 2

```
  1  ACTTGGGCTG CCCTGATCAT CCTGCTGCTC CCCGGAAGTC TGGAGGAGTG
      T  W  A    A  L  I    I  L  L    P  G  S    L  E  E

51  CGGGCACATC AGTGTCTCAG CCCCCATCGT CCACCTGGGG GATCCCATCA
      C  G  H    I  S  V  S  A  P  I    V  H  L  G  D  P  I

101  CAGCCTCCTG CATCATCAAG CAGAACTGCA GCCATCTGGA CCCGGAGCCA
      T  A  S    C  I  I  K   Q  N  C    S  H  L    D  P  E  P

151  CAGATTCTGT GGAGACTGGG AGCAGAGCTT CAGCCCGGGG GCAGGCAGCA
      Q  I  L    W  R  L    G  A  E  L    Q  P  G    G  R  Q

201  GCGTCTGTCT GATGGGACCC AGGAATCTAT CATCACCCTG CCCCACCTCA
      Q  R  L  S    D  G  T    Q  E  S    I  I  T  L    P  H  L

251  ACCACACTCA GGCCTTTCTC TCCTGCTGCC TGAACTGGGG CAACAGCCTG
      N  H  T    Q  A  F  L    S  C  C    L  N  W    G  N  S  L

301  CAGATCCTGG ACCAGGTTGA GCTGCGCGCA GGCTGTAAGT CCTTCCAGCC
      Q  I  L    D  Q  V    E  L  R  A    G  C  K    S  F  Q

351  ATCCAACTAC TCTGCCTCCA ACACCCTCCT GCCAATACTA ATAAGAATAT
      P  S  N  Y    S  A  S    N  T  L    L  P  I  L    I  R  I

401  TACCAGCCGG GCACGTTGGC TCACGCCTGT ATTCCCAGCA CTTTGGGAGG
      L  P  A    G  H  V  G    S  R  L    Y  S  Q    H  F  G  R

451  CCGAGGCAGG CGGATCACCT GAGGTCAGGA GTTCATGATC AGCCTGGCCA
      P  R  Q    A  D  H    L  R  S  G    V  H  D    Q  P  G
```

Figure 3

|  | Signal peptide | Ig-like C2-type domain |
|---|---|---|

```
GCSR_HUMAN    MARLGNCSLTWAALIILLLPGSLE ECGHISVSAPIVHLGDPITASCIIKQNCSHLDPEPQ
Full_sCSF3R   MARLGNCSLTWAALIILLLPGSLE ECGHISVSAPIVHLGDPITASCIIKQNCSHLDPEPQ
              ************************ ***********************************

GCSR_HUMAN    ILWRLGAELQPGGRQQRLSDGTQESIITLPHLNHTQAFLSCCLNWGNSLQILDQVELRAG
Full_sCSF3R   ILWRLGAELQPGGRQQRLSDGTQESIITLPHLNHTQAFLSCCLNWGNSLQILDQVELRAG
              ************************************************************
```

Fibronectin III (1)
```
GCSR_HUMAN    YPPAIPHNLSCLMNLTTSSLICQWEPGPETHLPTSFTLKSFKSRGNCQTQGDSILDCVPK
Full_sCSF3R   CKSFQPSNYSASNTLLPILIRILPAGHVGSRLYSQHFCRFRQADHLRSGVEDQPGQQGET GCSR_HUMAN    DGQSHCCIPRKHLLLYQNMGIWVQAENALGTSMSPQLCLDPMDVVKI FPPMLRTMDFSPE
Full_sCSF3R   PPLLKIQKN-------------------------------------
```

Fibronectin III (2)
```
GCSR_HUMAN    AAPPQAGCLQLCWEPWQPGLHINQKCELRHKPQRGEASWALVGPLPLEALQYELCGLLPA

GCSR_HUMAN    TAYTLQIRCIRWPLPGHWSDWSPSLELRTTERAPTVRLDTWWRQRQLDPRTVQLFWKPVP
```

Fibronectin III (3)
```
GCSR_HUMAN    LEEDSGRIQGYVVSWRPSGQAGAILPLCNTIELSCTFHLPSEAQEVALVAYNSAGTSRPT
```

Fibronectin type-III (4).
```
GCSR_HUMAN    PVVFSESRGPALTRLHAMARDPESLWVGWEPPNPWPQGYVIEWCLGPPSASNSNKTWRME

GCSR_HUMAN    QNGRATGFLLKENIRPFQLYEIIVTPLYQDTMGPSQHVYAYSQFMAPSHAPELHLKHIGK
```

Fibronectin type-III (5).
```
GCSR_HUMAN    TWAQLEWVPFPPELGKSFLTHYTIFWTNAQKQSFSAILNASSRGFVLRQLFPASLYHIEL

GCSR_HUMAN    MAASQAGATNSTVLTLMTLTPEGSELHIILGLFGLLLLLLTCLCGTAWLCCSPNRKNFLWP
```

Box 1 motif
```
GCSR_HUMAN    SVPDPAHSSLGSWVPTIMEEDAFQLPGLGTPPITKLTVLEEDEKKPVPWESHNSSETCGL

GCSR_HUMAN    PTLVQTYVLQGDPRAVSTQPQSQSGTSDQVLYGQLLGSPTSPGPGHYLRCDSTQPLLAGL
```

CSF3R POLYPEPTIDES AND USES THEREOF

CROSS-REFERENCE TO RELATED APPLICATION

This application is the U.S. national stage application of International Patent Application No. PCT/EP2007/056846, filed Jul. 5, 2007, which claims the benefit of U.S. Provisional Patent Application No. 60/832,177, filed Jul. 19, 2006, the disclosures of which are hereby incorporated by reference in their entireties, including all figures, tables and amino acid or nucleic acid sequences.

The present invention relates to CSF3R polypeptides and their uses, particularly for therapeutic or prophylactic treatment in human subjects. The invention also relates to nucleic acids encoding said polypeptides, vectors comprising such nucleic acids and recombinant cells containing the same, as well as corresponding pharmaceutical compositions. The invention further discloses methods of producing such polypeptides, as well as methods and tools for detecting or dosing these polypeptides in any sample.

BACKGROUND

Granulocyte colony stimulating factor (GCSF or CSF3) exerts its function via the activation of a membrane receptor, the colony stimulating factor 3 receptor (CSF3R), that belongs to the super-family of hematopoietin receptors, also being referred to as class I cytokine receptors. CSF3R is also known as the granulocyte colony stimulating factor receptor (GCSFR) or CD7 114.

A number of receptors for lymphokines, hematopoietic growth factors, and growth hormone-related molecules have been found to share a common binding domain. These receptors are referred to as hematopoietin receptors and the corresponding ligands as hematopoietins. Further, hematopoietins have been subdivided into two major structural groups: Large/long and small/short hematopoietins. One subset of individual receptor chains that are part of receptor complexes for large hematopoietins contain common structural elements in their extracellular parts: an immunoglobin-like domain, a hematopoietin-receptor domain, and 3 fibronectin type-III domains (2 in the leptin receptor). This subgroup was designated the "gp130 family of receptors" (Mosley, et al. J. Biol. Chem. 1996, 271, 32635-43) and include Leptin receptor (LPTR), Granulocyte colony stimulating factor receptor (GCSFR), Interleukin-6/-11/LIF/OSM/CNTF common beta chain (GP130), Leukemia inhibiting factor receptor (LIFR), Oncostatin-M receptor beta chain (OSMR), interleukin-12 receptor beta-1 chain (IL12RB1), Interleukin-12 receptor beta-2 chain (IL12RB2). These receptor chains homodimerize (GCSFR, GP130, LPTR) or heterodimerize (GP130 with LIFR or OSMR, IL12RB1 with IL12RB2) upon binding the cognate cytokine.

The human CSF3R protein is a 826 amino acid polypeptide comprising a signal peptide (amino acid residues 1-24), an extracellular domain, located within the N-terminal region of the protein (amino acid residues 25-627), an intracellular domain (amino acid residues 651-836) and a transmembrane region (amino acid residues 628-650). The extracellular portion contains an N-terminal immunoglobulin (Ig)-like domain (amino acid residues 25 to 117), a cytokine receptor homology (CRH) domain (amino acid residues 122 to 330), and 3 fibronectin type III (FNIII) domains. Within the CRH region are 2 FNIII domains, 4 conserved cysteine residues, and a conserved WSXWS motif (amino acid residues 318 to 322) that stabilizes the CRH domain. The Ig-like and CRH domains appear to be critical for high-affinity binding. A box 1 motif is present in the intracellular domain (amino acid residues 658 to 666) required for JAK interaction and/or activation.

GCSF stimulates proliferation, survival, and maturation of cells committed to the neutrophilic granulocyte lineage through binding to the specific GCSF receptor (see Hartung T., et al., Curr. Opin. Hematol. 1998; 5: 221-5). The CSF3R receptor possesses no intrinsic kinase activity in the cytoplasmic domain and uses receptor-associated intracellular protein kinases such as the Janus tyrosine kinases (JAKs) to initiate signal transduction. Stimulation of cells with G-CSF has been shown to activate multiple signal transduction pathways, including Signal Transducer and Activators of Transcription (STATs), Ras/Raf/Erk, phosphatidylinositol 3-kinase (PI3-K)/Akt, but also Stat proteases such as the Stat5 protease. Deregulated Stat5 activation may lead to aberrant cellular responses to CSF3 and contribute to leukemogenesis.

GCSF is typically used for the treatment of different kinds of neutropenia in humans. It is one of the few growth factors approved for clinical use. In particular, it is used to reduce chemotherapy (CT)-induced cytopenia (Viens et al., J. of Clin. Oncology, Vol. 20, No. 1, 2002: 24-36). GCSF has also been implicated for therapeutic use in infectious diseases as potential adjunctive agent (Hubel et al., J. of Infectious Diseases, Vol. 185: 1490-501, 2002).

In a mouse model of myocardial infarction, CSF3 treatment did not affect initial infarct size at day 3 but improved cardiac function as early as 1 week postinfarction, and the beneficial effects were reduced by delayed start of treatment (Harada et al. Nature Med. Vol. 11: 305-311, 2005). CSF3 induced antiapoptotic proteins and inhibited apoptotic death of cardiomyocytes, and CSF3 also reduced apoptosis of endothelial cells and increased vascularization in the infarcted hearts. Harada et al. suggested that CSF3 promotes survival of cardiac myocytes and prevents left ventricular remodeling after myocardial infarction.

Application of a single dose of G-CSF in patients with community-acquired pneumonia (CAP) caused a prolonged survival and increased activation of neutrophils combined with a sustained release of anti-inflammatory cytokines (Droemann et al. Respiration. 2005 Dec. 12. Epub ahead of print).

CSF3 is also beneficial for the prevention and/or treatment of immune-mediated diseases, e.g. graft-vs-host disease, multiple sclerosis, systemic lupus erythematosus, inflammatory bowel disease, and diabetes (Rutella et al. J. Immunol. 2005 Dec. 1; 175(11):7085-91).

SUMMARY OF THE PRESENT INVENTION

The present invention discloses novel CSF3R polypeptide variants and their uses, particularly for therapeutic or prophylactic treatment in human subjects. The invention also discloses nucleic acids encoding said polypeptides, vectors comprising such nucleic acids, in particular, expression vectors, and recombinant cells containing the same, as well as corresponding pharmaceutical compositions. The invention further discloses methods of producing such polypeptides and methods and tools for detecting or dosing these polypeptides in any sample. Further included are antibodies specific for the novel CSF3R polypeptide variants of the present invention.

More particularly, the invention results from the identification, isolation and characterization of a naturally-occurring, novel soluble splicing variant of human CSF3R, named sCSF3R, having particular structural and biological properties, which represents a valuable pharmaceutical product.

An object of this invention thus resides in isolated CSF3R polypeptide variants, or a distinctive fragment thereof. The polypeptide variants of this invention comprise the sequence of a CSF3 ligand-binding domain and lack a functional trans-membrane domain. CSF3R polypeptides of this invention represent soluble forms of CSF3R, which may be used as agonists or antagonists thereof in various pathological conditions.

Another object of this invention resides in the mature form of CSF3R as defined above.

Another object of this invention resides in a fusion protein comprising a CSF3R polypeptide variant as defined above.

Another object of this invention resides in a conjugate comprising a CSF3R polypeptide variant as defined above.

Another object of this invention resides in a receptor complex comprising a CSF3R polypeptide variant as defined above.

A further object of this invention resides in a nucleic acid encoding a CSF3R polypeptide variant or a fusion protein as defined above, as well as any cloning or expression vector comprising such a nucleic acid.

The invention also relates to recombinant host cells comprising a vector or nucleic acid as defined above, as well as to methods of producing a CSF3R polypeptide variant as defined above using such recombinant cells.

A further aspect of this invention resides in a pharmaceutical composition comprising a product (e.g., a polypeptide, fusion protein, conjugate, receptor complex, nucleic acid, vector or recombinant cell) as defined above.

A further aspect of this invention resides in the use of a product (e.g., a polypeptide, fusion protein, conjugate, receptor complex, nucleic acid, vector or recombinant cell) as defined above, for the manufacture of a pharmaceutical composition for use in a human subject.

A further object of this invention also relates to an antibody, or a fragment or derivative of such an antibody that selectively binds a polypeptide as defined above.

The above products and pharmaceutical composition are particularly suited, for instance, for treating graft-vs-host disease, cancer, neutropenia, neurological disorders or conditions, pneumonia, autoimmune diseases, haematological diseases, hemopoietic disorders, infectious diseases, inflammatory bowel disease, and diabetes.

A further aspect of this invention resides in a method of detecting or dosing a polypeptide as defined above in a sample, e.g., using an antibody, fragment or derivative thereof as defined above.

Other aspects of this invention include primers and probes specific for a nucleic acid as defined above, as well as their uses to detect or diagnose the presence of such a nucleic acid in a sample.

LEGEND TO THE FIGURES

FIG. 1: sCSF3R DNA and protein sequence (SEQ ID NO:31). The position of PCR primers used for cloning is indicated by arrows.

FIG. 2: Nucleotide sequence with translation (SEQ ID NO:32) of the sCSF3R PCR product FIG. 3: Alignment between sCSF3R (SEQ ID NO:10) and the membrane bound protein (SEQ ID NO:2). The membrane bound protein contains a signal peptide (boxed) from amino acids 1 to 24, an Ig-like C2 type domain (underline) and 5 fibronectin III domains (double underline). The variant contains the signal peptide, the Ig-like domain and does not present any fibronectin III domain. The box 1 motif is required for jak interaction and/or activation. The Predicted molecular weight of sCSF3R is 20667.7761.

DETAILED DESCRIPTION OF THE INVENTION

The present invention results from the identification and characterization of novel biologically active human CSF3R polypeptide variants. These polypeptides typically comprise the sequence of a mature human CSF3R polypeptide that lacks a functional trans-membrane domain. In particular, the present invention resides in the identification of a naturally-occurring splice variant of CSF3R, named sCFS3R (SEQ ID NO:2). Further included are distinctive fragments which retain at least part of the biological activity of CSF3R polypeptide variants of the present invention. The present invention may be naturally occurring or synthetic CSF3R polypeptide variants and represent valuable therapeutic molecules. Furthermore, due to the absence of a functional trans-membrane domain, CSF3R polypeptide variants of this invention are not anchored into a cell membrane, and may circulate within biological fluids, particularly blood, plasma, serum, lymph or the like.

The extracellular region of membrane bound CSF3R (Swissprot accession Q99062; SEQ ID NO:10) comprises six structural domains: an N-terminal Immunoglobulin (Ig)-like domain followed by five fibronectin type III (FNIII) domains. The first two of the FNIII domains (called D2 and D3) form the cytokine receptor homology (CRH) module, which contains four cysteine residues in D2 and a WSXWS motif in D3. These features of the CRH module are conserved in members of the class 1 cytokine receptor family. Membrane bound CSF3R is composed of 15 coding exons. There are 2 non-coding exons in the 5' UTR. The start codon is in exon 3 and the stop codon in exon 15.

The soluble CSF3R variant of the present invention (SEQ ID NO:2) is encoded by exon 3, exon 4 and the genomic prolongation of exon 4 into the $4^{th}$ intron of the gene. The soluble CSF3R variant is 599 base pair long encoding a polypeptide of 189 amino acids. The first exon spans from base 1 to base 84 and the second exon spans from base 85 to base 599. Thus, the protein sequence of the soluble CSF3R variant is characterized by the N-terminal part of membrane bound CSF3R coded by exon 3 and exon 4 and by 69 supplementary amino acids coming form the prolongation into intron 4.

Thus, the CSF3R polypeptide variants of this invention comprise a functional ligand-binding domain, but lack a functional trans-membrane domain and further optionally lack a cytoplasmic region. The invention shows that such proteins are produced naturally, and represent unexpected CSF3R variants with unusual structural conformation. Indeed, the molecules of the present invention contain unique 69 additional amino acids after the Ig-like domain. The 69 additional amino acids consist of amino acid residues 97 to 165 of SEQ ID NO:4. sCFS3R of the present invention is also characterized by the fact that it retains only the Ig-like domain (in full) of the ligand-binding domain, lacking the CRH module and all the fibronectin type-III domains. Thus, the polypeptides of the present invention preferably lack the CRH module and/or one, two, three, four, five or all fibronectin type-III domain(s). The Ig-like domain is required for receptor homodimerization with CSF3 in solution and the Ig-like domain was shown to bind to CSF3 (Layton et al. J Biol. Chem. 2001 Sep. 28; 276(39):36779-87.). Thus, the soluble CSF3R variant of the present invention as recited in SEQ ID NO:4, retains the essential features of the CSF3 ligand binding domain, which consists of the Ig-like domain.

The CSF3R polypeptide variants of this invention lack a functional trans-membrane domain, i.e., they do not contain a CSF3R-derived functional domain allowing membrane-anchoring of the polypeptide. The absence of a functional trans-membrane domain may result from any amino acid alteration (e.g., deletion, substitution and/or addition of one or several amino acid residues) in a CSF3R trans-membrane domain resulting in a non-functional trans-membrane domain. In a typical embodiment, the lack of a functional trans-membrane domain results from a deletion of all or part of the amino acid residues forming the trans-membrane domain, preferably a deletion of amino acid residues 628 to 650 of SEQ ID NO: 10.

In one aspect, the invention provides an isolated CSF3R polypeptide variant, or a distinctive fragment thereof, wherein said polypeptide variant comprises or consists of a sequence of a ligand-binding domain, lacks a functional trans-membrane domain and lacks a cytoplasmic domain.

The current understanding of the mechanisms of soluble receptors includes their role as inhibitors of their respective membrane-bound receptors by competing for the ligands, downregulators of the expression of membrane-bound receptors, stabilizing proteins of ligands, and participants of ligand-induced signalling. Ku et al. have shown that a soluble form of the G-CSF receptor (named sG-CSFR) can synergize with the steel factor (SF, Kit ligand) or Flt3/Flk2 ligand (FL) in supporting the proliferation of primitive hematopoietic progenitors (Ku et al. Blood. 1996 Dec. 1; 88(11):4124-31). Ku et al. indicate that the soluble G-CSF receptor appear to transduce signals by interacting with its respective membrane-bound receptor.

Thus, the soluble CSF3R polypeptide variants of the present invention represent stabilizing proteins of ligands and/or membrane anchored CSF3R, promoting ligand-induced signaling and acting as CSF3R agonists. The soluble receptors of the present invention can either stabilize a ligand, the membrane-bound CSF3R or both a ligand and the membrane bound CSF3R. Preferably, the ligand is CSF3. Soluble CSF3R may prevent its cognate ligands from degradation as has been shown for soluble growth hormone receptors.

Asano et al. showed that a chimeric soluble CSF3R could inhibit the biological activity of CSF3 on normal bone marrow colony formation (Asano et al. Cancer Res. 1997 Aug. 15; 57(16):3395-7). In addition, the chimeric soluble CSF3R completely inhibited the stimulatory effect of CSF3 on the proliferation of leukemic progenitor cells to form leukemic blast colonies, representing a potential therapeutical candidate in a clinical application for acute myeloblastic leukemia. Iwasaki et al. suggested that soluble isoforms of CSF3R might compete with membrane-anchored CSF3R on the target cells and serve as negative regulators of myelopoiesis (Iwasaki et al. J. Immunol. 1999 Dec. 15; 163(12):6907-11).

Thus, the soluble CSF3R polypeptide variants of the present invention may represent decoys that can bind natural, endogenous ligands of CSF3R thereby reducing CSF3R-mediated activities, acting as CSF3R antagonists. In particular, such soluble CSF3R polypeptide variants act as regulators for the CSF3R-mediated activities by a dominant-negative mechanism.

Preferably, the soluble CSF3R polypeptide variants of the present invention represent stabilizing proteins of ligands and/or membrane anchored CSF3R, promoting ligand-induced signaling and acting as CSF3R agonists.

Layton et al., by modelization of the Ig-like domain showed that the CSF3R domain structure is also found in the closest homologue gp130, which is the shared signal transducing receptor chain of the interleukin (IL)-6 family of cytokines (Layton et al. J Biol. Chem. 2001 Sep. 28; 276(39): 36779-87.). The G-CSF3R and gp130 share 46% sequence similarity in the extracellular region. In addition, similar structural relationship is observed between the tetrameric 2:2 complexes formed by IL-6 with gp30, or CSF3 with CSF3R. Formation of complexes between IL-6 with its soluble receptor (sIL-6R), which interact with gp130, leads to an increased expression and nuclear translocation of STAT3, which causes the induction of anti-apoptotic genes, such as Bcl-x1 (Atreya R and Neurath M F. Clin Rev Allergy Immunol. 2005 June; 28(3):187-96.).

Another object of the present invention resides in a receptor complex comprising a CSF3R polypeptide variant of the present invention.

Another object of the present invention resides in a receptor complex comprising a fusion protein comprising a CSF3R polypeptide variant of the present invention.

Another object of the present invention resides in a receptor complex formed by CSF3, soluble CSF3R variants of the present invention and membrane-anchored CSF3R.

Another object of the present invention resides in a receptor complex formed by soluble CSF3R variants of the present invention and membrane-anchored CSF3R.

Another object of the present invention resides in a receptor complex formed by CSF3 and soluble CSF3R variants of the present invention.

Preferably, the receptor complex consists of a tetrameric 2:2 complex.

Soluble CSF3R polypeptide variants of this invention represent natural agonists and/or antagonists of CSF3R and may be used as such, or in the form of, e.g., a fusion protein, conjugate or receptor complex, for treating graft-vs-host disease, cancer, neutropenia, neurological disorders or conditions, pneumonia, autoimmune diseases, haematological diseases, hemopoietic disorders, infectious diseases, inflammatory bowel disease, and diabetes.

Another object of this invention resides in a soluble CSF3R comprising the immunoglobulin (Ig)-like domain and the CRH module fused to an amino acid sequence comprising or consisting of one or more amino acids encoded by intron 4 of SEQ ID NO:1. Preferably, an object of this invention resides in a soluble CSF3R comprising the immunoglobulin (Ig)-like domain fused to an amino acid sequence comprising or consisting of one or more amino acids encoded by intron 4 of SEQ ID NO: 1. Preferably, the Ig-like domain is fused to an amino acid sequence comprising or consisting of 1, 2, 5, 10, 25, 50 or 69 amino acids encoded by intron 4 of SEQ ID NO: 1. Alternatively, the Ig-like domain is fused to an amino acid sequence comprising or consisting of 1, 2, 5, 10, 25, 50 or 69 amino acids from amino acids 97 to 165 of SEQ ID NO:4 (mature sCSF3R). Preferably, the Ig-like domain is fused to an amino acid sequence consisting of amino acids 97 to 165 of SEQ ID NO:4.

In another aspect, the invention thus provides an isolated CSF3R polypeptide variant of the present invention wherein the polypeptide further includes the amino acid sequence encoded by intron 4 of SEQ ID NO: 1 or further includes a fragment of the amino acid sequence encoded by intron 4 of SEQ ID NO:1 of at least 3, 4, 5, 7, 10, 15, 20, 25, 30, 40, 50, 60 or 69 amino acids. Preferably, an isolated CSF3R polypeptide further includes an amino acid sequence consisting of amino acids 97 to 165 of SEQ ID NO:4.

More particularly, the invention results from the identification, isolation and characterization of a naturally-occurring, novel soluble splicing variant of human CSF3R, named sCSF3R (SEQ ID NO:2), having particular structural and biological properties, which represents a valuable pharmaceutical product. Thus, an object of the present invention resides in the soluble CSF3R as recited in SEQ ID NO:2, the mature form thereof, the glycosylated form thereof, the functional equivalent thereof or a distinctive fragment thereof. Preferably, the mature form of SEQ ID NO:2 is SEQ ID NO:4.

Thus, another object of this invention resides in the mature form of the soluble CSF3R variant as recited in SEQ ID NO:4. Alternatively, an object of this invention resides in SEQ ID NO:2 lacking the signal peptide. Preferably, the signal peptide spans from amino acids 1 to 25 of SEQ ID NO:2, or amino acids 1 to 24 of SEQ ID NO:2, or amino acids 1 to 23 of SEQ ID NO:2.

Other objects of this invention reside in the cloned sequence as recited in SEQ ID NO:6, the mature form thereof, the glycosylated form thereof, the functional equivalent thereof or a distinctive fragment thereof. Preferably, the mature form of SEQ ID NO:6 is SEQ ID NO:8.

Thus, another object of this invention resides in the mature form of the soluble CSF3R variant as recited in SEQ ID NO:8. Alternatively, an object of this invention resides in SEQ ID NO:6 lacking the signal peptide. Preferably, the signal peptide spans from amino acids 1 to 25 of SEQ ID NO:6, or amino acids 1 to 24 of SEQ ID NO:6, or amino acids 1 to 23 of SEQ ID NO:6.

A particular object of this invention resides in isolated CSF3R polypeptide variants, or a distinctive fragment thereof, wherein said polypeptide variants comprise a sequence of a CSF3 ligand-binding domain and lack a functional trans-membrane domain. Preferably, the CSF3 ligand-binding domain consists of amino acid residues 25 to 627 of SEQ ID NO:10, more preferably consist of amino acid residues 25 to 618 of SEQ ID NO: 10, even more preferably consists of the Ig-like domain and CRH domain of membrane bound CSF3R or consist of amino acid residues 25 to 330 of SEQ ID NO: 10. The most preferred CSF3-ligand binding domain consists of the Ig like domain of membrane bound CSF3R, or consists of amino acid residues 25 to 120 of SEQ ID NO:10 (as recited in SEQ ID NO:12), or consists of amino acids 25 to 117 of SEQ ID NO:10.

Another object of this invention resides in isolated CSF3R polypeptide variants, or a distinctive fragment thereof, wherein said polypeptide variants comprise a sequence of a CSF3 ligand-binding domain, lack a functional trans-membrane domain and lack a cytoplasmic region. Preferably, the transmembrane domain consists of amino acid residues 628 to 650 of SEQ ID NO:10. Preferably, the cytoplasmic region consists of amino acid residues 651 to 836 of membrane bound CSF3R (SEQ ID NO: 10).

Thus, another object of the present invention resides in an isolated CSF3R polypeptide variant of the present invention, wherein said isolated CSF3R polypeptide variant lacks amino acids 628 to 650 of SEQ ID NO:10 and/or lacks amino acids 651 to 836 of SEQ ID NO:10.

Another object of this invention resides in an isolated CSF3R polypeptide variant encoded by intron 4 of SEQ ID NO: 1, or a fragment thereof.

Another object of this invention resides in an isolated CSF3R polypeptide variant consisting of amino acids 97 to 165 of SEQ ID NO:4.

Another object of this invention resides in an isolated CSF3R polypeptide variant encoded by intron 4 of SEQ ID NO: 1, or a fragment thereof, fused to one or more amino acids of the ligand-binding domain, preferably the Ig-like domain.

Another object of this invention thus resides in an isolated CSF3R polypeptide variant, wherein said polypeptide comprises or consists of the amino acid sequence encoded by intron 4 of SEQ ID NO: 1 or of a fragment of the amino acid sequence encoded by intron 4 of SEQ ID NO:1 of at least 6, 7, 8, 10, 15, 20, 25, 30, 40, 50, 60 or 69 amino acids. In another object of this invention, such isolated CSF3R polypeptide may be fused to one or more amino acids of the ligand-binding domain of CSF3R.

Another object of the present invention resides in the Ig-like domain of membrane bound CSF3R or a fragment thereof fused to amino acid residues 97 to 165 of SEQ ID NO: 4. Another object of the present invention resides in the Ig-like domain of membrane bound CSF3R or a fragment thereof fused to a fragment of the sequence consisting of amino acid residues 97 to 165 of SEQ ID NO: 4. Preferably, the fragment consists of amino acid residues 98 to 100 of SEQ ID NO: 4, or amino acid residues 98 to 120 of SEQ ID NO: 4, or amino acid residues 98 to 150 of SEQ ID NO: 4.

Preferably, a ligand binding domain of the present invention is an immunoglobulin-like domain of CSF3R.

Preferably, an immunoglobulin like-domain of the present invention is an Ig-like C2-type domain. Preferably, the Ig-like C2-type domain contains two cysteine residues forming a disulphide bridge.

Preferably, an Ig-like domain of the present invention contains eight β-strands. Preferably, an Ig-like domain of the present invention contains two disulfide bonds between Cys-2-Cys-77 and Cys-22-Cys-28 of SEQ ID NO:4, more preferably between Cys-2-Cys-28 and Cys-22-Cys-77 of SEQ ID NO: 4.

Another object of this invention resides in the Ig-like domain of membrane bound CSF3R as recited in SEQ ID NO:10. Preferably, the Ig-like domain consists of amino acid residues 25 to 120 of SEQ ID NO:10 (as recited in SEQ ID NO:12) or amino acid residues 25 to 117 of SEQ ID NO: 10.

Preferably, the polypeptides of the present invention are soluble, i.e., they do not contain a functional membrane-anchoring sequence and may thus circulate within body fluids. In a most preferred aspect, the polypeptides of the present invention are naturally-occurring soluble polypeptides.

Another object of the present invention thus resides in a soluble isolated CSF3R variant. Preferably, the soluble isolated CSF3R variant is a naturally-occurring soluble variant.

Also, preferred CSF3R polypeptide variants of this invention retain the ability to bind CSF3R natural ligands. Such polypeptides thus function as agonists and/or antagonists and may be used to stimulate and/or inhibit CSF3R-mediated activities in, e.g., pathological conditions. Preferably, the polypeptides of the present invention function as agonists of CSF3.

Another object of the present invention resides in an isolated CSF3R polypeptide variant according to the present invention, wherein the variant is selected from a mature form thereof, a glycosylated form thereof, a pegylated form thereof, a functional equivalent thereof or a distinctive fragment thereof.

It should be understood that the term CSF3R also includes functional equivalents of the above sequence, i.e., naturally-occurring polymorphisms, sequences originating from other species, as well as sequences comprising one or more amino acid modification(s) that do(es) not substantially affect CSF3R protein function. Functional equivalents typically exhibit 80, 85, 90, 91, 92, 93, 94, 95, 96, 97, 98 or 99% sequence identity with SEQ ID NO: 2.

The sequence derived from the ligand-binding domain of CSF3R may be derived from or comprise the sequence of all or a ligand-binding part of the extra-cellular domain of CSF3R, or a functional equivalent thereof. As mentioned above, a functional equivalent designates any modified sequence comprising one or more amino acid deletion, addition and/or substitution, preferably 1, 2, 3, 5, 10, 15, 20, 30, 50 or more deletion, addition and/or substitution that retains the ability to bind a CSF3R ligand.

A specific embodiment of this invention is a CSF3R polypeptide variant having or comprising SEQ ID NO: 4, a functional equivalent thereof or a distinctive fragment thereof, that retain CSF3R agonist activity.

A specific embodiment of this invention is a CSF3R polypeptide variant having or comprising SEQ ID NO: 4, a functional equivalent thereof or a distinctive fragment thereof, that retain CSF3R antagonist activity.

The present invention also includes any polypeptide comprising a distinctive fragment of a CSF3R polypeptide variant as disclosed above. Within the context of this invention, a distinctive fragment designates a fragment of at least 5 consecutive amino acids that comprises a junction sequence formed as a result of the deleted intervening amino acid residues. Such a distinctive fragment may preferably comprise up to 10, 20, 30, 40, 50, 60, 70, 80, 90, 100, 110, 120, 130, 140, 150, 160, 170, 180, or more consecutive amino acid residues of the variant, preferably comprising the above defined junction sequence. Preferably, a fragment of the present invention consists of at least 6, 7, 8, 10, 20, 30, 40, 60, 80, 100, 120, 140, 160, 180, 185, 187 or 188 amino acids of SEQ ID NO:2. Preferably, the fragment consists of consecutive amino acids.

As used herein, the term "fragment" refers to a polypeptide having an amino acid sequence that is the same as part, but not all, of the amino acid sequence of the CSF3R polypeptide or one of its functional equivalents. The fragments should comprise at least n consecutive amino acids from the sequence and, depending on the particular sequence, n preferably is 7 or more, preferably, 8, 10, 20, 30, 40, 60, 80, 100, 120, 140, 160, 180, 185, 187 or 188 amino acids of SEQ ID NO:2. Small fragments may form an antigenic determinant.

Preferably, the minimum length of the fragment is of 6, 10, 20, 30, 40, 50, 60, 68, 100, 150, 200, 250, 300, 350, 400, 450 or 500 amino acids.

Preferably, the maximum length of the fragment is of 188, 187, 186, 185, 180, 170, 166, 165, 164, 163, 160, 155, 150, 125, 100, 75 or 50 amino acids.

Preferably, the minimum length of the fragment is of 18, 30, 60, 90, 120, 150, 180, 204, 300, 450, 600, 750, 1050, 1200, 1350 or 1500 nucleic acids.

Preferably, the maximum length of the fragment is of 564, 561, 558, 555, 540, 510, 498, 495, 492, 489, 480, 465, 450, 375, 300, 225 or 150 nucleic acids.

Preferably, the maximum length of a polypeptide of the present invention is 189, 190, 192, 195, 200, 210, 230, 250, 300, 400, 500, 600, 650, 700, 800, 900, 1000, 1250, 1500, 2000, 2500, 3000, 3500, 4000, 4500 or 5000 amino acids.

Preferably, the maximum length of a nucleic acid of the present invention is 567, 570, 576, 585, 600, 630, 690, 750, 900, 1200, 1500, 1800, 1950, 2100, 2400, 2700, 3000, 5000, 7500, 10000, 20000, 30000, 50000, 75000 or 100000 nucleic acids.

Preferably, the functional equivalent has at least 75% identity, preferably at least 80%, 85%, 90%, 95%, 98% or 99% identity with SEQ ID NO:4.

Preferably, the functional equivalent has an antigenic determinant in common with SEQ ID NO:4 which consists of 6, 7, 8, 10, 12, 14, 16, 18, 20, 22, 26, 30, 34, 38 or more amino acids of SEQ ID NO:4.

An "antigenic determinant" of the present invention may be a part of a polypeptide of the present invention, which binds to an antibody-combining site or to a T-cell receptor (TCR). Alternatively, an "antigenic determinant" may be a site on the surface of a polypeptide of the present invention to which a single antibody molecule binds. Generally an antigen has several or many different antigenic determinants and reacts with antibodies of many different specificities. Preferably, the antibody is immunospecific to a polypeptide of the invention. Preferably, the antibody is immunospecific to a polypeptide of the invention, which is not part of a fusion protein. Preferably, the antibody is immunospecific to CSF3R or a fragment thereof. Antigenic determinants usually consist of chemically active surface groupings of molecules, such as amino acids or sugar side chains, and can have specific three dimensional structural characteristics, as well as specific charge characteristics. Preferably, the "antigenic determinant" refers to a particular chemical group on a polypeptide of the present invention that is antigenic, i.e. that elicit a specific immune response.

Preferably, the functional equivalent contains one or more amino acid modifications, one or more non-conservative substitutions, one or more conservative substitutions and/or one or more amino acid derivatives.

As used herein, "functional equivalent" refers to a protein or nucleic acid molecule that possesses functional or structural characteristics that are substantially similar to a polypeptide or nucleic acid molecule of the present invention. A functional equivalent of a protein may contain modifications depending on the necessity of such modifications for the performance of a specific function. The term "functional equivalent" is intended to include the fragments, mutants, hybrids, variants, analogs, or chemical derivatives of a molecule.

In a further preferred embodiment, the functional derivative comprises at least one moiety attached to one or more functional groups, which occur as one or more side chains on the amino acid residues. Preferably, the moiety is a polyethylene (PEG) moiety. PEGylation may be carried out by known methods, such as the ones described in WO99/55377, for example.

Polypeptides may contain amino acids other than the 20 gene-encoded amino acids, modified either by natural processes, such as by post-translational processing or by chemical modification techniques which are well known in the art. Among the known modifications which may commonly be present in polypeptides of the present invention are glycosylation, lipid attachment, sulphation, gamma-carboxylation, for instance of glutamic acid residues, hydroxylation and ADP-ribosylation. Other potential modifications include acetylation, acylation, amidation, covalent attachment of flavin, covalent attachment of a haeme moiety, covalent attachment of a nucleotide or nucleotide derivative, covalent attachment of a lipid derivative, covalent attachment of phosphatidylinositol, cross-linking, cyclization, disulphide bond formation, demethylation, formation of covalent cross-links, formation of cysteine, formation of pyroglutamate, formylation, GPI anchor formation, iodination, methylation, myristoylation, oxidation, proteolytic processing, phosphorylation, prenylation, racemization, selenoylation, transfer-RNA mediated addition of amino acids to proteins such as arginylation, and ubiquitination.

Modifications can occur anywhere in a polypeptide, including the peptide backbone, the amino acid side-chains and the amino or carboxyl termini. In fact, blockage of the amino or carboxyl terminus in a polypeptide, or both, by a covalent modification is common in naturally-occurring and synthetic polypeptides and such modifications may be present in polypeptides of the present invention.

The modifications that occur in a polypeptide often will be a function of how the polypeptide is made. For polypeptides that are made recombinantly, the nature and extent of the modifications in large part will be determined by the post-translational modification capacity of the particular host cell and the modification signals that are present in the amino acid sequence of the polypeptide in question. For instance, glycosylation patterns vary between different types of host cell.

The polypeptides of the present invention can be prepared in any suitable manner. Such polypeptides include isolated naturally-occurring polypeptides (for example purified from cell culture), recombinantly-produced polypeptides (including fusion proteins), synthetically-produced polypeptides or polypeptides that are produced by a combination of these methods.

Functional equivalents include natural biological variants (for example, allelic variants or geographical variations within the species from which the polypeptides are derived) and mutants (such as mutants containing amino acid substitutions, insertions or deletions) of the CSF3R polypeptides. Such mutants may include polypeptides in which one or more of the amino acid residues are substituted with a conserved or non-conserved amino acid residue (preferably a conserved amino acid residue) and such substituted amino acid residue may or may not be one encoded by the genetic code. Typical such substitutions are among Ala, Val, Leu and Ile; among Ser and Thr; among the acidic residues Asp and Glu; among Asn and Gln; among the basic residues Lys and Arg; or among the aromatic residues Phe and Tyr. Particularly preferred are variants in which several, i.e. between 5 and 10, 1 and 5, 1 and 3, 1 and 2 or just 1 amino acids are substituted, deleted or added in any combination. Especially preferred are silent substitutions, additions and deletions, which do not alter the properties and activities of the protein. Also especially preferred in this regard are conservative substitutions.

Such mutants also include polypeptides in which one or more of the amino acid residues includes a substituent group.

In accordance with the present invention, any substitution should be preferably a "conservative" or "safe" substitution, which is commonly defined a substitution introducing an amino acids having sufficiently similar chemical properties (e.g. a basic, positively charged amino acid should be replaced by another basic, positively charged amino acid), in order to preserve the structure and the biological function of the molecule.

The literature provide many models on which the selection of conservative amino acids substitutions can be performed on the basis of statistical and physico-chemical studies on the sequence and/or the structure of proteins (Rogov S I and Nekrasov A N, 2001). Protein design experiments have shown that the use of specific subsets of amino acids can produce foldable and active proteins, helping in the classification of amino acid "synonymous" substitutions which can be more easily accommodated in protein structure, and which can be used to detect functional and structural homologs and paralogs (Murphy L R et al., 2000). The groups of synonymous amino acids and the groups of more preferred synonymous amino acids are shown in Table 1.

Specific, non-conservative mutations can be also introduced in the polypeptides of the invention with different purposes. Mutations reducing the affinity of the FN3 domain containing protein may increase its ability to be reused and recycled, potentially increasing its therapeutic potency (Robinson C R, 2002). Immunogenic epitopes eventually present in the polypeptides of the invention can be exploited for developing vaccines (Stevanovic S, 2002), or eliminated by modifying their sequence following known methods for selecting mutations for increasing protein stability, and correcting them (van den Burg B and Eijsink V, 2002; WO 02/05146, WO 00/34317, WO 98/52976).

Preferred alternative, synonymous groups for amino acids derivatives included in peptide mimetics are those defined in Table 2. A non-exhaustive list of amino acid derivatives also include aminoisobutyric acid (Aib), hydroxyproline (Hyp), 1,2,3,4-tetrahydro-isoquinoline-3-COOH, indoline-2-carboxylic acid, 4-difluoro-proline, L-thiazolidine-4-carboxylic acid, L-homoproline, 3,4-dehydro-proline, 3,4-dihydroxyphenylalanine, cyclohexyl-glycine, and phenylglycine.

By "amino acid derivative" is intended an amino acid or amino acid-like chemical entity other than one of the 20 genetically encoded naturally occurring amino acids. In particular, the amino acid derivative may contain substituted or non-substituted, linear, branched, or cyclic alkyl moieties, and may include one or more heteroatoms. The amino acid derivatives can be made de novo or obtained from commercial sources (Calbiochem-Novabiochem AG, Switzerland; Bachem, USA).

Various methodologies for incorporating unnatural amino acids derivatives into proteins, using both in vitro and in vivo translation systems, to probe and/or improve protein structure and function are disclosed in the literature (Dougherty D A, 2000). Techniques for the synthesis and the development of peptide mimetics, as well as non-peptide mimetics, are also well known in the art (Golebiowski A et al., 2001; Hruby V J and Balse P M, 2000; Sawyer T K, in "Structure Based Drug Design", edited by Veerapandian P, Marcel Dekker Inc., pg. 557-663, 1997).

"Identity" indicates that at any particular position in the aligned sequences, the amino acid residue is identical between the sequences.

Typically, greater than 30% identity between two polypeptides is considered to be an indication of functional equivalence. Preferably, functionally equivalent polypeptides of the first aspect of the invention have a degree of sequence identity with the CSF3R polypeptides, or with active fragments thereof, of greater than 70% or 80%. More preferred polypeptides have degrees of identity of greater than 85%, 90%, 95%, 98%, 98.5%, 99% or 99.5% respectively.

Preferably, the "functional equivalent" may be a protein or nucleic acid molecule that exhibits any one or more of the functional activities of the polypeptides of the present invention.

Preferably, the "functional equivalent" may be a protein or nucleic acid molecule that displays substantially similar activity compared with CSF3R or fragments thereof in a suitable assay for the measurement of biological activity or function. Preferably, the "functional equivalent" may be a protein or nucleic acid molecule that displays identical or higher activity compared with CSF3R or fragments thereof in a suitable assay for the measurement of biological activity or function. Preferably, the "functional equivalent" may be a protein or nucleic acid molecule that displays 50%, 60%, 70%, 80%, 90%, 95%, 98%, 99%, 100% or more activity compared with CSF3R or fragments thereof in a suitable assay for the measurement of biological activity or function.

Preferably, the "functional equivalent" may be a protein or polypeptide capable of exhibiting a substantially similar in vivo or in vitro activity as the polypeptides of the invention. Preferably, the "functional equivalent" may be a protein or polypeptide capable of interacting with other cellular or extracellular molecules in a manner substantially similar to the way in which the corresponding portion of the polypeptides of the invention would. For example, a "functional equivalent" would be able, in an immunoassay, to diminish the binding of an antibody to the corresponding peptide (i.e., the peptide the amino acid sequence of which was modified to achieve the "functional equivalent") of the polypeptide of the invention, or to the polypeptide of the invention itself, where the antibody was raised against the corresponding peptide of the polypeptide of the invention. An equimolar concentration of the functional equivalent will diminish the aforesaid binding of the corresponding peptide by at least about 5%, preferably between about 5% and 10%, more preferably between about 10% and 25%, even more preferably between about 25% and 50%, and most preferably between about 40% and 50%.

For example, functional equivalents can be fully functional or can lack function in one or more activities. Thus, in the present invention, variations can affect the function, for example, of the activities of the polypeptide that reflect its possession of an Ig-like domain.

Activity of a polypeptide of the present invention can be confirmed in at least one of the following assays:
- in the modulation of the proliferation, survival, and maturation of cells committed to the neutrophilic granulocyte lineage, or
- in the modulation of the activation of multiple signal transduction pathways, including Signal Transducer and Activators of Transcription (STATs), Ras/Raf/Erk, phosphatidylinositol 3-kinase (PI3-K)/Akt, but also Stat proteases such as the Stat5 protease, or
- in the improvement of cardiac function, or
- in the modulation of anti-apoptotic proteins induction, inhibition of apoptotic death of cardiomyocytes after myocardial infarction and improved cardiac function, or
- in the reduction of apoptosis of endothelial cells and increase of vascularization in the infarcted heart protecting against ischemic injury, or
- in the survival of cardiac myocytes and in the prevention of left ventricular remodeling after myocardial infarction, or
- in the prolonged survival and increased activation of neutrophils combined with a sustained release of anti-inflammatory cytokines in patients with community-acquired pneumonia (CAP), or
- in the synergy with the steel factor (SF, Kit ligand) or Flt3/Flk2 ligand (FL) in supporting the proliferation of primitive hematopoietic progenitors, or
- in the inhibition of the biological activity of CSF3 on normal bone marrow colony formation, inhibition of the stimulatory effect of CSF3 on the proliferation of leukemic progenitor cells to form leukemic blast colonies.

Another object of the present invention is the administration of a polypeptide of the present invention to a patient to exert one or more of the biological activities described above.

Alternatively, activity of a polypeptide of the present invention can be confirmed in at least one of the following assays (as reviewed by Rutella et al. J. Immunol. 2005 Dec. 1; 175(11):7085-91):
- in the modulation of proliferation and differentiation of normal hemopoietic stem cells (HSCs), or
- in the modulation of neutrophil reconstitution following radiation- or chemotherapy-induced myelosuppression, or
- in the modulation of effector functions in mature neutrophils, and mobilization of bone marrow HSCs into the peripheral blood, or
- in the interaction with the immune system by altering T cell reactivity and modifying APC function (e.g. modulation of CSF binding to human mitogen-activated $CD3^+$ T cells and to T lymphoblastoid cell lines; e.g. modulation of T cell immunomodulatory genes, e.g., GATA-3 and Stat5, which directly inhibit proinflammatory cytokine production by T cells at pharmacologic doses), or
- in the modulation of cytokine production (e.g. modification of ex vivo cytokine production by human white blood cells; e.g. modulation of IL-1β, IL-12, IFN-γ, IL-18, and TNF-α production by LPS-stimulated whole blood and/or monocytes; e.g. modulation of LPS-induced release of IL-1 receptor antagonist (IL-1ra) and soluble p55 and p75 TNFRs; e.g. modulation of plasma levels of soluble TNFRs and IL-1β compared with control subjects not pre-treated with a polypeptide of the present invention in healthy volunteers subsequently given *Salmonella abortus equi* endotoxin, suggesting in vivo anti-inflammatory effects; e.g. modulation of TNF-α production by normal, alloantigen-activated PBMCs at posttranscriptional level; Modulation of the elevation of serum hepatocyte growth factor, an angiogenic cytokine that might contribute to microvessel formation induced by CSF3; e.g. modulation of soluble human HLA Ags levels, e.g., HLA-G and HLA class I, that reportedly modulate alloimmune responses), or
- in the in vitro differentiation of tolerogenic dendritic cell (DC)-like, or
- in the modulation of T cell functions (e.g. in healthy subjects, modulation of the inhibition of T cell proliferation in response to mitogens through the release of soluble inhibitory factors; e.g. modulation in the ability of NKT cells to expand in vitro in response to α-galactosylceramide; e.g. mobilization of functional bone marrow $CD4^+CD25^+FoxP3^+$ regulatory T (Treg) cells as well as natural suppressor $CD4^-CD8^-TCR\alpha^+\beta^+$ T cells, modulation of the expression of CXCL12/SDF-1α, a CXCR4 ligand, in the bone marrow, thus modulating $CD4^+CD25^+$ Treg cell trafficking; e.g. modulation of T cell mitogen responses and lymphokine-activated killer cell-mediated cytotoxicity, which have been correlated with expression of individual HLA alleles), or
- in the induction of Treg cells (e.g. modulation of human Tr1 cells generation; e.g. modulation of IL-10-producing Treg cells generation and promotion of transplantation tolerance), or
- in the modulation of DC number and function (e.g. mobilization of DC2, which induces allogeneic naive T cells to produce IL-4 and IL-10; e.g. modulation of CCR7 expression on blood DCs, thus affecting DC migratory and homing ability; e.g. modulation of IL-12 production by DCs recovering after myeloablative HSC transplantation; e.g. modulation of IL-10 and IFN-α production, which are involved in Treg cells differentiation, e.g. in the differentiation pathway of human monocyte-derived DCs), or
- in the expansion of myeloid precursors as tolerogenic APCs (e.g. in the expansion of a murine GM precursor population with regulatory activity; e.g. in the modulation of the development of GVHD when cotransplanted in allogeneic recipient animals; e.g. in the in vitro differentiation of Treg cells specific for host Ags favored by expanded GM cells), or
- in the modulation of HSC transplantation (e.g. by using a hybrid resistance system in which NK cells mediate vigorous rejection, modulation of the engraftment of bone marrow parental cells and appearance of splenic colonies of donor origin by continuous pretreatment of $F_1$ hybrid mice; e.g. acceptance of xenotransplanted rat bone marrow cells in transgenic mice expressing a polypeptide of the invention; e.g. in the down-regulation of T cell proliferation to mitogens and alloantigens and decrease of type 1 cytokine production by T cells in mice; e.g. release of IL-4 by T cells treated with a polypeptide of the invention, which is consistent with a shift to a Th2 cytokine pattern; e.g. ability of donor cells to mediate acute GVHD and improvement of overall survival in recipient mice after pretreatment of donor mice with a polypeptide of the invention; e.g. increase in the frequency of CD4⁻CD8⁻NK1.1⁺ T cells responsible for the secretion of large amounts of IL-4 in donor mice treated with a polypeptide of the invention), or in the stimulation of neuronal progenitor differentiation, neurogenesis and improvement of behavioural outcome after an ischemic lesion.

Another object of the present invention is the administration of a polypeptide of the present invention to a patient to exert one or more of the biological activities described above.

To confirm the biological activity of a polypeptide of the present invention, several known assays can be employed singularly or in combination. Example of determining function of a polypeptide of the present invention is described in Schneider et al. J Clin Invest. 2005 August; 115(8):2083-98, in Schneider et al. Cell Cycle. 2005 December; 4(12):1753-7 and in the patent application US2005/0142102. For example, methods for confirming sCFS3R function include a colony formation assay employing murine bone marrow cells; stimulation of proliferation of bone marrow cells induced by sCFS3R; specific bioassays with cells lines that may depend on sCFS3R for growth or that may respond to sCFS3R (e.g., AML-193; 32D; BaF3; GNFS-60; HL-60, MI; NFS-60; OCI/AML1a; and WEHI-3B). These and other assays are described in Braman et al. Am. J. Hematology 39: 194-201 (1992); Clogston C L et al Anal Biochem 202: 375-83 (1992); Hattori K et al Blood 75: 1228-33 (1990); Kuwabara T et al Journal of Pharmacobiodyn 15: 121-9 (1992); Motojima H et al Journal of Immunological Methods 118: 187-92 (1989); Sallerfors B and Olofsson European Journal of Haematology 49: 199-207 (1992); Shorter S C et al Immunology 75: 468-74 (1992); Tanaka H and Kaneko Journal of Pharmacobiodyn. 15: 359-66 (1992); Tie F et al Journal of Immunological Methods 149: 115-20 (1992); Watanabe M et al Anal. Biochem. 195: 38-44 (1991).

In a most preferred aspect, activity of a polypeptide of the present invention is confirmed by measuring the proliferation of primitive hematopoietic progenitors, by determining the number of colonies formed per dish within one, two or three days in the presence of an isolated CSF3R polypeptide variant of this invention (see Ku et al.). Preferably, activity is confirmed if at least 1, 2, 3, 5, 7, 10, 15, 20, 25, 30 or more colonies are formed per dish. Preferably, the colonies are formed within one day. Preferably, any active amount of the CSF3R polypeptide can be used.

The present invention also relates to fusion proteins comprising a CSF3R polypeptide as disclosed above, operably linked to an additional amino acid domain. The additional amino acid domain may be located upstream (N-ter) or downstream (C-ter) from the sequence of the CSF3R polypeptide. The additional domain may comprise any functional region, providing for instance an increased stability, targeting or bioavailability of the fusion protein; facilitating purification or production, or conferring on the molecule additional biological activity. Typical examples of such additional amino acid domains include, without limitation, a tag, a targeting peptide, a constant region of an immunoglobulin, a multimerization domain and/or a biologically active protein or fragment thereof or a heterodimeric protein hormone such as human chorionic gonadotropin (hCG) as described in U.S. Pat. No. 6,193,972. The term "operably linked" indicates that the polypeptide and additional amino acid domain are associated through peptide linkage, either directly or via spacer residues (e.g. one or more Gly-Ser motifs). In this manner, the fusion protein can be produced recombinantly, by direct expression in a host cell of a nucleic acid molecule encoding the same, as will be discussed below. Also, if needed, the additional amino acid sequence included in the fusion proteins may be eliminated, either at the end of the production/purification process or in vivo, e.g., by means of an appropriate endo-/exopeptidase. For example, a spacer sequence included in the fusion protein may comprise a recognition site for an endopeptidase (such as a caspase) that can be used to separate by enzymatic cleavage the desired polypeptide variant from the additional amino acid domain, either in vivo or in vitro.

Specific examples of the additional amino acid residues include a tag sequence selected e.g., from a GST sequence and a His tag sequence. The tag sequence may be linked to the C-terminus or to the N-terminus of the CSF3R polypeptide variant, preferably to the C-terminus.

In a particular embodiment, the additional amino acid residues function as a peptide signal directing secretion of the protein. CSF3R is a Type I transmembrane protein. CSF3R polypeptide variants of this invention may however be fused to a heterologous signal sequence, at the N-terminus of the polypeptide, to allow or increase secretion thereof. Such a signal peptide may be any sequence functional in a selected host cell, such as a eukaryotic (e.g., mammalian) or prokaryotic host cell. Examples of such peptide signals are well known in the art.

In a further particular embodiment, the additional amino acid residues in the fusion protein comprise an amino acid sequence derived from the constant region of an immunoglobulin, particularly the Fc portion of a human immunoglobulin. The sequence of the Fc portion may be derived for instance from an IgG, preferably from a human IgG. Preferably, it is fused to heavy chain regions, like the CH2 and CH3 domains, optionally with the hinge region of human IgG1, for example. The Fc part may e.g. be mutated in order to prevent unwanted activities, such as complement binding, binding to Fc receptors, or the like. Thus, said Ig sequence may also be modified to reduce effector function or to increase the stability of a resulting dimer. The amino acid sequence derived from the constant region of an immunoglobulin may be linked to the C-terminus or to the N-terminus of the CSF3R polypeptide variant, preferably to the C-terminus.

The generation of specific fusion proteins comprising the polypeptide of the first aspect of the invention and a portion of an immunoglobulin are described in example 11 of WO 99/09063, for example. Other isoforms of Ig molecules are also suitable for the generation of fusion proteins according to the present invention, such as isoforms $IgG_2$ or $IgG_4$, or other Ig classes, like IgM or IgA, for example. Fusion proteins may be monomeric or multimeric, hetero- or homomultimeric.

Further fusion proteins of the polypeptide of the first aspect of the invention may be prepared by fusing domains isolated from other proteins allowing the formation or dimers, trimers, etc. Examples for protein sequences allowing the multimerization of the polypeptides of the Invention are domains isolated from proteins such as hCG (WO 97/30161), collagen X (WO 04/33486), C4BP (WO 04/20639), Erb proteins (WO 98/02540), or coiled coil peptides (WO 01/00814). Polypeptides may contain amino acids other than the 20 gene-encoded amino acids, modified either by natural processes, such as by post-translational processing or by chemical modification techniques which are well known in the art. Among the known modifications which may commonly be present in polypeptides of the present invention are glycosylation, lipid attachment, sulphation, gamma-carboxylation, for instance of glutamic acid residues, hydroxylation and ADP-ribosylation. Other potential modifications include acetylation, acylation, amidation, covalent attachment of flavin, covalent attachment of a haeme moiety, covalent attachment of a nucleotide or nucleotide derivative, covalent attachment of a lipid derivative, covalent attachment of phosphatidylinositol, cross-linking, cyclization, disulphide bond formation, demethylation, formation of covalent cross-links, formation of cysteine, formation of pyroglutamate, formylation, GPI anchor formation, iodination, methylation, myristoylation, oxidation, proteolytic processing, phosphorylation, prenylation, racemization, selenoylation, transfer-RNA mediated addition of amino acids to proteins such as arginylation, and ubiquitination.

In a further particular embodiment, the additional amino acid residues in the fusion protein comprise a multimerization domain, allowing complexes to be formed between two or more fusion proteins of this invention, or between one or more fusion proteins of this invention and a distinct protein. An example of such multimerization domains include a leucine zipper. The multimerization domain may be linked to the C-terminus or to the N-terminus of the CSF3R polypeptide variant, preferably to the C-terminus.

It should be understood that fusion proteins of this invention may comprise either only one of the above additional amino acid residues, or a combination thereof. For instance, a fusion protein may comprise a signal peptide and a tag sequence, or a signal peptide and a multimerization domain or a signal peptide and the constant region of an immunoglobulin, or a tag and the constant region of an immunoglobulin. Also, as indicated above, some of the additional amino acid sequences may be linked to the CSF3R polypeptide variant through spacer residues, particularly through cleavable spacer residues allowing subsequent separation of these elements, if needed. Such fusion proteins may be produced by any conventional technique known per se in the art, as will be discussed below.

Thus, according to an embodiment of the present invention, there is provided a hybrid fusion protein which is a multimeric protein comprising more than one fusion polypeptide. Thus, the fusion proteins described above may form homodimers and heterodimers and these are also included in the invention. The hybrid fusion protein may contain two, three, four of more fusion polypeptides according to the first embodiment of the sixth aspect of the invention described above. Preferably, the hybrid fusion protein is a dimer comprising two fusion polypeptides as described above. Where the hybrid fusion protein is a dimer, it may be a homodimer or a heterodimer. Preferably, the hybrid fusion protein comprises or consists of more than one fusion polypeptides selected from the above fusion polypeptides. The invention thus includes homodimers comprising two fusion polypeptides. The invention further includes heterodimers comprising combinations of these sequences.

Non-immunoglobulin proteins such as heterodimeric proteinaceous hormones, can thus also be used for making fusion proteins. The fusion proteins employ the α and β chains of a heterodimeric hormone or a portion thereof as a scaffold to which a polypeptide of the present invention is linked. An example of a heterodimeric proteinaceous hormone is the human chorionic gonadotropin (hCG) hormone, a stable secreted protein with a long half-life. Examples of hybrid proteins employing hCG can be found in U.S. Pat. No. 6,194, 177, to Campbell et al., the entire contents of which are incorporated by reference herein.

In general, the hybrid proteins of the invention include at least two polypeptide chains, where each polypeptide chain includes at least one polypeptide of the present invention linked to a subunit of a heterodimeric proteinaceous hormone, or a fragment thereof. Examples of proteinaceous heterodimeric hormones for use in this invention include but are not limited to FSH, inhibin, TSH, hCG, and LH.

In some embodiments, one of the subunits of the heterodimeric proteinaceous hormone in the hybrid protein comprises one or more alterations which reduce or eliminate the biological activity of the hormone, while preserving the ability of the altered subunit to dimerize with another subunit of the hormone. In some embodiments, an altered subunit is an alpha subunit of hCG which comprises a deletion of amino acids 88-92 (del 88-92), named alpha des88-92, thereby rendering the hCG biologically inactive; however, preserving the ability of the alpha subunit to dimerize with the beta subunit of hCG (removal of just five residues at the extreme carboxyl-terminus of a subunit of hCG can effectively eliminate its biological activity while preserving its capability to form heterodimers). In another embodiment, an altered subunit is an alpha subunit which comprises substitution of a cysteine residue at amino acid position 26 with an alanine (C26A). In another embodiment, an altered subunit is an alpha subunit comprising a deletion of amino acids 88-92 (del 88-92) and substitution of a cysteine residue at amino acid position 26 with an alanine (C26A). In another embodiment, an altered subunit is a beta subunit comprising a deletion of amino acids 104-145 (del 104-145). The hybrid proteins of the invention may comprise: a) an altered alpha subunit and an unaltered beta subunit; b) an altered alpha subunit and an altered beta subunit; c) an unaltered alpha subunit and an altered beta subunit; or d) an unaltered alpha subunit and an unaltered beta subunit.

The polypeptides or fusion proteins of the invention can be in isolated form or in the form of active conjugates or complexes thereof.

In this regard, a particular object of this invention resides in a conjugate comprising a CSF3R polypeptide variant or a fusion protein as defined above. The conjugate comprises at least one chemical group (covalently) coupled to the polypeptide, such as a label, stabilizer, toxin, drug, etc. In a particular embodiment, the conjugate comprises a molecule selected from radioactive labels, biotin, fluorescent labels, cytotoxic agents, drugs or drug delivery agents, covalently coupled to any amino acid residue of the CSF3R polypeptide variant. Useful conjugates can be generated using molecules and methods known per se in the art, for example for allowing the detection of the interaction with a ligand (radioactive or fluorescent labels, biotin), or improving the agents in terms of drug delivery efficacy, such as polyethylene glycol and other natural or synthetic polymers (Harris J M and Chess R B, 2003; Greenwald R B et al., 2003; Pillai 0 and Panchagnula R, 2001).

Another aspect of this invention is a receptor complex comprising a CSF3R polypeptide variant or a fusion protein or a conjugate as defined above. Such receptor complexes typically comprise a multimer formed between two or more fusion proteins of this invention, or between one or more fusion proteins of this invention and a distinct protein. Multimerization may be obtained through particular multimerization domain(s) contained in the proteins, as discussed supra. Such multimers may be formed in vitro, or they may form in vivo, upon administration to an organism.

Polypeptides and fusion proteins of this invention may be produced by any technique known per se in the art, such as by recombinant technologies, chemical synthesis, cloning, ligations, or combinations thereof.

In a particular embodiment, the polypeptides or fusion proteins are produced by recombinant technologies, e.g., by expression of a corresponding nucleic acid in a suitable host cell.

In this regard, the term "nucleic acid molecule" encompasses any nucleic acid molecule encoding a polypeptide or fusion protein as disclosed above. The nucleic acid may be a DNA (e.g., cDNA, gDNA, synthetic DNA, etc.), a RNA (e.g., mRNA), a PNA (peptide nucleic acid), etc., more preferably a DNA, even more preferably a cDNA molecule. A particular object of this invention resides more specifically in a nucleic acid molecule which comprises or consists of a nucleotide sequence selected from SEQ ID NO: 1, SEQ ID NO:3, SEQ ID NO:5, SEQ ID NO:7, SEQ ID NO: 11, or a complementary strand or degenerate sequence thereof.

The term "purified nucleic acid molecule" preferably refers to a nucleic acid molecule of the invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "purified nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use. In a preferred embodiment, genomic DNA are specifically excluded from the scope of the invention. Preferably, genomic DNA larger than 10 kbp (kilo base pairs), 50 kbp, 100 kbp, 150 kbp, 200 kbp, 250 kbp or 300 kbp are specifically excluded from the scope of the invention. Preferably, the "purified nucleic acid molecule" consists of cDNA only.

A degenerate sequence designates any nucleotide sequence encoding the same amino acid sequence as a reference nucleotide sequence, but comprising a distinct nucleotide sequence as a result of the genetic code degeneracy.

A further object of this invention is a vector comprising a nucleic acid molecule as defined above. The vector may be any cloning or expression vector, integrative or autonomously replicating, functional in any prokaryotic or eukaryotic cell. In particular, the vector may be a plasmid, cosmid, virus, phage, episome, artificial chromosome, and the like. The vector may comprise regulatory elements, such as a promoter, terminator, enhancer, selection marker, origin of replication, etc. Specific examples of such vectors include prokaryotic plasmids, such as pBR, pUC or pcDNA plasmids; viral vectors, including retroviral, adenoviral or AAV vectors; bacteriophages; baculoviruses; BAC or YAC, etc., as will be discussed below A further aspect of this invention is a recombinant host cell, wherein said cell comprises a nucleic acid molecule or a vector as defined above. The host cell may be a prokaryotic or eukaryotic cell. Examples of prokaryotic cells include bacteria, such as E. coli. Examples of eukaryotic cells are yeast cells, plant cells, mammalian cells, including any primary cell culture or established cell line (e.g., 3T3, Vero, HEK293, TN5, etc.). Particularly preferred mammalian cells of the present invention are CHO cells.

Another object of this invention is a method of producing a CSF3R polypeptide variant or fusion protein as defined above, the method comprising culturing a recombinant host cell of the invention under conditions allowing expression of the nucleic acid molecule, and recovering the polypeptide produced. The polypeptide may be recovered from the cell culture supernatant, if the polypeptide is secreted, or from the cell cytoplasm or debris, if suitable. The polypeptide product may be glycosylated or not, or contain other post-translational modifications depending on the host cell used. Preferred glycosylation sites reside at amino acid 51, 93, 128, 134, 389, 474, 579, 610 of SEQ ID NO: 10.

Many books and reviews provide teachings on how to clone and produce recombinant proteins using vectors and prokaryotic or eukaryotic host cells, such as some titles in the series "A Practical Approach" published by Oxford University Press ("DNA Cloning 2: Expression Systems", 1995; "DNA Cloning 4: Mammalian Systems", 1996; "Protein Expression", 1999; "Protein Purification Techniques", 2001).

In general, the vectors can be episomal or non-/homologously integrating vectors, which can be introduced in the appropriate host cells by any suitable means (transformation, transfection, conjugation, protoplast fusion, electroporation, calcium phosphate-precipitation, direct microinjection, etc.) to transform them. Factors of importance in selecting a particular plasmid, viral or retroviral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. The vectors should allow the expression of the polypeptide or fusion proteins of the invention in prokaryotic or eukaryotic host cells, under the control of appropriate transcriptional initiation/termination regulatory sequences, which are chosen to be constitutively active or inducible in said cell. A cell line substantially enriched in such cells can be then isolated to provide a stable cell line.

A particularly preferred method of high-yield production of a recombinant polypeptide of the present invention is through the use of dihydrofolate reductase (DHFR) amplification in DHFR-deficient CHO cells, by the use of successively increasing levels of methotrexate as described in U.S. Pat. No. 4,889,803. The polypeptide obtained may be in a glycosylated form.

For eukaryotic host cells (e.g. yeasts, insect or mammalian cells), different transcriptional and translational regulatory sequences may be employed, depending on the nature of the host. They may be derived form viral sources, such as adenovirus, papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated. The cells which have been stably transformed by the introduced DNA can be selected by also introducing one or more markers which allow for selection of host cells which contain the expression vector. The marker may also provide for phototrophy to an auxotrophic host, biocide resistance, e.g. antibiotics, or heavy metals such as copper, or the like. The selectable marker gene can be either directly linked to the DNA sequences to be expressed (e.g., on the same vector), or introduced into the same cell by co-transfection. Additional elements may also be needed for optimal synthesis of proteins of the invention.

Particularly suitable prokaryotic cells include bacteria (such as Bacillus subtilis or E. coli) transformed with a recombinant bacteriophage, plasmid or cosmid DNA expression vector. Such cells typically produce proteins comprising a N-terminal Methionine residue, such proteins representing particular objects of this invention. Preferred cells to be used in the present invention are eukaryotic host cells, e.g. mammalian cells, such as human, monkey, mouse, and Chinese Hamster Ovary (CHO) cells, because they provide post-translational modifications to protein molecules, including correct folding or glycosylation at correct sites. Alternative eukaryotic host cells are yeast cells (e.g., *Saccharomyces, Kluyveromyces*, etc.) transformed with yeast expression vectors. Also yeast cells can carry out post-translational peptide modifications including glycosylation. A number of recombinant DNA strategies exist which utilize strong promoter sequences and high copy number of plasmids that can be utilized for production of the desired proteins in yeast. Yeast cells recognize leader sequences in cloned mammalian gene products and secrete polypeptides bearing leader sequences (i.e., prepeptides).

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type. A cell line substantially enriched in such cells can be then isolated to provide a stable cell line.

Mammalian cell lines available as hosts for expression are known in the art and include many immortalised cell lines available from the American Type Culture Collection (ATCC) including, but not limited to, Chinese hamster ovary (CHO), HeLa, baby hamster kidney (BHK), monkey kidney (COS), C127, 3T3, BHK, HEK 293, Bowes melanoma and human hepatocellular carcinoma (for example Hep G2) cells and a number of other cell lines. In the baculovirus system, the materials for baculovirus/insect cell expression systems are commercially available in kit form from, inter alia, Invitrogen.

In addition to recombinant DNA technologies, the polypeptides or fusion proteins of this invention may be prepared by chemical synthesis technologies. Examples of chemical synthesis technologies are solid phase synthesis and liquid phase synthesis. As a solid phase synthesis, for example, the amino acid corresponding to the carboxy-terminus of the polypeptide to be synthesised is bound to a support which is insoluble in organic solvents and, by alternate repetition of reactions (e.g., by sequential condensation of amino acids with their amino groups and side chain functional groups protected with appropriate protective groups), the polypeptide chain is extended. Solid phase synthesis methods are largely classified by the tBoc method and the Fmoc method, depending on the type of protective group used. Totally synthetic proteins of size comparable to that of CSF3R are disclosed in the literature (Brown A et al., 1996).

The polypeptides of the present invention can be produced, formulated, administered, or generically used in other alternative forms that can be preferred according to the desired method of use and/or production. The proteins of the invention can be post-translationally modified, for example by glycosylation. The polypeptides or proteins of the invention can be provided in isolated (or purified) active form, or as precursors, derivatives and/or salts thereof.

As indicated above, the term "active" or "biologically active" means that such polypeptides have the capacity to bind a CSF3R ligand and function as a CSF3R agonist or antagonist. A "biologically active" polypeptide of the present invention is as well one that shows activity in at least one of the assays mentioned above.

"Precursors" are compounds which can be converted into the polypeptides of present invention by metabolic and/or enzymatic processing prior to or after administration thereof to cells or an organism.

The term "salts" herein refers to both salts of carboxyl groups and to acid addition salts of amino groups of the polypeptides of the present invention. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Any of such salts should have substantially similar activity to the polypeptides of the invention.

The term "derivatives" as used herein refers to derivatives that can be prepared from the functional groups present on the lateral chains of the amino acid moieties or on the amino-/or carboxy-terminal groups according to methods known per se in the art. Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups.

Purification of the polypeptides or fusion proteins of the invention can be carried out by a variety of methods known per se in the art, such as, without limitation, any conventional procedure involving extraction, precipitation, chromatography, electrophoresis, or the like. A particular purification procedure is affinity chromatography, using (monoclonal) antibodies or affinity groups which selectively bind the polypeptide and which are typically immobilized on a gel matrix contained within a column. Purified preparations of the proteins of the invention, as used herein, refers to preparations which contain less than 15% of contaminants, more preferably which comprise at least 90, 95 or 97% of the polypeptide. An isolated protein, polypeptide or nucleic acid denotes a protein, polypeptide or nucleic acid which is not in its natural environment.

Polypeptides of the invention are useful on their own, as components of fusion proteins such as Fc fusion, and/or in combination with another agent. Preferably, the Fc fusion comprises SEQ ID NO:4 or SEQ ID NO:8.

Preferably the agent is selected among interferon-beta, CSF3, GM-CSF, tissue-plasminogen activator, hematopoietic factor, soluble NgR members (e.g. Nogo-66), antagonists (e.g. antibodies) targeted to NgR, antagonists (e.g. antibodies) targeted to myelin inhibitors (e.g. Nogo, MAG or Omgp), steel factor (SF, Kit ligand), Flt3/Flk2 ligand (FL), RhoA blockers, Rho blockers, ROCK blockers, sodium channel blockers, growth-related proteins such as BDNF, VEGF, erythropoietin (EPO), neurotrophin-3 (NT-3) or GAP-43, β-secretase modulators, CXCL10, agonists of serotonin receptors (e.g. 5-HT1A/2A/7), LIF, EGFR blockers such as Erlotinib, and/or methylprednisolone. Particularly preferred is interferon-beta.

Several combinations might be envisaged: 1) combining a polypeptide of the present invention with T cell activation inhibitors such as the anti-CD3 Ab; 2) combining a polypeptide of the present invention with other hemopoietic factors, such as Flt3-L, either separated or combined in a chimeric molecule (progenipoietin); 3) sorting a particular cellular subset induced by a polypeptide of the present invention, which may provide protection against autoimmune and alloreactive responses; and 4) sorting a particular cellular subset mobilized by a combination of growth factors, including G-CSF, and a polypeptide of the present invention, (e.g. particular subsets of immature hemopoietic progenitor cells, mobilized by a combination of growth factors, including G-CSF and a polypeptide of the present invention, might have the capacity to halt the onset of overt diabetes).

A further object of this invention is a pharmaceutical composition comprising a product (e.g., a polypeptide, fusion protein, conjugate, receptor complex, nucleic acid molecule, vector or cell) as defined above, and a pharmaceutically acceptable carrier or diluent. More preferred pharmaceutical compositions of this invention comprise a polypeptide comprising SEQ ID NO:4 or SEQ ID NO:8, or a fusion protein comprising such a polypeptide.

Another aspect of this invention relates to the use of a product (e.g., a polypeptide, fusion protein, conjugate, receptor complex, nucleic acid molecule, vector or cell) as disclosed above, for the manufacture of a pharmaceutical composition for treating a human subject.

GCSF is typically used for the treatment of different kinds of neutropenia in humans. It is one of the few growth factors approved for clinical use. In particular, it is used to reduce chemotherapy (CT)-induced cytopenia (Viens et al., J. of Clin. Oncology, Vol. 20, No. 1, 2002: 24-36). GCSF has also been implicated for therapeutic use in infectious diseases as potential adjunctive agent (Hubel et al., J. of Infectious Diseases, Vol. 185: 1490-501, 2002).

Agonists of CSF3 used in therapy are known. For example, Amgen Inc has launched pegfilgrastim, a pegylated form of recombinant CSF3, for the treatment of chemotherapy-induced neutropenia or leukopenia. Bolder Biotechnology developed a fusion protein comprising pegylated CSF3 linked to IgG-Fc called BBT-001 for the treatment of leukopenia. Chugai Pharmaceutical launched lenograstim, a recombinant human CSF3, for the treatment of leukopenia, haematological disease, immune disorder, neutropenia, and viral infection. Dragon Pharmaceuticals developed a formulation of CSF3 for the treatment of leukopenia. Kancer limited developed an oral formulation of CSF3 for the treatment of leukopenia. Kyowa Hakko Kogyo Co Ltd launched nartograstim (injectable CFS3) for the treatment of anemia or leukopenia. Neose Technologies developed a longer-acting glycopegylated CSF3 for the treatment of neutropenia. Transkaryotic Therapies Inc developed a gene-activated CSF3 (GA-GCSF) for the treatment of neutropenia.

In a mouse model of myocardial infarction, CSF3 treatment did not affect initial infarct size at day 3 but improved cardiac function as early as 1 week postinfarction, and the beneficial effects were reduced by delayed start of treatment (Harada et al. Nature Med. Vol. 11: 305-311, 2005). CSF3 induced antiapoptotic proteins and inhibited apoptotic death of cardiomyocytes, and CSF3 also reduced apoptosis of endothelial cells and increased vascularization in the infarcted hearts. Harada et al. suggested that CSF3 promotes survival of cardiac myocytes and prevents left ventricular remodeling after myocardial infarction through functional communication between cardiomyocytes and noncardiomyoctes.

Application of a single dose of G-CSF in patients with community-acquired pneumonia (CAP) caused a prolonged survival and increased activation of neutrophils combined with a sustained release of anti-inflammatory cytokines (Droemann et al. Respiration. 2005 Dec. 12. Epub ahead of print).

CSF3 is also beneficial in animals for the prevention and/or treatment of immune-mediated diseases, e.g. graft-vs-host disease, multiple sclerosis, systemic lupus erythematosus, inflammatory bowel disease, and diabetes (Rutella et al. J. Immunol. 2005 Dec. 1; 175(11):7085-91).

In graft-vs-host disease, the in vitro alloresponse of donor cells 5 days after G-CSF administration might be predictive of the occurrence of acute GVHD in transplanted patients, and T cells from donors with a significant G-CSF-induced suppression of in vitro alloreactivity less frequently induce GVHD in the recipients. The production of TGF-β after allogeneic HSC transplantation might provide an additional explanation for the opposing effects of G-CSF administration to donors on acute vs chronic GVHD. In this respect, G-CSF administration to donor mice might induce TGF-β- and IL-10-dependent protection from acute GVHD but contribute to TGF-β-dependent exacerbation of chronic GVHD. Neutralization of TGF-β in transplanted mice protects from chronic GVHD in gastrointestinal tract and skin but not from liver abnormalities.

In inflammatory bowel disease, G-CSF has been successfully used in experimental colitis in White New Zealand rabbits. Animals were pretreated either 24 h before or at colitis induction either with 50 or 200 μg/kg rG-CSF. Cytokine administration at either dose translated into increased tissue myeloperoxidase levels, despite a histologically similar mucosal polymorphonuclear cell infiltrate in the G-CSF-treated compared with the control colitis group. Moreover, dialysis fluid levels of leukotriene B4 and thromboxane B2 were significantly lower in treated animals. Similar results were obtained in the 2,4,6-trinitrobenzene sulfonic acid colitis in rats, a model of Th1 disease. G-CSF at 250 μg/kg/day remarkably attenuated both the loss of body weight and colonic wall thickening due to progressive transmural inflammation. This effect was associated with a significant inhibition of IFN-7 and IL-12p35 transcription. Preclinical data have been translated also into the treatment of human inflammatory bowel disease. G-CSF proved to be efficacious in severe endoscopic postoperative recurrence of Crohn's disease. Five patients were treated with 300 μg of recombinant human G-CSF three times per week for 12 wk. G-CSF was safe and well tolerated, and a significant increase in neutrophil counts, IL-1ra, and soluble TNFR p55 and p75 was shown in the plasma of G-CSF-treated patients. In an open-labeled study, G-CSF demonstrated safety and efficacy for the treatment of active Crohn's disease. Patients received 300 μg of G-CSF for 12 consecutive weeks, achieving a statistically significant decrease in disease activity. These studies suggest that rG-CSF might be a promising therapeutic approach for Crohn's disease.

The anti-inflammatory properties of G-CSF and its capacity to switch T cell cytokine profiles toward Th2 and to promote tolerogenic DC and Treg cell differentiation prompted its therapeutic evaluation in experimental models of autoimmune diseases such as systemic lupus erythematosus (SLE) and rheumatoid arthritis (RA). Nephritis, the end-stage of lupus disease of which inflammation is the hallmark, was prevented in mice given a high-dose G-CSF regimen (200 μg/kg), even when treatment was started in animals already suffering from a beginning proteinuria An uncoupling between immune complex deposition and kidney damage was observed, which corresponded to a profoundly reduced expression of FcγRIII (CD16) within the glomeruli, a receptor mediating the inflammatory response of kidney mesangial cells to Igs. Accordingly, inflammatory IL-12 serum response was limited, and mortality was delayed significantly. In inflammatory arthritis, neutralization of endogenous G-CSF markedly reduced the progression of disease to the same extent as anti-TNF treatment. Cell therapy with G-CSF-mobilized hemopoietic progenitor cells, devoid of other G-CSF-induced proinflammatory cell subsets, may show therapeutic promise in patients with autoimmune diseases.

Beneficial effects of G-CSF in T cell-dependent animal models of multiple sclerosis (MS) and type 1 autoimmune diabetes (T1D) proved to be of potential interest for translation into therapeutic strategies. A short 7-day treatment with G-CSF (200 μg/kg), initiated at the onset of clinical signs, conferred durable protection of SJL:J mice against myelin basic protein-induced experimental autoimmune encephalomyelitis. Protected mice displayed limited demyelination and reduced recruitment of T cells to the CNS as well as very discrete autoimmune inflammation and barely detectable cytokine and chemokine mRNA levels in the CNS. These effects were based on immunoregulatory events that took place in the periphery and included an imbalance in the chemokine (MIP-1α/MCP-1, e.g., CCL3/CCL2) production ratio by macrophages and autoreactive lymphocytes, which correlated with an immune deviation of the autoreactive response toward Th2. A dramatic reduction of systemic and lymphocyte TNF-α production was also observed. The protective effect of G-CSF was confirmed in C57BL/6 mice immunized with the MOG peptide. Elevated G-CSF gene expression occurred selectively in brain lesions of patients at the acute phase of MS, suggesting an endogenous protective role of the growth factor.

Thus, in another embodiment of the present invention, a polypeptide of the present invention, alone and/or in combination with one or more additional factors can be used to treat multiple sclerosis (MS) and/or provide prophylactic neuroprotective therapy in multiple sclerosis patients. This is based on the presence of the GCSF receptor on oligodendrocytes, supporting a direct efficacy of GCSF on the primary target cells of MS. In addition, the GCSF receptor is present on nerve cells and their processes, which are compromised at later stages of the disease, and could correlate with lasting disabilities (Cid. et al. (2002), J Neurol Sci, 193, 103-9). Even areas in the brain that appear normal with regard to white matter changes show signs of neurodegeneration. Axonal pathology and neurodegeneration therefore are important therapeutic targets in Multiple Sclerosis. GCSF with its antiapoptotic activity in neurons and its pro-regenerative potential (by enhancing neurogenesis and plasticity) supports that the compositions described herein can be used as new therapies for treating Multiple Sclerosis.

Furthermore, pathophysiological mechanisms in multiple sclerosis overlap with important mechanisms in cerebral ischemia, e.g. the involvement of nitric oxide (Smith, et al. (2001), Ann Neurol, 49, 470-6), and involvement of glutamate excitotoxicity (Pitt et al. (2000), Nat Med, 6, 67-70). In light of this information, a polypeptide of the present invention is a novel treatment option for multiple sclerosis which while not being bound to any particular mechanism or theory protects neurons directly as opposed to common treatments which reduce inflammation.

Results demonstrating the capacity of G-CSF to counteract acute neuronal degeneration and to drive neurogenesis in acute ischemia indicate that G-CSF is a promising drug for stroke, behavioural improvements, degenerative, and autoimmune diseases of the nervous system (Schneider et al. J Clin Invest. 2005 August; 115(8):2083-98; Schneider et al. Cell Cycle. 2005 December; 4(12):1753-7.US2005/0142102). CSF3R has an astonishingly broad, predominantly neuronal expression pattern in the CNS. G-CSF was shown to be neuroprotective in 2 different models of focal cerebral ischemia, with transient activation of STAT3 and ERK1/2 and a strong lasting activation of ERK5, which has been implicated in promoting neuronal survival as well of PI3K/Akt pathway activation implicated in the antiapoptotic activity of G-CSF. The most striking effect of peripherally administered G-CSF on the brain was seen in the dentate gyrus, where G-CSF increased the number of newly generated neurons under ischemic conditions but also in nonischemic, sham-operated animals. It is therefore intriguing to speculate that G-CSF may enhance structural repair and function even in healthy subjects or at long intervals after stroke. The broad array of data from different laboratories underlines the very stable neuroprotective and pro-regenerative effect of G-CSF in various stroke models. G-CSF might also be suitable as supportive treatment in rehabilitation phases after stroke. A predominant role of G-CSF in survival and differentiation of progenitor cells in the postischemic brain is also suggested. The cortical photothrombosis model used by Schneider et al. has the most prominent impact on sensorimotor behavior, which was also measured in the test battery performed, whereas hippocampal formation is most frequently linked to learning and memory processes. However, there is also a wealth of data supporting a possible role of the hippocampus in functional recovery from motor deficits. It was suggested that G-CSF-induced increase in hippocampal neurogenesis directly impacts recovery from cortical lesion-induced sensorimotor deficits. Thus, G-CSF signaling appears to be a novel protective system in the brain that is involved in counteracting acute neurodegeneration and regulating the formation of new neurons.

Neurogenesis is one mechanism that can lead to increased plasticity of neural networks, and can replace gradual loss of neurons. Therefore, one embodiment of the present invention is to provide enhancement, improvement or an increase in cognitive ability to an individual suffering from, displaying, and/or believed to some level of cognitive loss by administering one or more compositions as described herein to the individual in accordance with the administration discussion herein. In an alternative embodiment, cognitive enhancement may also benefit those individuals even useful under non-pathological conditions, e.g., those individuals who do not present with cognitive impairment.

Determining cognitive ability and therefore enhancement is known by one of skill in the art. Where increases or enhancement of cognitive ability are measured, they are compared before administration of the compositions of the invention and after the administration (and can also be measured during the administration in some embodiments) using the same test, e.g., with same criteria, parameters, etc.

In addition, the use of compositions according to the invention in cognition enhancement is not limited to a non-pathological decline in mental capacity, but can also be applied to boosting the normal, physiological repertoire of mental capabilities, for example memory enhancement, enhancement of fine motor coordination, and/or enhancement of logical capabilities.

G-CSF also provided protection against experimental autoimmune diabetes in NOD mice. G-CSF (200 μg/kg) reversed the accelerating effects of cyclophosphamide, prevented the loss of $CD4^+CD25^+$ Treg cells and abrogated the robust cytokine—particularly IFN-γ—and chemokine burst triggered in immune cells by cyclophosphamide. In the spontaneous diabetes model, treatment of NOD mice at 4 wk of age for 5 consecutive days, repeated every 4 wk thereafter until 16 wk of age, durably prevented disease onset and destructive insulitis. This protection correlated with marked recruitment of two major regulatory subsets, i.e., plasmacytoid DCs and CD4$^+$CD25$^+$ Treg cells. Moreover, G-CSF recipients displayed an accumulation, particularly at the peripancreatic lymph nodes, of CD4$^+$CD25$^+$ Treg cells, which produced high levels of TGF-$\beta$1 and remained functional, actively suppressing diabetes transfer in secondary NOD-SCID recipients. Sorted DCs from mice given a single 5-day-long G-CSF treatment, relative to DCs from excipient-treated donors, were able upon adoptive transfer to secondary NOD recipients to trigger markedly enhanced accumulation of CD4$^+$CD25$^+$ Treg cells that expressed significantly higher levels of membrane TGF-$\beta$1. Endogenous response factors to infections such as G-CSF may be involved in protection against T1D onset provided by infectious events, particularly if they take place in early phases of diabetes development.

Activity of a polypeptide of the present invention in the above-mentioned diseases can be similarly demonstrated.

CD4$^+$CD25$^+$ Treg cells mobilized by G-CSF might represent a promising source of Treg cells for clinical application since they can be expanded up to 40.000-fold with artificial APCs and high-dose IL-2. Similarly, a polypeptide of the present invention may mobilize CD4$^+$CD25$^+$ Treg cells.

Thus, CSF3 has been implicated in the following diseases: graft-vs-host disease, cancer, neutropenia, neurological disorders or conditions, pneumonia, autoimmune diseases, haematological diseases, hemopoietic disorders, infectious diseases, inflammatory bowel disease, and diabetes.

Neurological conditions that can be treated according to the present invention can be generally classified into three classes: those disease with ischemic or hypoxic mechanisms herein named ischemic-related diseases; neurodegenerative diseases (see Adams et al, Principles of Neurology, 1997, 6.sup.th Ed., New York, pp 1048 ff); and neurological and psychiatric diseases associated with neural cell death. Other neurological conditions that can be treated according to the present invention also include enhancing cognitive ability and the treatment of brain tumors, such as glioblastomas, astrocytomas, meningiomas, and neurinomas. Examples of neurological and psychiatric diseases associated with neural cell death include septic shock, intracerebral bleeding, subarachnoidal hemorrhage, multiinfarct dementia, inflammatory diseases (such as vasculitis, multiple sclerosis, and Guillain-Barre-syndrome), neurotrauma (such as spinal cord trauma, and brain trauma), peripheral neuropathies, polyneuropathies, epilepsies, schizophrenia, depression, metabolic encephalopathies, and infections of the central nervous system (viral, bacterial, fungal).

Diseases with ischemic or hypoxic mechanisms, herein named ischemic-related diseases, can be further subclassified into general diseases and cerebral ischemia. Examples of such general diseases involving ischemic or hypoxic mechanisms include myocardial infarction, cardiac insufficiency, cardiac failure, congestive heart failure, myocarditis, pericarditis, perimyocarditis, coronary heart disease (stenosis of coronary arteries), angina pectoris, congenital heart disease, shock, ischemia of extremities, ischemic injury, stenosis of renal arteries, diabetic retinopathy, thrombosis associated with malaria, artificial heart valves, anemias, hypersplenic syndrome, emphysema, lung fibrosis, and pulmonary edema. Examples of cerebral ischemia disease include stroke (as well as hemorrhagic stroke), cerebral microangiopathy (small vessel disease), intrapartal cerebral ischemia, cerebral ischemia during/after cardiac arrest or resuscitation, cerebral ischemia due to intraoperative problems, cerebral ischemia during carotid surgery, chronic cerebral ischemia due to stenosis of blood-supplying arteries to the brain, sinus thrombosis or thrombosis of cerebral veins, cerebral vessel malformations, and diabetic retinopathy.

Examples of neurodegenerative diseases include amyotrophic lateral sclerosis (ALS), Parkinson's disease, Huntington's disease, Wilson's disease, multi-system atrophy, Alzheimer's disease, Pick's disease, Lewy-body disease, Hallervorden-Spatz disease, torsion dystonia, hereditary sensorimotor neuropathies (HMSN), Gerstmann-Strussler-Schanker disease, Creutzfeld-Jakob-disease, Machado-Joseph disease, Friedreich ataxia, Non-Friedreich ataxias, Gilles de la Tourette syndrome, familial tremors, olivopontocerebellar degenerations, paraneoplastic cerebral syndromes, hereditary spastic paraplegias, hereditary optic neuropathy (Leber), retinitis pigmentosa, Stargardt disease, and Kearns-Sayre syndrome. More preferably, the neurodegenerative disease is multiple sclerosis.

Preferably, the graft-vs-host disease is acute GVHD or chronic GVHD. More preferably, the graft-vs-host disease is acute GVHD. An agonist of CSF3 is useful for acute GVHD and an antagonist of CSF3 is useful for chronic GVHD.

Preferably, the inflammatory bowel disease is colitis or Crohn's disease (e.g. severe endoscopic postoperative recurrence of Crohn's disease or active Crohn's disease).

Preferably, the autoimmune disease is an autoimmune disease of the nervous system, systemic lupus erythematosus (SLE), osteoarthritis, or rheumatoid arthritis (RA).

Preferably, diabetes is a type 1 autoimmune diabetes (T1D).

Preferably, the pneumonia is a community-acquired pneumonia (CAP).

Preferably, the neutropenia is a severe congenital neutropenia, chemotherapy (CT)-induced cytopenia, leukopenia.

Preferably, the cancer is malignant disorders of myeloid lineages such as acute myeloblastic leukaemia (AML), leukemia, leukemogenesis, myelodysplastic syndromes, myeloid leukemia, acute lymphocytic leukemia (ALL), acute leukemia, chronic myeloid leukemia (CML), solid tumor, ovarian epithelial carcinoma, neoplasms, cancer of bladder, carcinoma, cancer of prostate, squamous cell carcinoma, melanoma, or colorectal cancer.

Preferably, the haematological disease is a myocardial infarction.

Accordingly, one object of the present invention is to provide a method of treating one or more of the above-mentioned diseases in a mammal by administering to the mammal a polypeptide of the present invention, derivatives thereof, mimetics thereof, fusion proteins thereof, and combinations thereof, or cells secreting these factors, to treat the condition.

The above products and pharmaceutical composition are thus suited, for instance, for treating graft-vs-host disease, cancer, neutropenia, neurological disorders or conditions, pneumonia, autoimmune diseases, haematological diseases, hemopoietic disorders, infectious diseases, inflammatory bowel disease, and diabetes.

Another object of the present invention is to provide a method of treating a neurological condition in a mammal, by conditioning a neural stem cell composition with a polypeptide of the present invention, derivatives thereof, mimetics thereof and combinations thereof, and subsequently administering the neural stem cells to a mammal for the treatment of the condition.

Another object of the present invention is to provide a method of treating a neurological condition in a mammal by administering to the mammal a polypeptide of the present invention to treat a neurological condition.

Another object of the present invention is to provide a method of enhancing the survival of a cell transplanted into a mammal, by introducing into the cell one or more polynucleotides which encode a polypeptide of the present invention, derivatives thereof, mimetics thereof and/or combinations thereof prior to transplanting the cell into the mammal, whereby the cell expresses a polypeptide of the present invention in an amount sufficient to enhance the survival of the cell relative to the cell survival prior to the introduction of the polynucleotides.

Another object of the present invention is to provide a method of enhancing the viability of a neural cell culture by providing a polypeptide of the present invention, derivatives thereof, mimetics thereof, fusion proteins thereof and/or combinations thereof to enhance the viability of the neural cell culture relative to the culture prior to providing the hematopoietic factor. In such a method, the polypeptide of the present invention can be used to contact the cells of the culture or may be provided using polynucleotides that encode and express the polypeptide of the present invention.

Another object of the present invention is to provide a method to treat a neurological condition such as trinucleotide repeated disorder, a peripheral neuropathy, a lysosomal storage disease, a Parkinsonism or a Glaucoma with a polypeptide of the present invention or fusion protein thereof.

The invention also encompasses a method of enhancing the interaction between CSF3R and a ligand thereof in a subject, the method comprising administering to the subject an effective amount of a product as defined above.

The invention also encompasses a method of reducing the interaction between CSF3R and a ligand thereof in a subject, the method comprising administering to the subject an effective amount of a product as defined above.

Within the context of the present invention, the term treatment includes preventive or curative treatments in a subject, particularly a human subject. Treatment includes any amelioration of a clinical manifestation of a disease, delaying the onset of a disease, particularly the onset of an acute disease; reducing its severity, reducing progression of the disease or suppressing the cause(s) thereof.

Effective doses may be adjusted by the skilled artisan, depending on the patient, disease and product. Typically, effective doses are comprises between about 5 µg/kg and 50 mg/kg, particularly between 100 µg/kg and 10 mg/kg.

The pharmaceutical compositions may contain one or more product(s) of this invention, either as the sole active ingredient or for use in combination with other active ingredient, and any suitable pharmaceutically acceptable diluents, carriers, biologically compatible vehicles and additives which are suitable for administration to an animal (for example, physiological saline solution) and optionally comprising auxiliaries (like excipients, stabilizers, or adjuvants) which facilitate the processing of the active compounds into preparations which can be used pharmaceutically. The pharmaceutical compositions may be formulated in any acceptable way to meet the needs of the mode of administration. For example, the use of biomaterials and other polymers for drug delivery, as well the different techniques and models to validate a specific mode of administration, are disclosed in literature (Luo B and Prestwich G D, 2001; Cleland J L et al., 2001).

"Pharmaceutically acceptable" is meant to encompass any carrier, which does not interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringer's solution. Carriers can be selected also from starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the various oils, including those of petroleum, animal, vegetable or synthetic origin (peanut oil, soybean oil, mineral oil, sesame oil).

Any accepted mode of administration can be used and determined by those skilled in the art to establish the desired blood levels of the active ingredients. For example, administration may be by various parenteral routes such as subcutaneous, intravenous, intradermal, intramuscular, intraperitoneal, intranasal, transdermal, rectal, oral, or buccal routes. The pharmaceutical compositions of the present invention can also be administered in sustained or controlled release dosage forms, including depot injections, osmotic pumps, and the like, for the prolonged administration of the polypeptide at a predetermined rate, preferably in unit dosage forms suitable for single administration of precise dosages.

Parenteral administration can be by bolus injection or by gradual perfusion over time. Preparations for parenteral administration include sterile aqueous or non-aqueous solutions, suspensions, and emulsions, which may contain auxiliary agents or excipients known in the art, and can be prepared according to routine methods. In addition, suspension of the active compounds as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyl oleate or triglycerides. Aqueous injection suspensions that may contain substances increasing the viscosity of the suspension include, for example, sodium carboxymethyl cellulose, sorbitol, and/or dextran. Optionally, the suspension may also contain stabilizers. Pharmaceutical compositions include suitable solutions for administration by injection, and contain from about 0.01 to 99.99 percent, preferably from about 20 to 75 percent of active compound together with the excipient.

It is understood that the dosage administered will be dependent upon the age, sex, health, and weight of the recipient, kind of concurrent treatment, if any, frequency of treatment, and the nature of the effect desired. The dosage will be tailored to the individual subject, as is understood and determinable by one of skill in the art. The total dose required for each treatment may be administered by multiple doses or in a single dose. The pharmaceutical composition of the present invention may be administered alone or in conjunction with other therapeutics directed to the condition, or directed to other symptoms of the condition. Usually a daily dosage of active ingredient is comprised between 0.01 to 100 milligrams per kilogram of body weight per day. Ordinarily 1 to 40 milligrams per kilogram per day given in divided doses or in sustained release form is effective to obtain the desired results. Second or subsequent administrations can be performed at a dosage, which is the same, less than, or greater than the initial or previous dose administered to the individual.

A further aspect of this invention relates to compositions and methods for detecting or dosing a polypeptide or nucleic acid of this invention in a sample. Such compositions include, for instance, any specific ligand of a polypeptide of this invention, such as an antibody, or a fragment or derivative thereof, or any specific nucleic acid probes or primers.

In this regard, a further object of this invention is an antibody, or a fragment or derivative thereof, that selectively binds a CSF3R polypeptide variant as disclosed above. In a more specific embodiment, the antibody, fragment or derivative thereof selectively binds an epitope of the polypeptides of the present invention. Residues $His^4$, $Phe^{74}$, $Gln^{86}$, $Leu^{88}$, and $Gln^{90}$ of SEQ ID NO:4 were found to be important for receptor function, with $Gln^{87}$ being the most important (Layton et al.). Thus, preferred epitopes consist of epitopes comprising these residues, in particular $Gln^{87}$. $Phe^{74}$, $Gln^{86}$ and $Gln^{90}$ of SEQ ID NO:4. These residues lie in the F and G β strands of anchored CSF3R. Layton et al. further disclosed a mAb LMM711, which was also on the F and G strands of the Ig-like domain, overlapping the CSF3 binding site, consistent with the strongly neutralizing effect of this mAb. Thus, a preferred epitope is one that comprises $Phe^{74}$, $Gln^{86}$ and $Gln^{90}$ of SEQ ID NO:4. The invention also relates to a pharmaceutical composition comprising an antibody, fragment or derivative thereof as defined above.

Preferred fragments of the Ig-like domain comprises or consists of residues $His^4$, $Phe^{74}$, $Gln^{86}$, $Leu^{88}$ and $Gln^{90}$ of SEQ ID NO:4. More preferred fragments of the Ig-like domain comprises or consists of residues $Phe^{74}$, $Gln^{86}$ and $Gln^{90}$ of SEQ ID NO:4. Alternatively, preferred fragments of the Ig-like domain comprises or consists of the F and G strands of the Ig-like domain.

Within the context of this invention, the term "selective" binding indicates that the antibodies preferentially bind the target polypeptide or epitope, i.e., with a higher affinity than any binding to any other antigen or epitope. In other words, binding to the target polypeptide can be discriminated from non-specific binding to other antigens.

The antibodies may be coupled to heterologous moieties, such as toxins, labels, drugs or other therapeutic agents, covalently or not, either directly or through the use of coupling agents or linkers.

Antibodies of this invention may be used for detecting, dosing, purifying or neutralizing CSF3R polypeptide variant of this invention. In a particular aspect, the invention thus resides in a method of detecting or dosing a CSF3R polypeptide variant as defined above in a sample, comprising contacting such a sample with an antibody, fragment or derivative thereof as disclosed above, and determining the formation or dosing the (relative) quantity of an immune complex. The sample may be for instance any biological fluid, such as blood, plasma, serum, etc., optionally diluted and/or treated. The antibody, fragment or derivative thereof may be in suspension or immobilized on a support. The presence or amount of immune complexes may be determined by any technique known per se in the art, e.g., by ELISA, RIA, etc., e.g., using reporter antibodies, labelled antibodies, etc.

Methods for producing antibodies, fragments or derivatives thereof are well known in the art, including immunization of an animal and collection of serum (polyclonal) or spleen cells (to produce hybridomas by fusion with appropriate cell lines). Methods of producing polyclonal antibodies from various species, including rodents, primates and horses, have been described for instance in Vaitukaitis et al. (J Clin Endocrinol Metab. 33 (1971) p. 988). Briefly, the antigen is combined with an adjuvant (e.g., Freund's adjuvant) and administered to an animal, typically by sub-cutaneous injection. Repeated injections may be performed. Blood samples are collected and immunoglobulins or serum are separated. Monoclonal antibodies to the CSF3R polypeptides of the invention can also be readily produced by one skilled in the art. The general methodology for making monoclonal antibodies using hybridoma technology is well known (see, for example, Kohler, G. and Milstein, C., Nature 256: 495-497 (1975); Kozbor et al., Immunology Today 4: 72 (1983); Cole et al., 77-96 in Monoclonal Antibodies and Cancer Therapy, Alan R. Liss, Inc. (1985); Antibodies: A laboratory Manual, CSH Press, 1988; Kohler et al Nature 256 (1975) 495). Briefly, these methods comprise immunizing an animal with the antigen, subsequently recovering spleen cells and fusing these cells with immortalized cells, such as myeloma cells, to produce hybridomas. Hybridomas producing the desired monoclonal antibodies can be selected by limit dilutions. Antibodies may also be produced by selection of combinatorial libraries of immunoglobulins, as disclosed for instance in Ward et al (Nature 341 (1989) 544).

Panels of monoclonal antibodies produced against the polypeptides of the first aspect of the invention can be screened for various properties, i.e., for isotype, epitope, affinity, etc. Monoclonal antibodies are particularly useful in purification of the individual polypeptides against which they are directed. Alternatively, genes encoding the monoclonal antibodies of interest may be isolated from hybridomas, for instance by PCR techniques known in the art, and cloned and expressed in appropriate vectors.

Chimeric antibodies, in which non-human variable regions are joined or fused to human constant regions (see, for example, Liu et al., Proc. Natl. Acad. Sci. USA, 84, 3439 (1987)), may also be of use.

The antibody may be modified to make it less immunogenic in an individual, for example by humanisation (see Jones et al., Nature, 321, 522 (1986); Verhoeyen et al., Science, 239, 1534 (1988); Kabat et al., J. Immunol., 147, 1709 (1991); Queen et al., Proc. Natl. Acad. Sci. USA, 86, 10029 (1989); Gorman et al., Proc. Natl. Acad. Sci. USA, 88, 34181 (1991); and Hodgson et al., Bio/Technology, 9, 421 (1991)). The term "humanised antibody", as used herein, refers to antibody molecules in which the CDR amino acids and selected other amino acids in the variable domains of the heavy and/or light chains of a non-human donor antibody have been substituted in place of the equivalent amino acids in a human antibody. The humanised antibody thus closely resembles a human antibody but has the binding ability of the donor antibody.

In a further alternative, the antibody may be a "bispecific" antibody, that is, an antibody having two different antigen binding domains, each domain being directed against a different epitope.

Phage display technology may be utilised to select genes which encode antibodies with binding activities towards the polypeptides of the invention either from repertoires of PCR amplified V-genes of lymphocytes from humans screened for possessing the relevant antibodies, or from naive libraries (McCafferty, J. et al., (1990), Nature 348, 552-554; Marks, J. et al., (1992) Biotechnology 10, 779-783). The affinity of these antibodies can also be improved by chain shuffling (Clackson, T. et al., (1991) Nature 352, 624-628).

Antibodies generated by the above techniques, whether polyclonal or monoclonal, have additional utility in that they may be employed as reagents in immunoassays, radioimmunoassays (RIA) or enzyme-linked immunosorbent assays (ELISA). In these applications, the antibodies can be labelled with an analytically-detectable reagent such as a radioisotope, a fluorescent molecule or an enzyme.

Polyclonal antibodies directed toward a polypeptide of the present invention generally are produced in animals (e.g., rabbits or mice) by means of multiple subcutaneous or intraperitoneal injections of the sCSF3R polypeptide and an adjuvant. It may be useful to conjugate a polypeptide of the present invention to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for anti-sCSF3R antibody titer.

Monoclonal antibodies directed toward a polypeptide of the present invention are produced using any method that provides for the production of antibody molecules by continuous cell lines in culture. Examples of suitable methods for preparing monoclonal antibodies include the hybridoma methods and the human B-cell hybridoma method. Also provided by the invention are hybridoma cell lines that produce monoclonal antibodies reactive with the sCSF3R polypeptide.

Monoclonal antibodies of the invention may be modified for use as therapeutics. One embodiment is a "chimeric" antibody in which a portion of the heavy (H) and/or light (L) chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, so long as they exhibit the desired biological activity.

In another embodiment, a monoclonal antibody of the invention is a "humanized" antibody. Generally, a humanized antibody has one or more amino acid residues introduced into it from a source that is non-human. Humanization can be performed, for example, using methods described in the art, by substituting at least a portion of a rodent complementarity-determining region for the corresponding regions of a human antibody.

The term "antibody" or "immunoglobulin" is intended to encompass both polyclonal and monoclonal antibodies. The preferred antibody is a monoclonal antibody reactive with the antigen. The term "antibody" is also intended to encompass mixtures of more than one antibody reactive with the antigen (e.g., a cocktail of different types of monoclonal antibodies reactive with the antigen). The term "antibody" is further intended to encompass whole antibodies, biologically functional fragments thereof, single-chain antibodies, and genetically altered antibodies such as chimeric antibodies comprising portions from more than one species, bifunctional antibodies, antibody conjugates, humanized and human antibodies. Biologically functional antibody fragments, which can also be used, are those peptide fragments derived from an antibody that are sufficient for binding to the antigen. Antibody as used herein is meant to include the entire antibody as well as any antibody fragments (e.g. F(ab').sub.2, Fab', Fab, Fv) capable of binding the epitope, antigen or antigenic fragment of interest.

By "purified antibody" is meant one which is sufficiently free of other proteins, carbohydrates, and lipids with which it is naturally associated. Such an antibody "preferentially binds" to sCSF3R polypeptides of the present invention (or an antigenic fragment thereof), i.e., does not substantially recognize and bind to other antigenically unrelated molecules. A purified antibody of the invention is preferably immunoreactive with and immunospecific sCSF3R of specific species and more preferably immunospecific for a native human sCSF3R.

By "binds specifically" is meant high avidity and/or high affinity binding of an antibody to a specific polypeptide i.e., sCSF3R. Antibody binding to its epitope on this specific polypeptide is preferably stronger than binding of the same antibody to any other epitope. Antibodies which bind specifically to sCSF3R may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g. by use of appropriate controls.

Preferably, the affinity is at least 1.5-fold, 2-fold, 5-fold 10-fold, 100-fold, $10^3$-fold, $10^4$-fold, $10^5$-fold or $10^6$-fold greater for a polypeptide of the invention than for other known members of the CSF3R family.

The term "genetically altered antibodies" means antibodies wherein the amino acid sequence has been varied from that of a native antibody. Because of the relevance of recombinant DNA techniques to this invention, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics.

The term "humanized antibody" or "humanized immunoglobulin" refers to an immunoglobulin comprising a human framework, at least one and preferably all complimentarily determining regions (CDRs) from a non-human antibody, and in which any constant region present is substantially identical to a human immunoglobulin constant region, i.e., at least about 85-90%, preferably at least 95% identical. Hence, all parts of a humanized immunoglobulin, except possibly the CDRs, are substantially identical to corresponding parts of one or more native human immunoglobulin sequences. See, e.g. Queen et al., U.S. Pat. Nos. 5,530,101; 5,585,089; 5,693, 762; and 6,180,370 (each of which is incorporated by reference in its entirety).

"Fully humanized antibodies" are molecules containing both the variable and constant region of the human immunoglobulin. Fully humanized antibodies can be potentially used for therapeutic use, where repeated treatments are required for chronic and relapsing diseases such as autoimmune diseases. One method for the preparation of fully human antibodies consist of "humanization" of the mouse humoral immune system, i.e. production of mouse strains able to produce human Ig (Xenomice), by the introduction of human immunoglobulin (Ig) loci into mice in which the endogenous Ig genes have been inactivated. The Ig loci are exceedingly complex in terms of both their physical structure and the gene rearrangement and expression processes required to ultimately produce a broad immune response. Antibody diversity is primarily generated by combinatorial rearrangement between different V, D, and J genes present in the Ig loci. These loci also contain the interspersed regulatory elements, which control antibody expression, allelic exclusion, class switching and affinity maturation. Introduction of unrearranged human Ig transgenes into mice has demonstrated that the mouse recombination machinery is compatible with human genes. Furthermore, hybridomas secreting antigen specific hu-mAbs of various isotypes can be obtained by Xenomice immunisation with antigen.

Fully humanized antibodies and methods for their production are known in the art (Mendez et al., Nature Genetics 15:146-156 (1997); Buggemann et al., Eur. J. Immunol. 21:1323-1326 (1991); Tomizuka et al., *Proc. Natl. Acad. Sci. USA* 97:722-727 (2000) Patent WO 98/24893.

The term "chimeric antibody" refers to an antibody in which the constant region comes from an antibody of one species (typically human) and the variable region comes from an antibody of another species (typically rodent). Hence, chimeric antibodies are molecules of which different portions are derived from different animal species, such as those having the variable region derived from a murine Mab and a human immunoglobulin constant region. Chimeric antibodies are primarily used to reduce immunogenicity in application and to increase yields in production, for example, where murine Mabs have higher yields from hybridomas but higher immunogenicity in humans, such that human/murine chimeric Mabs are used. Chimeric antibodies and methods for their production are known in the art (Cabilly et al., *Proc. Natl. Acad. Sci. USA* 81:3273-3277 (1984); Morrison et al., *Proc. Natl. Acad. Sci. USA* 81:6851-6855 (1984); Boulianne et al., *Nature* 312:643-646 (1984); Cabilly et al., European Patent Application 125023 (published Nov. 14, 1984); Neuberger et al., *Nature* 314:268-270 (1985); Taniguchi et al., European Patent Application 171496 (published Feb. 19, 1985); Morrison et al., European Patent Application 173494 (published Mar. 5, 1986); Neuberger et al., PCT Application WO 8601533, (published Mar. 13, 1986); Kudo et al., European Patent Application 184187 (published Jun. 11, 1986); Sahagan et al., *J. Immunol.* 137:1066-1074 (1986); Robinson et al., International Patent Application No. WO8702671 (published May 7, 1987); Liu et al., *Proc. Natl. Acad. Sci. USA* 84:3439-3443 (1987); Sun et al., *Proc. Natl. Acad. Sci. USA* 84:214-218 (1987); Better et al., *Science* 240:1041-1043 (1988); Riechmann et al., *Nature* 332:323-327. and Harlow and Lane, ANTIBODIES: A LABORATORY MANUAL, supra. These references are entirely incorporated herein by reference.

As used herein, the phrase "antibody fragment" refers to a molecule comprising a portion of an antibody capable of specifically binding an antigen, an antigenic determinant or an epitope. It will be appreciated that Fab and F(ab')2 and other fragments of the antibodies useful in the present invention may be used for the detection and quantitation of their antigens according to the methods disclosed herein for intact antibody molecules. Such fragments are typically produced by proteolytic cleavage, using enzymes such as papain (to produce Fab fragments) or pepsin (to produce F(ab')2 fragments).

As regards the antibodies mentioned herein throughout, the term "monoclonal antibody" is meant to include monoclonal antibodies, chimeric antibodies, fully humanized antibodies, antibodies to anti-idiotypic antibodies (anti-anti-Id antibody) that can be labeled in soluble or bound form, as well as fragments thereof provided by any known technique, such as, but not limited to enzymatic cleavage, peptide synthesis or recombinant techniques. A monoclonal antibody contains a substantially homogeneous population of antibodies specific to antigens, which populations contain substantially similar epitope binding sites. Mabs may be obtained by methods known to those skilled in the art. See, for example Kohler and Milstein, Nature, 256:495-497 (1975); U.S. Pat. No. 4,376, 110; Ausubel et al., eds., Harlow and Lane ANTIBODIES: A LABORATORY MANUAL, Cold Spring Harbor Laboratory (1988); and Colligan et al., eds., Current Protocols in Immunology, Greene Publishing Assoc. and Wiley Interscience N.Y., (1992-1996), the contents of which references are incorporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of Mabs in vivo or in situ makes this the presently preferred method of production. The term "monoclonal antibody" is also meant to include both intact molecules as well as fragments thereof, such as, for example, Fab and F(ab')2, which are capable of binding antigen. Fab and F(ab')2 fragments lack the Fc fragment of intact antibody, clear more rapidly from the circulation, and may have less non-specific tissue binding than an intact antibody (Wahl et al., *J. Nucl. Med.* 24:316-325 (1983)).

A monoclonal antibody is said to be "capable of binding" a molecule if it is capable of specifically reacting with the molecule to thereby bind the molecule to the antibody.

An "antigen" is a molecule or a portion of a molecule capable of being bound by an antibody, which antigen is additionally capable of inducing an animal to produce antibody capable of binding to an epitope of that antigen. An antigen may have one or more than one epitope. The specific reaction referred to above is meant to indicate that the antigen will react, in a highly selective manner, with an epitope on its corresponding antibody and not with the multitude of other antibodies which may be evoked by other antigens.

The antibodies, including fragments of antibodies, useful in the present invention may be used to quantitatively or qualitatively detect their antigens in a sample or to detect presence of cells that express their antigens. This can be accomplished by immunofluorescence techniques employing a fluorescently labeled antibody (see below) coupled with fluorescence microscopy, flow cytometric, or fluorometric detection.

The antibodies (or fragments thereof) useful in the present invention may be employed histologically, as in immunofluorescence or immunoelectron microscopy, for in situ detection of their antigens. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of the antigens but also its distribution on the examined tissue. Using the present invention, those of ordinary skill will readily perceive that any of wide variety of histological methods (such as staining procedures) can be modified in order to achieve such in situ detection.

Such assays for the antigens typically comprises incubating a biological sample, such as a biological fluid, a tissue extract, freshly harvested cells such as lymphocytes or leukocytes, or cells which have been incubated in tissue culture, in the presence of a labeled antibody capable of identifying the antigens, and detecting the antibody by any of a number of techniques well known in the art.

The biological sample may be coupled to a solid phase support or carrier such as nitrocellulose, or other solid support or carrier which is capable of immobilizing cells, cell particles or soluble proteins. The support or carrier may then be washed with suitable buffers followed by treatment with a labeled antibody in accordance with the present invention, as noted above. The solid phase support or carrier may then be washed with the buffer a second time to remove unbound antibody. The amount of bound label on said solid support or carrier may then be detected by conventional means.

An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

The antibodies of the invention can be used in connection with immunoaffinity chromatography technology. More specifically, the antibodies can be placed on the surface of a material within a chromatography column. Thereafter, a composition to be purified can be passed through the column. If the sample to be purified includes any sCSF3R polypeptides which binds to the antibodies those sCSF3R polypeptides will be removed from the sample and thereby purified.

Hence, in summary methods of diagnosis can be performed in vitro using a cellular sample (e.g., blood sample, lymph node biopsy or tissue) from a mammal or can be performed by in vivo imaging.

Compositions comprising the antibodies of the present invention can be used to detect the presence of sCSF3R, for example, by radioimmunoassay, ELISA, FACS, etc. One or more labeling moieties can be attached to the humanized immunoglobulin. Exemplary labeling moieties include radiopaque dyes, radiocontrast agents, fluorescent molecules, spin-labeled molecules, enzymes, or other labeling moieties of diagnostic value, particularly in radiologic or magnetic resonance imaging techniques.

An IgG antibody preparation of the present invention may be advantageously purified from an anti-serum of the present invention using protein-G affinity purification, preferably via protein-G immunoprecipitation. An anti-serum derived from an animal immunized, can be used for detecting with optimal sensitivity, via Western immunoblotting analysis, Immunoprecipitation and ELISA, the sCSF3R polypeptides.

In general, for applications benefiting from optimal reproducibility, standardization, or precision, a purified antibody or antibody fragment of the present invention capable of specifically binding the target antigen will generally be optimal relative to an unpurified preparation of the present invention.

It will be appreciated by the ordinarily skilled artisan that an antibody or antibody fragment having an affinity characterized by a dissociation constant of up to $10^{-12}$ for a cognate antigen can be obtained using common art techniques.

As described hereinabove, the preparation may advantageously comprise an antibody or antibody fragment attached to any of various types of detectable molecule.

An antibody fragment has the advantage of being smaller than a parental antibody from which it is derived while retaining substantially identical target-antigen binding specificity, or both binding specificity and binding affinity, as the parental antibody. Thus, an antibody fragment, by virtue of being smaller than the parental antibody, will thereby generally have superior biodistribution, and diffusion properties (for example, systemically in-vivo, or in isolated tissues) than the latter. An antibody fragment substantially lacking an Fc region, such as a single-chain Fv, an Fab', an Fab an F(ab')$_2$ or a CDR, is advantageous for applications involving exposure of the preparation to a molecule capable of specifically binding such an Fc region, and in which such binding is undesirable. Typically this may involve an undesired binding of an Fc region exposed to a cognate Fc receptor, or an Fc-binding complement component (for example, complement component C1q, present in serum). Fc receptors are displayed on the surface of numerous immune cell types, including: professional APCs, such as dendritic cells; B lymphocytes; and granulocytes such as neutrophils, basophils, eosinophils, monocytes, macrophages, and mast cells. Thus, the absence of an Fc region from the antibody fragment may be particularly advantageous for avoiding undesired an Fc receptor-mediated immune cell activation or a complement component-mediated complement cascade, particularly when administering the preparation in-vivo to an individual.

An F(ab')$_2$ is a fragment of an antibody molecule containing a divalent antigen-binding portion of an antibody molecule.

An F(ab')$_2$ preparation of the present invention may be conveniently obtained using standard art methods by treating an antibody preparation of the present invention, such as an anti-serum of the present invention, with the enzyme pepsin. The resultant F(ab')$_2$ product is a 5S particle.

An Fab, or Fab' is a fragment of an antibody molecule containing a monovalent antigen-binding portion of an antibody.

The CDR can be generated e.g. as described in EP0585939 or as described by Strandberg et al. (Protein Eng. 2001 January; 14(1): 67-74). The CDR according to the invention can be a modified CDR, which has enhanced effect on the modulation of sCSF3Rpolypeptide. An example for methods of modification of active peptides is described by Sawa et al. 1999 (J. Med. Chem. 42, 3289-3299).

An Fab' preparation of the present invention may be conveniently obtained using standard art methods by treating an antibody preparation of the present invention, such as an anti-serum of the present invention, with the enzyme pepsin, followed by reduction of the resultant F(ab')$_2$ into. Such reduction may be effected using a thiol reducing agent, and optionally using a blocking group for the sulfhydryl groups resulting from cleavage of disulfide linkages. Such treatment generates two monovalent 3.5S Fab's an Fc fragment.

An Fab preparation may be conveniently obtained using standard art methods by treating an antibody preparation of the present invention, such as an anti-serum of the present invention, with the enzyme papain to yield the intact light chain and a portion of heavy chain composed of the variable and $C_H 1$ domains.

Ample guidance for generating an antibody fragment by enzymatic treatment of an antibody is provided in the literature of the art (for example, refer to: Goldenberg, U.S. Pat. Nos. 4,036,945 and 4,331,647; Porter R R., 1959. Biochem J. 73:119-126).

A single chain Fv (also referred to in the art as "scFv") is a single chain molecule including the variable region of the light chain and the variable region of the heavy chain, linked by a suitable polypeptide linker.

An F(ab')$_2$, Fab', Fab, or single-chain Fv or CDR preparation of the present invention may be obtained using recombinant techniques.

Obtaining a recombinant antibody fragment is effected by isolating mRNA of B lymphocytes of animals immunized with the target antigen, generating cDNA from the mRNA via RT-PCR, and using the cDNA to construct an antibody fragment phage-display library. B lymphocytes can be conveniently isolated from the spleen, or, alternately from the blood, bone-marrow, or lymph nodes of the immunized animal.

It will be appreciated that the above-described methodology can be used to obtain a monoclonal antibody fragment preparation of the present invention having essentially any desired target antigen-binding affinity and/or specificity. Such a preparation can be utilized in various applications benefiting from a reagent capable of binding the target antigen with such defined target antigen-binding characteristics.

Since an Fab' is essentially similar in structure to an Fab, a preparation of the present invention comprising an Fab' may be employed essentially interchangeably with one comprising an Fab, where such Fab' and Fab comprise essentially the same heavy and light chain variable regions. For applications, as will usually be the case, benefiting from a preparation of the present invention comprising an antibody fragment capable of binding the target antigen with maximal affinity, an F(ab')$_2$ preparation of the present invention may superior to an Fab, Fab' or scFv preparation of the present invention, due to the divalent binding of an F(ab')$_2$ to the target antigen relative to the monovalent binding of such a monovalent antibody fragment.

As mentioned hereinabove, depending on the application and purpose, the antibody or antibody fragment preparation may originate from any of various mammalian species An antibody or antibody fragment preparation of the present invention originating from a desired species may be derived from serum of the animal of such species immunized with the target antigen.

A preparation of the present invention of a human or humanized antibody or antibody fragment may be preferable for applications involving administration of the preparation to an individual. For example, a human or humanized antibody or antibody fragment will generally tend to be optimally tolerated immunologically, and hence will display an optimal half-life in-vivo in a human, and will thereby display optimal effectiveness. Further guidance regarding production and exploitation of human or humanized antibodies is provided hereinbelow.

The preparation may be used per se or it can be formulated as an active ingredient in a pharmaceutical composition.

Thus, according to the present invention there is provided a pharmaceutical composition comprising a pharmaceutically acceptable carrier and, as an active ingredient, an antibody or antibody fragment of the present invention.

Methods of formulating the antibody or antibody fragment of the present invention as an active ingredient in a pharmaceutical composition, and methods of exploiting such a pharmaceutical composition are described hereinbelow.

Preferably, administering the antibody or antibody fragment is effected by administering the pharmaceutical composition of the present invention comprising the antibody or antibody fragment of the present invention as an active ingredient.

The antibody or antibody fragment is preferably administered so as to achieve a sufficient level of antibody fragment bound to the target antigen so as to achieve a desired regulation of the biochemical activity.

An ordinarily skilled artisan, such as a physician, more preferably a physician specialized in the disease, will possess the required expertise for determining a suitable therapeutic protocol, including a suitable route of administration, and a suitable dosage of the antibody or antibody fragment for effectively treating the disease according to the teachings of the present invention.

Another aspect of this invention is a nucleic acid probe, wherein said probe selectively hybridizes to a nucleic acid as defined above or the complementary strand thereof. Probes denote a defined nucleic acid segment (or nucleotide analog segment, e.g., polynucleotide as defined herein) which can be used to identify a specific polynucleotide sequence present in samples, said nucleic acid segment comprising a nucleotide sequence complementary of the specific polynucleotide sequence to be identified. Probes of this invention typically comprise single-stranded nucleic acids of between 12 to 600 nucleotides in length, for instance of between 12 and 500, more preferably of between 15 and 400, typically of between 20 and 300. The sequence of the probes can be derived from the sequences of the CSF3R polypeptide variant gene sequence. The probe may contain nucleotide substitutions and/or chemical modifications, e.g., to increase the stability of hybrids or to label the probe. Typical examples of labels include, without limitation, radioactivity, fluorescence, luminescence, etc.

A further aspect of this invention is a nucleic acid primer that can be used to amplify at least a distinctive fragment of a nucleic acid molecule encoding a CSF3R polypeptide variant as defined above. A "primer" denotes a specific oligonucleotide sequence which is complementary to a target nucleotide sequence and used to hybridize to the target nucleotide sequence. A primer serves as an initiation point for nucleotide polymerization catalyzed by either DNA polymerase, RNA polymerase or reverse transcriptase. Typical primers of this invention are single-stranded nucleic acid molecules of about 6 to 50 nucleotides in length, more preferably of about 8 to about 40 nucleotides in length. The sequence of the primer can be derived directly from the sequence of the target nucleic acid molecule. Perfect complementarity between the primer sequence and the target gene is preferred, to ensure high specificity. However, certain mismatch may be tolerated.

Particular nucleic acid primers are able to specifically hybridize with a portion of the CSF3R variant nucleic acid that either flanks or encodes a distinctive fragment of such polypeptides. Specific examples of primers of this invention are disclosed below:

```
sCSF3R-F1:
                                         (SEQ ID NO: 13)
ATGGCAAGGCTGGGAAACTG sCSF3R-R1:
                                         (SEQ ID NO: 14)
TTTAGTAGAGGCGGGGTTTCG sCSF3R-F1 nest:
                                         (SEQ ID NO: 15)
ACTTGGGCTGCCCTGATCATCC sCSF3R-R1 nest:
                                         (SEQ ID NO: 16)
TGGCCAGGCTGATCATGAACTC sCSF3R-EX1:
                                         (SEQ ID NO: 17)
GAAACTGCAGCCTGACTTGGGCTGCCCTGATCA sCSF3R-EX2:
                                         (SEQ ID NO: 18)
GAGGCGGGGTTTCGCCTTGCTGGCCAGGCTGATCATGAAC sCSF3R-EX3:
                                         (SEQ ID NO: 19)
ATGGCAAGGCTGGGAAACTGCAGCCTGACTT sCSF3R-EX4:
                                         (SEQ ID NO: 20)
ATTTTTTTGTATTTTTAGTAGAGGCGGGGTTTCGCCTT sCSF3R-EX5:
                                         (SEQ ID NO: 21)
GCAGGCTTCGCCACCATGGCAAGGCTGGGAAACTG sCSF3R-EX6:
                                         (SEQ ID NO: 22)
GGGGACAAGTTTGTACAAAAAAGCAGGCTTCGCCACC
```

A further aspect of this invention thus resides in the use of a primer or probe as disclosed above to detect or diagnose the presence of a nucleic acid encoding a CSF3R polypeptide variant of this invention in a sample. The method can be carried out according to techniques well know in the art, such as by contacting a sample with a probe as defined above under conditions allowing hybridisation to occur, and determining the presence of a hybrid; or by contacting a sample with a primer as defined above under conditions allowing nucleic acid amplification, and determining the presence of an amplification product.

Thus, this invention also relates to the use of nucleic acid molecules according to the present invention as diagnostic reagents. Detection of a mutated form of the gene characterised by the nucleic acid molecules of the invention which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques.

Nucleic acid molecules for diagnosis may be obtained from a subject's cells, such as from blood, urine, saliva, tissue biopsy or autopsy material. The genomic DNA may be used directly for detection or may be amplified enzymatically by using PCR, ligase chain reaction (LCR), strand displacement amplification (SDA), or other amplification techniques (see Saiki et al., Nature, 324, 163-166 (1986); Bej, et al., Crit. Rev. Biochem. Molec. Biol., 26, 301-334 (1991); Birkenmeyer et al., J. Virol. Meth., 35, 117-126 (1991); Van Brunt, J., Bio/Technology, 8, 291-294 (1990)) prior to analysis.

In one embodiment, this aspect of the invention provides a method of diagnosing a disease in a patient, comprising assessing the level of expression of a natural gene encoding a polypeptide according to the invention and comparing said level of expression to a control level, wherein a level that is different to said control level is indicative of disease. The method may comprise the steps of:

a) contacting a sample of tissue from the patient with a nucleic acid probe under stringent conditions that allow the formation of a hybrid complex between a nucleic acid molecule of the invention and the probe;

b) contacting a control sample with said probe under the same conditions used in step a);

c) and detecting the presence of hybrid complexes in said samples;

wherein detection of levels of the hybrid complex in the patient sample that differ from levels of the hybrid complex in the control sample is indicative of disease.

A further aspect of the invention comprises a diagnostic method comprising the steps of:

a) obtaining a tissue sample from a patient being tested for disease;

b) isolating a nucleic acid molecule according to the invention from said tissue sample; and c) diagnosing the patient for disease by detecting the presence of a mutation in the nucleic acid molecule which is associated with disease.

To aid the detection of nucleic acid molecules in the above-described methods, an amplification step, for example using PCR, may be included.

Deletions and insertions can be detected by a change in the size of the amplified product in comparison to the normal genotype. Point mutations can be identified by hybridizing amplified DNA to labelled RNA of the invention or alternatively, labelled antisense DNA sequences of the invention. Perfectly-matched sequences can be distinguished from mismatched duplexes by RNase digestion or by assessing differences in melting temperatures. The presence or absence of the mutation in the patient may be detected by contacting DNA with a nucleic acid probe that hybridises to the DNA under stringent conditions to form a hybrid double-stranded molecule, the hybrid double-stranded molecule having an unhybridised portion of the nucleic acid probe strand at any portion corresponding to a mutation associated with disease; and detecting the presence or absence of an unhybridised portion of the probe strand as an indication of the presence or absence of a disease-associated mutation in the corresponding portion of the DNA strand.

Such diagnostics are particularly useful for prenatal and even neonatal testing.

Point mutations and other sequence differences between the reference gene and "mutant" genes can be identified by other well-known techniques, such as direct DNA sequencing or single-strand conformational polymorphism, (see Orita et al., Genomics, 5, 874-879 (1989)). For example, a sequencing primer may be used with double-stranded PCR product or a single-stranded template molecule generated by a modified PCR. The sequence determination is performed by conventional procedures with radiolabelled nucleotides or by automatic sequencing procedures with fluorescent-tags. Cloned DNA segments may also be used as probes to detect specific DNA segments. The sensitivity of this method is greatly enhanced when combined with PCR. Further, point mutations and other sequence variations, such as polymorphisms, can be detected as described above, for example, through the use of allele-specific oligonucleotides for PCR amplification of sequences that differ by single nucleotides.

DNA sequence differences may also be detected by alterations in the electrophoretic mobility of DNA fragments in gels, with or without denaturing agents, or by direct DNA sequencing (for example, Myers et al., Science (1985) 230: 1242). Sequence changes at specific locations may also be revealed by nuclease protection assays, such as RNase and SI protection or the chemical cleavage method (see Cotton et al., Proc. Natl. Acad. Sci. USA (1985) 85: 4397-4401).

In addition to conventional gel electrophoresis and DNA sequencing, mutations such as microdeletions, aneuploidies, translocations, inversions, can also be detected by in situ analysis (see, for example, Keller et al., DNA Probes, 2nd Ed., Stockton Press, New York, N.Y., USA (1993)), that is, DNA or RNA sequences in cells can be analysed for mutations without need for their isolation and/or immobilisation onto a membrane. Fluorescence in situ hybridization (FISH) is presently the most commonly applied method and numerous reviews of FISH have appeared (see, for example, Trachuck et al., Science, 250, 559-562 (1990), and Trask et al., Trends, Genet., 7, 149-154 (1991)).

In another embodiment of the invention, an array of oligonucleotide probes comprising a nucleic acid molecule according to the invention can be constructed to conduct efficient screening of genetic variants, mutations and polymorphisms. Array technology methods are well known and have general applicability and can be used to address a variety of questions in molecular genetics including gene expression, genetic linkage, and genetic variability (see for example: M. Chee et al., Science (1996), Vol 274, pp 610-613).

In one embodiment, the array is prepared and used according to the methods described in PCT application WO95/11995 (Chee et al); Lockhart, D. J. et al. (1996) Nat. Biotech. 14: 1675-1680); and Schena, M. et al. (1996) Proc. Natl. Acad. Sci. 93: 10614-10619). Oligonucleotide pairs may range from two to over one million. The oligomers are synthesized at designated areas on a substrate using a light-directed chemical process. The substrate may be paper, nylon or other type of membrane, filter, chip, glass slide or any other suitable solid support. In another aspect, an oligonucleotide may be synthesized on the surface of the substrate by using a chemical coupling procedure and an ink jet application apparatus, as described in PCT application WO95/25116 (Baldeschweiler et al). In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and over one million which lends itself to the efficient use of commercially-available instrumentation.

In addition to the methods discussed above, diseases may be diagnosed by methods comprising determining, from a sample derived from a subject, an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods.

Assay techniques that can be used to determine levels of a polypeptide of the present invention in a sample derived from a host are well-known to those of skill in the art and are discussed in some detail above (including radioimmunoassays, competitive-binding assays, Western Blot analysis and ELISA assays). This aspect of the invention provides a diagnostic method which comprises the steps of: (a) contacting a ligand as described above with a biological sample under conditions suitable for the formation of a ligand-polypeptide complex; and (b) detecting said complex.

Protocols such as ELISA, RIA, and FACS for measuring polypeptide levels may additionally provide a basis for diagnosing altered or abnormal levels of polypeptide expression. Normal or standard values for polypeptide expression are established by combining body fluids or cell extracts taken from normal mammalian subjects, preferably humans, with antibody to the polypeptide under conditions suitable for complex formation. The amount of standard complex formation may be quantified by various methods, such as by photometric means.

Antibodies which specifically bind to a polypeptide of the invention may be used for the diagnosis of conditions or diseases characterised by expression of the polypeptide, or in assays to monitor patients being treated with the polypeptides, nucleic acid molecules, ligands and other compounds of the invention. Antibodies useful for diagnostic purposes may be prepared in the same manner as those described above for therapeutics. Diagnostic assays for the polypeptide include methods that utilise the antibody and a label to detect the polypeptide in human body fluids or extracts of cells or tissues. The antibodies may be used with or without modification, and may be labelled by joining them, either covalently or non-covalently, with a reporter molecule. A wide variety of reporter molecules known in the art may be used, several of which are described above.

Quantities of polypeptide expressed in subject, control and disease samples from biopsied tissues are compared with the standard values. Deviation between standard and subject values establishes the parameters for diagnosing disease. Diagnostic assays may be used to distinguish between absence, presence, and excess expression of polypeptide and to monitor regulation of polypeptide levels during therapeutic intervention. Such assays may also be used to evaluate the efficacy of a particular therapeutic treatment regimen in animal studies, in clinical trials or in monitoring the treatment of an individual patient.

A diagnostic kit of the present invention may comprise:

(a) a nucleic acid molecule of the present invention;

(b) a polypeptide of the present invention; or (c) a ligand of the present invention.

In one aspect of the invention, a diagnostic kit may comprise a first container containing a nucleic acid probe that hybridises under stringent conditions with a nucleic acid molecule according to the invention; a second container containing primers useful for amplifying the nucleic acid molecule; and instructions for using the probe and primers for facilitating the diagnosis of disease. The kit may further comprise a third container holding an agent for digesting unhybridised RNA.

In an alternative aspect of the invention, a diagnostic kit may comprise an array of nucleic acid molecules, at least one of which may be a nucleic acid molecule according to the invention.

To detect polypeptide according to the invention, a diagnostic kit may comprise one or more antibodies that bind to a polypeptide according to the invention; and a reagent useful for the detection of a binding reaction between the antibody and the polypeptide.

Such kits will be of use in diagnosing a disease or susceptibility to disease selected from graft-vs-host disease, cancer, neutropenia, neurological disorders or conditions, pneumonia, autoimmune diseases, haematological diseases, hemopoietic disorders, infectious diseases, inflammatory bowel disease, and diabetes.

Expression of a polypeptide of the present invention is also an effective marker in evaluating the degree of myelopoiesis and the activity or making prognoses of malignant disorders of myeloid lineages (e.g. acute myeloblastic leukaemia) or of hemopoietic disorders (Iwasaki et al.).

Further aspects and advantages of the present invention will be disclosed in the following examples, which should be considered as illustrative only, and do not limit the scope of this application.

TABLE 1

| Amino Acid | Synonymous Groups | More Preferred Synonymous Groups |
|---|---|---|
| Ser | Gly, Ala, Ser, Thr, Pro | Thr, Ser |
| Arg | Asn, Lys, Gln, Arg, His | Arg, Lys, His |
| Leu | Phe, Ile, Val, Leu, Met | Ile, Val, Leu, Met |
| Pro | Gly, Ala, Ser, Thr, Pro | Pro |
| Thr | Gly, Ala, Ser, Thr, Pro | Thr, Ser |
| Ala | Gly, Thr, Pro, Ala, Ser | Gly, Ala |
| Val | Met, Phe, Ile, Leu, Val | Met, Ile, Val, Leu |
| Gly | Ala, Thr, Pro, Ser, Gly | Gly, Ala |
| Ile | Phe, Ile, Val, Leu, Met | Ile, Val, Leu, Met |
| Phe | Trp, Phe, Tyr | Tyr, Phe |
| Tyr | Trp, Phe, Tyr | Phe, Tyr |
| Cys | Ser, Thr, Cys | Cys |
| His | Asn, Lys, Gln, Arg, His | Arg, Lys, His |
| Gln | Glu, Asn, Asp, Gln | Asn, Gln |
| Asn | Glu, Asn, Asp, Gln | Asn, Gln |
| Lys | Asn, Lys, Gln, Arg, His | Arg, Lys, His |
| Asp | Glu, Asn, Asp, Gln | Asp, Glu |
| Glu | Glu, Asn, Asp, Gln | Asp, Glu |
| Met | Phe, Ile, Val, Leu, Met | Ile, Val, Leu, Met |
| Trp | Trp, Phe, Tyr | Trp |

TABLE 2

| Amino Acid | Synonymous Groups |
|---|---|
| Ser | D-Ser, Thr, D-Thr, allo-Thr, Met, D-Met, Met(O), D-Met(O), L-Cys, D-Cys |
| Arg | D-Arg, Lys, D-Lys, homo-Arg, D-homo-Arg, Met, Ile, D-.Met, D-Ile, Orn, D-Orn |
| Leu | D-Leu, Val, D-Val, AdaA, AdaG, Leu, D-Leu, Met, D-Met |
| Pro | D-Pro, L-I-thioazolidine-4-carboxylic acid, D-or L-1-oxazolidine-4-carboxylic acid |
| Thr | D-Thr, Ser, D-Ser, allo-Thr, Met, D-Met, Met(O), D-Met(O), Val, D-Val |
| Ala | D-Ala, Gly, Aib, B-Ala, Acp, L-Cys, D-Cys |
| Val | D-Val, Leu, D-Leu, Ile, D-Ile, Met, D-Met, AdaA, AdaG |
| Gly | Ala, D-Ala, Pro, D-Pro, Aib, .beta.-Ala, Acp |
| Ile | D-Ile, Val, D-Val, AdaA, AdaG, Leu, D-Leu, Met, D-Met |
| Phe | D-Phe, Tyr, D-Thr, L-Dopa, His, D-His, Trp, D-Trp, Trans-3,4, or 5-phenylproline, AdaA, AdaG, cis-3,4, or 5-phenylproline, Bpa, D-Bpa |
| Tyr | D-Tyr, Phe, D-Phe, L-Dopa, His, D-His |
| Cys | D-Cys, S--Me--Cys, Met, D-Met, Thr, D-Thr |
| Gln | D-Gln, Asn, D-Asn, Glu, D-Glu, Asp, D-Asp |
| Asn | D-Asn, Asp, D-Asp, Glu, D-Glu, Gln, D-Gln |
| Lys | D-Lys, Arg, D-Arg, homo-Arg, D-homo-Arg, Met, D-Met, Ile, D-Ile, Orn, D-Orn |
| Asp | D-Asp, D-Asn, Asn, Glu, D-Glu, Gln, D-Gln |
| Glu | D-Glu, D-Asp, Asp, Asn, D-Asn, Gln, D-Gln |
| Met | D-Met, S--Me--Cys, Ile, D-Ile, Leu, D-Leu, Val, D-Val |

EXAMPLES

Example 1

Cloning of sCSF3R Ig-Like C2 Type Domain

Introduction sCSF3R is a variant of the CSF3R gene (colony stimulating factor 3 receptor). The CSF3R gene is composed by 15 coding exons. There are 2 non coding exons in the 5' UTR. sCSF3R is a protein of 189 amino acids containing a signal peptide (amino acids 1-25) and a Lep_receptor Ig-like C2-type domain (amino acids 22-111). It is identical to the N-terminal of wild type CSF3R (Q99062) over the first 120 amino acids (spanning exon 3 and the 5' end of exon 4) but deviates in exon 4 thus introducing a different C-terminal and a premature stop codon which is predicted to produce a truncated protein.

Two PCR primer pairs (sCSF3R-F1/sCSF3R-R1 and sCSF3R-F1 nest/sCSF3R-R1-nest) (FIG. 1) were designed to act as nested pairs, with the first pair forming the outer pair. sCSF3R-F1 nest/sCSF3R-R1-nest were designed to amplify a 500 bp product within exons 3 and 4 of the sCSF3R sequence. A clone was identified, amplified from pool PS3 containing cDNA derived from mixed RA synovium, mixed osteoarthritis and lung fibroblasts, which contained the sequence sCSF3R except for 27 bp missing at the 5' end and 40 bp missing at the 3' end due to the position of the nested primers used for the PCR. This clone is pCR4-TOPO-sCSF3RF1/R1nest. The missing nucleotides were added during the subcloning of the cDNA into Gateway expression vectors.

Cloning of SCSF3R a) Preparation of Human cDNA Templates

First strand cDNA was prepared from a variety of human tissue total RNA samples (Clontech, Stratagene, Ambion, Biochain Institute and in-house preparations) using Superscript II or SuperScript III RNase H⁻ Reverse Transcriptase (Invitrogen) according to the manufacturer's protocol.

For SuperScript II: Oligo (dT)$_{15}$ primer (1 µl at 500 µg/ml) (Promega), 2 µg human total RNA, 1 µl 10 mM dNTP mix (10 mM each of dATP, dGTP, dCTP and dTTP at neutral pH) and sterile distilled water to a final volume of 12 µl were combined in a 1.5 ml Eppendorf tube, heated to 65° C. for 5 min and chilled on ice. The contents were collected by brief centrifugation and 4 µl of 5× First-Strand Buffer, 2 µl 0.1 M DTT, and 1 µl RnaseOUT™ Recombinant Ribonuclease Inhibitor (40 units/µl, Invitrogen) were added. The contents of the tube were mixed gently and incubated at 42° C. for 2 min, then 1 µl (200 units) of SuperScript II™ enzyme was added and mixed gently by pipetting. The mixture was incubated at 42° C. for 50 min and then inactivated by heating at 70° C. for 15 min. To remove RNA complementary to the cDNA, 1 µl (2 units) of E. coli RNase H (Invitrogen) was added and the reaction mixture incubated at 37° C. for 20 min.

For SuperScript III: 1 µl Oligo(dT)$_{20}$ primer (50 µM, Invitrogen), 2 µg human total RNA, 1 µl 10 mM dNTP mix (10 mM each of dATP, dGTP, dCTP and dTTP at neutral pH) and sterile distilled water to a final volume of 10 µl were combined in a 1.5 ml Eppendorf tube, heated to 65° C. for 5 min and then chilled on ice. For each RT reaction a cDNA synthesis mix was prepared as follows: 2 µl 10×RT buffer, 4 µl 25 mM MgCl$_2$, 2 µl 0.1M DTT, 1 µl RNaseOUT™ (40 U/µl) and 1 µl SuperScript III™ RT enzyme were combined in a separate tube and then 10 µl of this mix added to the tube containing the RNA/primer mixture. The contents of the tube were mixed gently, collected by brief centrifugation, and incubated at 50° C. for 50 min. The reaction was terminated by incubating at 80° C. for 5 min and the reaction mixture then chilled on ice and collected by brief centrifugation. To remove RNA complementary to the cDNA, 1 µl (2 units) of E. coli RNase H (Invitrogen) was added and the reaction mixture incubated at 37° C. for 20 min.

The final 21 µl reaction mix was diluted by adding 179 µl sterile water to give a total volume of 200 µl. The RNA samples were combined into pools such that each pool contained five different cDNA samples. 5 µl of each cDNA pool was used as a template for PCR in a 50 µl final reaction volume and this consisted of 1 µl of each cDNA sample in that pool. This represented approximately 20 ng of each individual cDNA template.

b) cDNA Libraries

Human cDNA libraries (in bacteriophage lambda (λ) vectors) were purchased from Stratagene, Clontech or Invitrogen, or prepared at the Serono Pharmaceutical Research Institute in λ ZAP, λ GTI10, λ GT11, or TriplEx2 vectors according to the manufacturer's protocol (Stratagene, Clontech and Invitrogen). Bacteriophage λ DNA was prepared from small scale cultures of infected E. coli host strain using the Wizard Lambda Preps DNA purification system according to the manufacturer's instructions (Promega, Corporation, Madison Wis.).

c) Gene Specific Cloning Primers for PCR

Two pairs of PCR primers having a length of between 18 and 25 bases were designed for amplifying the sCSF3R exons 3 and 4 sequence using Primer Designer Software (Scientific & Educational Software, PO Box 72045, Durham, N.C. 27722-2045, USA). PCR primers were optimised to have a Tm close to 55±10° C. and a GC content of 40-60%. Primers were selected which had high selectivity for the target sequence (sCSF3R) with little or no none specific priming. The primers were designed to form two nested pairs such that sCSF3R-F1nest/sCSF3R-R1 nest primers were positioned slightly internal to primers sCSF3R-F1/sCSF3R-R1.

d) PCR Amplification of SCSF3R Human cDNA Templates

Gene-specific cloning primers sCSF3R-F1/sCSF3R-R1 (Table 3, FIG. 1) were designed to amplify a cDNA fragment of 554 bp within sCSF3R exons 3 and 4. The primer pair sCSF3R-F1/sCSF3R-R1 was used in PCR1 on the panel of cDNA library templates and the pools of cDNA templates from individual tissues. This PCR1 was performed in a final volume of 50 µl containing 1× AmpliTaq™ buffer, 200 µM dNTPs, 50 pmoles of each cloning primer, 2.5 units of AmpliTaq™ (Applied Biosystems) and approximately 20 ng of cDNA library or 100 ng of pooled cDNA template using an MJ Research DNA Engine, programmed as follows: 94° C., 2 min; 40 cycles of 94° C., 1 min, 57° C., 1 min, and 72° C., 1 min; followed by 1 cycle at 72° C. for 7 min and a holding cycle at 4° C. 30 µl of each PCR1 amplification product was visualized on a 0.8% agarose gel in 1×TAE buffer (Invitrogen) but no products were seen.

Each PCR1 product was then used as template for PCR2 using amplification primers sCSF3R-F1nest/sCSF3R-R1nest (Table 3, FIG. 1-4), designed to amplify a cDNA fragment of 500 bp within the sCSF3R-F1/sCSF3R-R1 product. PCR2 was performed in a final volume of 50 µl containing 1× AmpliTaq™ buffer, 200 µM dNTPs, 50 pmoles of each cloning primer, 2.5 units of AmpliTaq™ (Applied Biosystems), and 1 µl of PCR1 product using an MJ Research DNA Engine, programmed as follows: 94° C., 2 min; 40 cycles of 94° C., 1 min, 61° C., 1 min, and 72° C., 1 min; followed by 1 cycle at 72° C. for 7 min and a holding cycle at 4° C.

30 µl of each PCR2 amplification product was visualized on a 0.8% agarose gel in 1×TAE buffer (Invitrogen). Products of the approximately the expected molecular weight were purified from the gel using Qiagen MinElute DNA Purification System (Qiagen), eluted in 10 µl of EB buffer (10 mM Tris.Cl, pH 8.5) and subcloned directly.

e) Subcloning of PCR Products

The PCR products were subcloned into the topoisomerase I modified cloning vector (pCR4-TOPO) using the TA cloning kit purchased from the Invitrogen Corporation using the conditions specified by the manufacturer. Briefly, 4 µl of gel purified PCR product was incubated for 15 min at room temperature with 1 µl of TOPO vector and 1 µl salt solution. The reaction mixture was then transformed into E. coli strain TOP10 (Invitrogen) as follows: a 50 µl aliquot of One Shot TOP10 cells was thawed on ice and 2 µl of TOPO reaction was added. The mixture was incubated for 15 min on ice and then heat shocked by incubation at 42° C. for exactly 30 s. Samples were returned to ice and 250 µl of warm (room temperature) SOC media was added. Samples were incubated with shaking (220 rpm) for 1 h at 37° C. The transformation mixture was then plated on L-broth (LB) plates containing ampicillin (100 µg/ml) and incubated overnight at 37° C.

f) Colony PCR

Colonies were inoculated into 50 µl sterile water using a sterile toothpick. A 10 µl aliquot of the inoculum was then subjected to PCR in a total reaction volume of 20 µl containing 1× AmpliTaq™ buffer, 200 µM dNTPs, 20 pmoles of T7 primer, 20 pmoles of T3 primer, and 1 unit of AmpliTaq (Applied Biosystems) using an MJ Research DNA Engine. The cycling conditions were as follows: 94° C., 2 min; 30 cycles of 94° C., 30 sec, 48° C., 30 sec and 72° C. for 1 min. Samples were maintained at 4° C. (holding cycle) before further analysis.

PCR reaction products were analyzed on 1% agarose gels in 1×TAE buffer. Colonies which gave PCR products of approximately the expected molecular weight (500 bp+105 bp due to the multiple cloning site (MCS)) were grown up overnight at 37° C. in 5 ml L-Broth (LB) containing ampicillin (100 µg/ml), with shaking at 220 rpm.

f) Plasmid DNA Preparation and Sequencing

Miniprep plasmid DNA was prepared from the 5 ml culture using a Biorobot 8000 robotic system (Qiagen) or Wizard Plus SV Minipreps kit (Promega cat. no. 1460) according to the manufacturer's instructions. Plasmid DNA was eluted in 80 µl of sterile water. The DNA concentration was measured using a Spectramax 190 photometer (Molecular Devices). Plasmid DNA (200-500 ng) was subjected to DNA sequencing with the T7 and T3 primers (Table 3) using the BigDye Terminator system (Applied Biosystems cat. no. 4390246) according to the manufacturer's instructions. Sequencing reactions were purified using Dye-Ex columns (Qiagen) or Montage SEQ 96 cleanup plates (Millipore cat. no. LSKS09624) then analyzed on an Applied Biosystems 3700 sequencer.

Sequence analysis identified a clone, amplified from a pool (PS3) containing cDNA derived from mixed RA synovium, mixed osteoarthritis cells and lung fibroblasts, which contained sCSF3R sequence. In the cloned sequence, 27 bp was missing at the 5' end and 40 bp missing at the 3' end due to the position of the nested primers used for the PCR. The sequence of the cloned cDNA fragment is shown in FIG. 2. The cloned PCR product is contained in plasmid pCR4-TOPO-sCSF3RF1/R1nest.

Construction of Mammalian Cell Expression Vectors for sCSF3R

Plasmid pCR4-TOPO-sCSF3RF1/R1nest was used as PCR template to generate pEAK12d and pDEST12.2 expression clones containing the sCSF3R ORF sequence with a 3' sequence encoding a 6HIS tag using the Gateway™ cloning methodology (Invitrogen).

a) Generation of Gateway Compatible sCSF3R ORF Fused to an In Frame 6HIS Tag Sequence.

The first stage of the Gateway cloning process involves a four step PCR reaction which generates the ORF of sCSF3R flanked at the 5' end by an attB1 recombination site and Kozak sequence, and flanked at the 3' end by a sequence encoding an in-frame 6 histidine (6HIS) tag, a stop codon and the attB2 recombination site (Gateway compatible cDNA). The missing bases of the predicted cds were added with the forward primers sCSF3R-EX1, sCSF3R-EX3 and reverse primers sCSF3R-EX2, sCSF3R-EX4.

The first PCR reaction (in order to add 14 bases at the 5' end and 18 bases at the 3' end) contains respectively (in a final volume of 50 µl): 1 µl (30 ng) of plasmid pCR4-TOPO-sCSF3RF1/R1nest, 1.5 µl dNTPs (10 mM), 10 µl of 10× Pfx polymerase buffer, 1 µl MgSO4 (50 mM), 0.5 µl each of gene specific primer (100 µM) (sCSF3R-EX1 and sCSF3R-EX2), and 0.5 µl Platinum Pfx DNA polymerase (Invitrogen). The PCR reaction was performed using an initial denaturing step of 95° C. for 2 min, followed by 20 cycles of 94° C. for 15 s; 55° C. for 30 s and 68° C. for 2 min; and a holding cycle of 4° C.

A 10 µl aliquot was visualized on 0.8% agarose gel in 1×TAE buffer (Invitrogen) in order to verify that the product was of the expected molecular weight (500±32=532 bp). The remaining 40 µl were loaded on 0.8% agarose gel in 1×TAE buffer gel and the band was purified using the Wizard PCR Preps DNA Purification System (Promega) and recovered in 50 µl sterile water according to the manufacturer's instructions. The second PCR reaction (to add the remaining nucleotides at both ends) contains respectively (in a final volume of 50 µl): 4 µl of purified PCR1 product, 1.5 µl dNTPs (10 mM), 10 μl of 10× Pfx polymerase buffer, 1 μl MgSO$_4$ (50 mM), 0.5 μl each of gene specific primer (100 μM) (sCSF3R-EX3 and sCSF3R-EX4), and 0.5 μl Platinum Pfx DNA polymerase (Invitrogen). The PCR reaction was performed using an initial denaturing step of 95° C. for 2 min, followed by 20 cycles of 94° C. for 15 s; 55° C. for 30 s and 68° C. for 2 min; and a holding cycle of 4° C. A 10 μl aliquot was visualized on 0.8% agarose gel in 1×TAE buffer (Invitrogen) in order to verify that the product was of the expected molecular weight. The remaining 40 μl were loaded on 0.8% agarose gel in 1×TAE buffer gel and the band was purified using the Wizard SV Gel and PCR Clean-up System (Promega) and recovered in 40 μl sterile water according to the manufacturer's instructions.

The third PCR reaction (in a final volume of 50 μl) contains respectively: 4 μl of purified PCR2 product, 1.5 μl dNTPs (10 mM), 10 μl of 10× Pfx polymerase buffer, 1 μl MgSO$_4$ (50 mM), 0.5 μl each of gene specific primer (100 μM) (sCSF3R-EX5 and sCSF3R-EX6), and 0.5 μl Platinum Pfx DNA polymerase (Invitrogen). The PCR reaction was performed using an initial denaturing step of 95° C. for 2 min, followed by 12 cycles of 94° C. for 15 s; 55° C. for 30 s and 68° C. for 2 min; and a holding cycle of 4° C. The amplification product was directly purified using the Wizard PCR Preps DNA Purification System (Promega) and recovered in 50 μl sterile water according to the manufacturer's instructions.

The fourth PCR reaction (in a final volume of 50 μl) contained 10 μl purified PCR3 product, 1.5 μl dNTPs (10 mM), 5 μl of 10× Pfx polymerase buffer, 1 μl MgSO$_4$ (50 mM), 0.5 μl of each Gateway conversion primer (100 μM) (GCP forward and GCP reverse) and 0.5 μl of Platinum Pfx DNA polymerase. The conditions for the 2nd PCR reaction were: 95° C. for 1 min; 4 cycles of 94° C., 15 sec; 50° C., 30 sec and 68° C. for 2 min; 25 cycles of 94° C., 15 sec; 55° C., 30 sec and 68° C., 2 min; followed by a holding cycle of 4° C. A 10 μl aliquot was visualized on 0.8% agarose gel in 1×TAE buffer (Invitrogen) in order to verify that the product was of the expected molecular weight (567±70=637 bp). The remaining 40 μl were loaded on 0.8% agarose gel in 1×TAE buffer gel and the band was purified using the Wizard PCR Preps DNA Purification System (Promega) and recovered in 50 μl sterile water according to the manufacturer's instructions.

b) Subcloning of Gateway Compatible SCSF3R ORF into Gateway Entry Vector pDONR221 and Expression Vectors pEAK12d and pDEST12.2

The second stage of the Gateway cloning process involves subcloning of the Gateway modified PCR product into the Gateway entry vector pDONR221 (Invitrogen) as follows: 5 μl of purified product from PCR4 were incubated with 1.5 μl pDONR221 vector (0.1 μg/μl), 2 μl BP buffer and 1.5 μl of BP clonase enzyme mix (Invitrogen) in a final volume of 10 μl at RT for 1 h. The reaction was stopped by addition of proteinase K 1 μl (2 μg/μl) and incubated at 37° C. for a further 10 min. An aliquot of this reaction (1 μl) was used to transform E. coli DH10B cells by electroporation as follows: a 25 μl aliquot of DH10B electrocompetent cells (Invitrogen) was thawed on ice and 1 μl of the BP reaction mix was added. The mixture was transferred to a chilled 0.1 cm electroporation cuvette and the cells electroporated using a BioRad Gene-Pulser™ according to the manufacturer's recommended protocol. SOC media (0.5 ml) which had been pre-warmed to room temperature was added immediately after electroporation. The mixture was transferred to a 15 ml snap-cap tube and incubated, with shaking (220 rpm) for 1 h at 37° C. Aliquots of the transformation mixture (10 μl and 50 μl) were then plated on L-broth (LB) plates containing kanamycin (40 μg/ml) and incubated overnight at 37° C.

Plasmid miniprep DNA was prepared from 5 ml culture from 8 of the resultant colonies using a Qiaprep BioRobot 8000 system (Qiagen). Plasmid DNA (150-200 ng) was subjected to DNA sequencing with 21M13 and M13Rev primers using the BigDyeTerminator system (Applied Biosystems cat. no. 4336919) according to the manufacturer's instructions. The primer sequences are shown in Table 3. Sequencing reactions were purified using Montage SEQ 96 cleanup plates (Millipore cat. no. LSKS09624) then analyzed on an Applied Biosystems 3700 sequencer.

Plasmid eluate (2 μl or approx. 150 ng) from one of the clones which contained the correct sequence (pENTR_sCSF3R-6HIS) was then used in a recombination reaction containing 1.5 μl of either pEAK12d vector or pDEST12.2 vector (0.1 μg/μl), 2 μl LR buffer and 1.5 μl of LR clonase (Invitrogen) in a final volume of 10 μl. The mixture was incubated at RT for 1 h, stopped by addition of proteinase K (2 μg) and incubated at 37° C. for a further 10 min. An aliquot of this reaction (1 ul) was used to transform E. coli DH10B cells by electroporation as follows: a 25 μl aliquot of DH10B electrocompetent cells (Invitrogen) was thawed on ice and 1 μl of the LR reaction mix was added. The mixture was transferred to a chilled 0.1 cm electroporation cuvette and the cells electroporated using a BioRad Gene-Pulser™ according to the manufacturer's recommended protocol. SOC media (0.5 ml) which had been pre-warmed to room temperature was added immediately after electroporation. The mixture was transferred to a 15 ml snap-cap tube and incubated, with shaking (220 rpm) for 1 h at 37° C. Aliquots of the transformation mixture (10 μl and 50 μl) were then plated on L-broth (LB) plates containing ampicillin (100 μg/ml) and incubated overnight at 37° C.

Plasmid mini-prep DNA was prepared from 5 ml cultures from 6 of the resultant colonies subcloned in each vector using a Qiaprep BioRobot 8000 system (Qiagen). Plasmid DNA (200-500 ng) in the pEAK12d vector was subjected to DNA sequencing with pEAK12F and pEAK12R primers as described above. Plasmid DNA (200-500 ng) in the pDEST12.2 vector was subjected to DNA sequencing with 21M13 and M13Rev primers as described above. Primer sequences are shown in Table 3.

CsCl gradient purified maxi-prep DNA was prepared from a 500 ml culture of the sequence verified clone (pEAK12d_sCSF3R-6HIS) using the method described by Sambrook J. et al., 1989 (in Molecular Cloning, a Laboratory Manual, 2$^{nd}$ edition, Cold Spring Harbor Laboratory Press). Plasmid DNA was resuspended at a concentration of 1 μg/μl in sterile water (or 10 mM Tris-HCl pH 8.5) and stored at −20° C.

Endotoxin-free maxi-prep DNA was prepared from a 500 ml culture of the sequence verified clone (pDEST12.2_sCSF3R-6HIS) using the EndoFree Plasmid Mega kit (Qiagen) according to the manufacturer's instructions. Purified plasmid DNA was resuspended in endotoxin free TE buffer at a final concentration of at least 3 μg/μl and stored at −20° C.

TABLE 3

| SCSF3R cloning and sequencing primers | |
|---|---|
| Primer | Sequence (5'-3') |
| SCSF3R-F1 | ATGGCAAGGCTGGGAAACTG (SEQ ID NO: 13) |
| SCSF3R-R1 | TTTAGTAGAGGCGGGGTTTCG (SEQ ID NO: 14) |

TABLE 3-continued

SCSF3R cloning and sequencing primers

| Primer | Sequence (5'-3') |
|---|---|
| SCSF3R-F1 nest | ACTTGGGCTGCCCTGATCATCC (SEQ ID NO: 15) |
| SCSF3R-R1 nest | TGGCCAGGCTGATCATGAACTC (SEQ ID NO: 16) |
| SCSF3R-EX1 | GAAACTGCAGCCTGACTTGGGCTGCCCTGATCA (SEQ ID NO: 17) |
| SCSF3R-EX2 | GAGGCGGGGTTTCGCCTTGCTGGCCAGGCTGATCAT GAAC (SEQ ID NO: 18) |
| SCSF3R-EX3 | ATGGCAAGGCTGGGAAACTGCAGCCTGACTT (SEQ ID NO: 19) |
| SCSF3R-EX4 | ATTTTTTTGTATTTTTAGTAGAGGCGGGGTTTCGCC TT (SEQ ID NO: 20) |
| SCSF3R-EX5 | GCAGGCTTC<u>GCCACC</u>ATGGCAAGGCTGGGAAACTG (SEQ ID NO: 21) |
| SCSF3R-EX6 | *TGATGGTGATGGT*GATTTTTTTGTATTTTTAGTAGA GGC (SEQ ID NO: 22) |
| GCP Forward | GGGGACAAGTTTGTACAAAAAAGCAGGCTTC<u>GCCA CC</u> (SEQ ID NO: 23) |
| GCP Reverse | GGGGACCACTTTGTACAAGAAAGCTGGGTTTCAA*TG GTGATGGTGATGGTG* (SEQ ID NO: 24) |
| pEAK12F | GCCAGCTTGGCACTTGATGT (SEQ ID NO: 25) |
| pEAK12R | GATGGAGGTGGACGTGTCAG (SEQ ID NO: 26) |
| 21M13 | TGTAAAACGACGGCCAGT (SEQ ID NO: 27) |
| M13REV | CAGGAAACAGCTATGACC (SEQ ID NO: 28) |
| T7 | TAATACGACTCACTATAGG (SEQ ID NO: 29) |
| T3 | ATTAACCCTCACTAAAGG (SEQ ID NO: 30) |

Underlined sequence = Kozak sequence
Bold= Stop codon
*Italic sequence* = His tag

Example 2

Functional Genomics Expression in Mammalian Cells and Purification of the Cloned, His-Tagged Plasmid pEAK12d_sCSF3R-6HIS Human Embryonic Kidney 293 cells expressing the Epstein-Barr virus Nuclear Antigen (HEK293-EBNA, Invitrogen) were maintained in suspension in Ex-cell VPRO serum-free medium (seed stock, maintenance medium, JRH). Cells are inoculated at $1 \times 10^6$ cells/ml in 250 ml FEME (DMEM/Ham's F-12 1:1 19 mM HEPES, 5 g/L Glucose, 7.5 mM L-Glutamine, 4 ml/L ITS-X) (all Invitrogen-Life Technologies) medium supplemented with 1% FCS. For the transfection-mix 500 μg DNA (pEAK12d_sCSF3R-6HIS) plus 10 μg reporter-gene DNA is diluted in 50 ml FEME 1% FCS. Then 1 ml PEI (1 mg/l Polysciences, USA) is added. This mix is incubated for 10 minutes at room temperature. After 10 minutes the transfection mix is added to the cells and the culture is incubated at 37° C. in the incubator for 90 min. Finally the volume is topped up with the remaining 200 ml FEME 1% FCS containing 2.5 ml Pen-Strep to prevent contamination due to non-sterility of DNA. Confirmation of positive transfection was done by qualitative fluorescence examination at day 6 (Axiovert 10 Zeiss). On day 6 (harvest day), supernatant (500 ml) was centrifuged (4° C., 400 g) and placed into a pot bearing a unique identifier.

One aliquot (500 μl) was kept for QC of the 6His-tagged protein (internal bioprocessing QC).

Purification Process

The 500 ml culture medium sample containing the recombinant protein with a C-terminal 6His tag was diluted with one volume cold buffer A (50 mM $NaH_2PO_4$; 600 mM NaCl; 8.7% (w/v) glycerol, pH 7.5) to a final volume of 1000 ml. The sample was filtered through a 0.22 μm sterile filter (Millipore, 500 ml filter unit) and kept at 4° C. in a 1 liter sterile square media bottle (Nalgene).

The purification was performed at 4° C. on a VISION workstation (Applied Biosystems) connected to an automatic sample loader (Labomatic). The purification procedure was composed of two sequential steps, metal affinity chromatography on a Poros 20 MC (Applied Biosystems) column charged with Ni ions (10×50 mm, 3.93 ml), followed by buffer exchange on a Sephadex G-25 medium (Amersham Pharmacia) gel filtration column (1.0×15 cm).

For the first chromatography step the metal affinity column was regenerated with 30 column volumes of EDTA solution (100 mM EDTA; 1 M NaCl; pH 8.0), recharged with Ni ions through washing with 15 column volumes of a 100 mM $NiSO_4$ solution, washed with 10 column volumes of buffer A, followed by 7 column volumes of buffer B (50 mM $NaH_2PO_4$; 600 mM NaCl; 8.7% (w/v) glycerol, 400 mM; imidazole, pH 7.5), and finally equilibrated with 15 column volumes of buffer A containing 15 mM imidazole. The sample was transferred, by the Labomatic sample loader, into a 200 ml sample loop and subsequently charged onto the Ni metal affinity column at a flow rate of 20 ml/min. The charging procedure was repeated 5 times in order to transfer the entire sample (1000 ml) onto the Ni column. Subsequently the column was washed with 12 column volumes of buffer A, followed by 28 column volumes of buffer A containing 20 mM imidazole. During the 20 mM imidazole wash loosely attached contaminating proteins were eluted of the column. The recombinant His-tagged protein was finally eluted with 10 column volumes of buffer B at a flow rate of 2 ml/min, and the eluted protein was collected in a 2.7 ml fraction.

For the second chromatography step, the Sephadex G-25 gel-filtration column was regenerated with 2 ml of buffer D (1.137 M NaCl; 2.7 mM KCl; 1.5 mM $KH_2PO_4$; 8 mM $Na_2HPO_4$; pH 7.2), and subsequently equilibrated with 4 column volumes of buffer C (137 mM NaCl; 2.7 mM KCl; 1.5 mM $KH_2PO_4$; 8 mM $Na_2HPO_4$; 20% (w/v) glycerol; pH 7.4). The peak fraction eluted from the Ni-column was automatically, through the integrated sample loader on the VISION, loaded onto the Sephadex G-25 column and the protein was eluted with buffer C at a flow rate of 2 ml/min. The desalted sample was recovered in a 2.7 ml fraction. The fraction was filtered through a 0.22 μm sterile centrifugation filter (Millipore), aliquoted, frozen and stored at −80° C. An aliquot of the sample was analyzed on SDS-PAGE (4-12% NuPAGE gel; Novex) by Coomassie blue staining and Western blot with anti-His antibodies.

Coomassie Blue Staining

The NuPAGE gel was stained in a 0.1% coomassie blue R250 staining solution (30% methanol, 10% acetic acid) at room temperature for 1 h and subsequently destained in 20% methanol, 7.5% acetic acid until the background was clear and the protein bands clearly visible.

Western Blot

Following the electrophoresis the proteins were electrotransferred from the gel to a nitrocellulose membrane at 290 mA for 1 hour at 4° C. The membrane was blocked with 5% milk powder in buffer E (137 mM NaCl; 2.7 mM KCl; 1.5 mM $KH_2PO_4$; 8 mM $Na_2HPO_4$; 0.1% Tween 20, pH 7.4) for 1 hour at room temperature, and subsequently incubated with a mixture of 2 rabbit polyclonal anti-His antibodies (G-18 and H-15, 0.2 ug/ml each; Santa Cruz) in 2.5% milk powder in buffer E overnight at 4° C. After further 1 hour incubation at room temperature, the membrane was washed with buffer E (3×10 min), and then incubated with a secondary HRP-conjugated anti-rabbit antibody (DAKO, HRP 0399) diluted 1/3000 in buffer E containing 2.5% milk powder for 2 hours at room temperature. After washing with buffer E (3×10 minutes), the membrane was developed with the ECL kit (Amersham) for 1 min. The membrane was subsequently exposed to a Hyperfilm (Amersham), the film developed and the Western blot image visually analyzed.

Protein Assay

The protein concentration was determined using the BCA protein assay kit (Pierce) with bovine serum albumin as standard. The yield was 184 μg purified sCSF3R-6HIS.

The invention claimed is:

1. An isolated soluble colony stimulating factor 3 receptor (CSF3R) polypeptide variant, wherein said polypeptide variant comprises a ligand-binding domain, lacks a functional transmembrane domain and lacks a cytoplasmic domain, wherein said polypeptide variant further includes after the ligand-binding domain, amino acid residues 97-165 of SEQ ID NO: 4, or a fragment of amino acid residues 97-165 of SEQ ID NO: 4 that is at least 50 amino acids in length and wherein said polypeptide variant retains the ability to bind CSF3R natural ligands.

2. The isolated soluble CSF3R polypeptide variant of claim 1, wherein said ligand-binding domain is an immunoglobulin-like domain of CSF3R.

3. The isolated soluble CSF3R polypeptide variant of claim 2, wherein said immunoglobulin-like domain consists of amino acids 25 to 120 of SEQ ID NO: 10 or consists of amino acids 25 to 117 of SEQ ID NO: 10.

4. The isolated soluble CSF3R polypeptide variant of claim 1, which is selected from SEQ ID NO: 2, a mature form of SEQ ID NO: 2, a glycosylated form of SEQ ID NO: 2 or a polypeptide that has at least greater than 85% identity with SEQ ID NO: 2 and binds to CSF3R natural ligands.

5. The isolated soluble CSF3R polypeptide variant of claim 4, wherein said mature form is SEQ ID NO: 4.

6. The isolated soluble CSF3R polypeptide variant of claim 1, which is selected from SEQ ID NO: 6, a mature form of SEQ ID NO: 6, a glycosylated form of SEQ ID NO: 6 or a polypeptide that has at least 85% identity with SEQ ID NO: 6 and binds to CSF3R natural ligands.

7. The isolated CSF3R polypeptide variant of claim 6, wherein said mature form is SEQ ID NO: 8.

8. The isolated soluble CSF3R polypeptide variant of claim 1, characterized in that said variant is a naturally occurring soluble variant.

9. The isolated soluble CSF3R polypeptide variant of claim 1, wherein said polypeptide variant is selected from a mature form thereof, a glycosylated form thereof or a polypeptide that has at least 85% identity with SEQ ID NO: 4 and binds to CSF3R natural ligands.

10. The isolated soluble CSF3R polypeptide variant of claim 1, wherein said polypeptide variant is operably linked to an additional amino acid domain.

11. The isolated soluble CSF3R polypeptide variant of claim 10, wherein said additional amino acid domain comprises a signal peptide, a tag, a targeting peptide, the constant domain of an immunoglobulin, a multimerization domain or a biologically active protein or fragment thereof.

12. A composition comprising a pharmaceutically acceptable excipient and a CSF3R polypeptide variant according to claim 1.

* * * * *

UNITED STATES PATENT AND TRADEMARK OFFICE
CERTIFICATE OF CORRECTION

| | | |
|---|---|---|
| PATENT NO. | : 7,871,979 B2 | |
| APPLICATION NO. | : 12/304427 | |
| DATED | : January 18, 2011 | |
| INVENTOR(S) | : Melanie Yorke-Smith and Andreas Pigni | |

It is certified that error appears in the above-identified patent and that said Letters Patent is hereby corrected as shown below:

Column 1,
Line 31, "or CD7 114" should read --or CD114--.

Column 3,
Line 60, "product" should read --product.--.

Column 4,
Line 44, "coming form the" should read --coming from the--.

Column 7,
Line 36, "Ig like" should read --Ig-like--.

Column 19,
Line 55, "below" should read --below.--.

Column 20,
Line 46, "derived form" should read --derived from--.

Column 24,
Line 41, "IFN-7" should read --IFN-γ--.
Line 65, "proteinuria" should read --proteinuria.--.

Column 26,
Line 41, "believed to some" should read --believed to have some--.

Column 28,
Lines 17-18, "Keams-Sayre" should read --Kearns-Sayre--.

Signed and Sealed this
Twenty-fourth Day of May, 2011

David J. Kappos
*Director of the United States Patent and Trademark Office*

Column 29,
Line 25, "repeated disorder," should read --repeat disorder,--.

Column 31,
Line 10, "Gln$^{87}$." should read --Gln$^{87}$,--.

Column 34,
Line 28, "complimentarily" should read --complementarity--.

Column 37,
Line 53, "an Fab an F(ab')$_2$" should read --an Fab, an F(ab')$_2$--.

Column 38,
Line 18, "sCSF3Rpolypeptide" should read --sCSF3R polypeptide--.

UNITED STATES PATENT AND TRADEMARK OFFICE
CERTIFICATE OF CORRECTION

| | | |
|---|---|---|
| PATENT NO. | : 7,871,979 B2 | |
| APPLICATION NO. | : 12/304427 | |
| DATED | : January 18, 2011 | |
| INVENTOR(S) | : Melanie Yorke-Smith and Andreas Pigni | |

It is certified that error appears in the above-identified patent and that said Letters Patent is hereby corrected as shown below:

Column 1,
Line 31, "or CD7 114" should read --or CD114--.

Column 3,
Line 60, "product" should read --product.--.

Column 4,
Line 44, "coming form the" should read --coming from the--.

Column 7,
Line 36, "Ig like" should read --Ig-like--.

Column 19,
Line 55, "below" should read --below.--.

Column 20,
Line 46, "derived form" should read --derived from--.

Column 24,
Line 41, "IFN-7" should read --IFN-γ--.
Line 65, "proteinuria" should read --proteinuria.--.

Column 26,
Line 41, "believed to some" should read --believed to have some--.

Column 28,
Lines 17-18, "Keams-Sayre" should read --Kearns-Sayre--.

This certificate supersedes the Certificate of Correction issued May 24, 2011.

Signed and Sealed this
Twenty-eighth Day of June, 2011

David J. Kappos
*Director of the United States Patent and Trademark Office*

Column 29,
Line 25, "repeated disorder," should read --repeat disorder,--.

Column 31,
Line 10, "Gln$^{87}$." should read --Gln$^{87}$,--.

Column 34,
Line 28, "complimentarily" should read --complementarity--.

Column 37,
Line 53, "an Fab an F(ab')$_2$" should read --an Fab, an F(ab')$_2$--.

Column 38,
Line 18, "sCSF3Rpolypeptide" should read --sCSF3R polypeptide--.

Column 39,
Line 4, "may superior" should read --may be superior--.

Column 47,
Line 31, "the approximately the expected" should read --the approximately expected--.
Line 58, "AmpliTaq" should read --AmpliTaq™--.

Column 48,
Line 60, "(500±32=" should read --(500 + 32 =--.

Column 49,
Line 37, "(567±70=" should read --(567 + 70 =--.

```
                          SEQUENCE LISTING

<160> NUMBER OF SEQ ID NOS: 32

<210> SEQ ID NO 1
<211> LENGTH: 588
<212> TYPE: DNA
<213> ORGANISM: homo sapiens

<400> SEQUENCE: 1
atggcaaggc tgggaaactg cagcctgact tgggctgccc tgatcatcct gctgctcccc        60
ggaagtctgg aggagtgcgg gcacatcagt gtctcagccc ccatcgtcca cctgggggat       120
cccatcacag cctcctgcat catcaagcag aactgcagcc atctggaccc ggagccacag       180
attctgtgga gactgggagc agagcttcag cccggggggca ggcagcagcg tctgtctgat       240
gggacccagg aatctatcat caccctgccc cacctcaacc acactcaggc ctttctctcc       300
tgctgcctga actggggcaa cagcctgcag atcctggacc aggttgagct gcgcgcaggc       360
tgtaagtcct tccagccatc caactactct gcctccaaca ccctcctgcc aatactaata       420
agaatattac cagccgggca cgttggctca cgcctgtatt cccagcactt tgggaggccg       480
aggcaggcgg atcacctgag gtcaggagtt catgatcagc ctggccagca aggcgaaacc       540
ccgcctctac taaaaataca aaaaaatcac catcaccatc accattag                    588

<210> SEQ ID NO 2
<211> LENGTH: 189
<212> TYPE: PRT
<213> ORGANISM: homo sapiens

<400> SEQUENCE: 2

Met Ala Arg Leu Gly Asn Cys Ser Leu Thr Trp Ala Ala Leu Ile Ile
1               5                   10                  15

Leu Leu Leu Pro Gly Ser Leu Glu Glu Cys Gly His Ile Ser Val Ser
                20                  25                  30

Ala Pro Ile Val His Leu Gly Asp Pro Ile Thr Ala Ser Cys Ile Ile
            35                  40                  45

Lys Gln Asn Cys Ser His Leu Asp Pro Glu Pro Gln Ile Leu Trp Arg
        50                  55                  60

Leu Gly Ala Glu Leu Gln Pro Gly Gly Arg Gln Gln Arg Leu Ser Asp
65                  70                  75                  80

Gly Thr Gln Glu Ser Ile Ile Thr Leu Pro His Leu Asn His Thr Gln
                85                  90                  95

Ala Phe Leu Ser Cys Cys Leu Asn Trp Gly Asn Ser Leu Gln Ile Leu
            100                 105                 110

Asp Gln Val Glu Leu Arg Ala Gly Cys Lys Ser Phe Gln Pro Ser Asn
        115                 120                 125
```

```
Tyr Ser Ala Ser Asn Thr Leu Leu Pro Ile Leu Ile Arg Ile Leu Pro
    130                 135                 140

Ala Gly His Val Gly Ser Arg Leu Tyr Ser Gln His Phe Gly Arg Pro
145                 150                 155                 160

Arg Gln Ala Asp His Leu Arg Ser Gly Val His Asp Gln Pro Gly Gln
                165                 170                 175

Gln Gly Glu Thr Pro Pro Leu Leu Lys Ile Gln Lys Asn
            180                 185

<210> SEQ ID NO 3
<211> LENGTH: 513
<212> TYPE: DNA
<213> ORGANISM: homo sapiens

<400> SEQUENCE: 3
gagtgcgggc acatcagtgt ctcagccccc atcgtccacc tggggatcc catcacagcc      60 tcctgcatca tcaagcagaa ctgcagccat ctggacccgg agccacagat tctgtggaga     120 ctggagcag agcttcagcc gggggcagg cagcagcgtc tgtctgatgg gacccaggaa       180
tctatcatca ccctgcccca cctcaaccac actcaggcct ttctctcctg ctgcctgaac     240 tgggcaaca gcctgcagat cctggaccag gttgagctgc gcgcaggctg taagtccttc      300
cagccatcca actactctgc ctccaacacc ctcctgccaa tactaataag aatattacca    360
gccgggcacg ttggctcacg cctgtattcc cagcactttg ggaggccgag gcaggcggat     420
cacctgaggt caggagttca tgatcagcct ggccagcaag gcgaaacccc gcctctacta    480
aaaatacaaa aaaatcacca tcaccatcac cat                                 513

<210> SEQ ID NO 4
<211> LENGTH: 165
<212> TYPE: PRT
<213> ORGANISM: homo sapiens

<400> SEQUENCE: 4

Glu Cys Gly His Ile Ser Val Ser Ala Pro Ile Val His Leu Gly Asp
1               5                   10                  15

Pro Ile Thr Ala Ser Cys Ile Ile Lys Gln Asn Cys Ser His Leu Asp
            20                  25                  30

Pro Glu Pro Gln Ile Leu Trp Arg Leu Gly Ala Glu Leu Gln Pro Gly
        35                  40                  45

Gly Arg Gln Gln Arg Leu Ser Asp Gly Thr Gln Glu Ser Ile Ile Thr
    50                  55                  60

Leu Pro His Leu Asn His Thr Gln Ala Phe Leu Ser Cys Cys Leu Asn
65                  70                  75                  80

Trp Gly Asn Ser Leu Gln Ile Leu Asp Gln Val Glu Leu Arg Ala Gly
                85                  90                  95

Cys Lys Ser Phe Gln Pro Ser Asn Tyr Ser Ala Ser Asn Thr Leu Leu
            100                 105                 110

Pro Ile Leu Ile Arg Ile Leu Pro Ala Gly His Val Gly Ser Arg Leu
        115                 120                 125

Tyr Ser Gln His Phe Gly Arg Pro Arg Gln Ala Asp His Leu Arg Ser
    130                 135                 140

Gly Val His Asp Gln Pro Gly Gln Gln Gly Glu Thr Pro Pro Leu Leu
145                 150                 155                 160

Lys Ile Gln Lys Asn
                165
```

<210> SEQ ID NO 5
<211> LENGTH: 501
<212> TYPE: DNA
<213> ORGANISM: homo sapiens

<400> SEQUENCE: 5

```
acttgggctg ccctgatcat cctgctgctc cccggaagtc tggaggagtg cgggcacatc      60
agtgtctcag cccccatcgt ccacctgggg gatcccatca cagcctcctg catcatcaag     120
cagaactgca gccatctgga cccggagcca cagattctgt ggagactggg agcagagctt     180
cagcccgggg gcaggcagca gcgtctgtct gatgggaccc aggaatctat catcaccctg     240
ccccacctca accacactca ggcctttctc tcctgctgcc tgaactgggg caacagcctg     300
cagatcctgg accaggttga gctgcgcgca ggctgtaagt ccttccagcc atccaactac     360
tctgcctcca cacccctcct gccaatacta ataagaatat taccagccgg gcacgttggc     420
tcacgcctgt attcccagca ctttgggagg ccgaggcagg cggatcacct gaggtcagga     480
gttcatgatc agcctggcca g                                               501
```

<210> SEQ ID NO 6
<211> LENGTH: 167
<212> TYPE: PRT
<213> ORGANISM: homo sapiens

<400> SEQUENCE: 6

```
Thr Trp Ala Ala Leu Ile Ile Leu Leu Pro Gly Ser Leu Glu Glu
1               5                   10                  15

Cys Gly His Ile Ser Val Ser Ala Pro Ile Val His Leu Gly Asp Pro
                20                  25                  30

Ile Thr Ala Ser Cys Ile Ile Lys Gln Asn Cys Ser His Leu Asp Pro
            35                  40                  45

Glu Pro Gln Ile Leu Trp Arg Leu Gly Ala Glu Leu Gln Pro Gly Gly
        50                  55                  60

Arg Gln Gln Arg Leu Ser Asp Gly Thr Gln Glu Ser Ile Ile Thr Leu
65                  70                  75                  80

Pro His Leu Asn His Thr Gln Ala Phe Leu Ser Cys Cys Leu Asn Trp
                85                  90                  95

Gly Asn Ser Leu Gln Ile Leu Asp Gln Val Glu Leu Arg Ala Gly Cys
                100                 105                 110

Lys Ser Phe Gln Pro Ser Asn Tyr Ser Ala Ser Asn Thr Leu Leu Pro
            115                 120                 125

Ile Leu Ile Arg Ile Leu Pro Ala Gly His Val Gly Ser Arg Leu Tyr
        130                 135                 140

Ser Gln His Phe Gly Arg Pro Arg Gln Ala Asp His Leu Arg Ser Gly
145                 150                 155                 160

Val His Asp Gln Pro Gly Gln
                165
```

<210> SEQ ID NO 7
<211> LENGTH: 456
<212> TYPE: DNA
<213> ORGANISM: homo sapiens

<400> SEQUENCE: 7

```
gagtgcgggc acatcagtgt ctcagccccc atcgtccacc tggggatcc catcacagcc       60
tcctgcatca tcaagcagaa ctgcagccat ctggacccgg agccacagat tctgtggaga     120
```

| | |
|---|---|
| ctgggagcag agcttcagcc cggggcagg cagcagcgtc tgtctgatgg gacccaggaa | 180 |
| tctatcatca ccctgcccca cctcaaccac actcaggcct ttctctcctg ctgcctgaac | 240 |
| tgggcaaca gcctgcagat cctggaccag gttgagctgc gcgcaggctg taagtccttc | 300 |
| cagccatcca actactctgc ctccaacacc ctcctgccaa tactaataag aatattacca | 360 |
| gccgggcacg ttggctcacg cctgtattcc cagcactttg ggaggccgag gcaggcggat | 420 |
| cacctgaggt caggagttca tgatcagcct ggccag | 456 |

<210> SEQ ID NO 8
<211> LENGTH: 152
<212> TYPE: PRT
<213> ORGANISM: homo sapiens

<400> SEQUENCE: 8

Glu Cys Gly His Ile Ser Val Ser Ala Pro Ile Val His Leu Gly Asp
1               5                   10                  15

Pro Ile Thr Ala Ser Cys Ile Ile Lys Gln Asn Cys Ser His Leu Asp
            20                  25                  30

Pro Glu Pro Gln Ile Leu Trp Arg Leu Gly Ala Glu Leu Gln Pro Gly
        35                  40                  45

Gly Arg Gln Gln Arg Leu Ser Asp Gly Thr Gln Glu Ser Ile Ile Thr
    50                  55                  60

Leu Pro His Leu Asn His Thr Gln Ala Phe Leu Ser Cys Cys Leu Asn
65                  70                  75                  80

Trp Gly Asn Ser Leu Gln Ile Leu Asp Gln Val Glu Leu Arg Ala Gly
                85                  90                  95

Cys Lys Ser Phe Gln Pro Ser Asn Tyr Ser Ala Ser Asn Thr Leu Leu
            100                 105                 110

Pro Ile Leu Ile Arg Ile Leu Pro Ala Gly His Val Gly Ser Arg Leu
        115                 120                 125

Tyr Ser Gln His Phe Gly Arg Pro Arg Gln Ala Asp His Leu Arg Ser
    130                 135                 140

Gly Val His Asp Gln Pro Gly Gln
145                 150

<210> SEQ ID NO 9
<211> LENGTH: 2933
<212> TYPE: DNA
<213> ORGANISM: homo sapiens

<400> SEQUENCE: 9

| | |
|---|---|
| ctggactgca gctggtttca ggaacttctc ttgacgagaa gagagaccaa ggaggccaag | 60 |
| caggggctgg gccagaggtg ccaacatggg gaaactgagg ctcggctcgg aaaggtgaag | 120 |
| taacttgtcc aagatcacaa agctggtgaa catcaagttg gtgctatggc aaggctggga | 180 |
| aactgcagcc tgacttgggc tgccctgatc atcctgctgc tccccggaag tctggaggag | 240 |
| tgcgggcaca tcagtgtctc agcccccatc gtccacctgg ggatcccat acagcctcc | 300 |
| tgcatcatca agcagaactg cagccatctg gacccggagc cacagattct gtggagactg | 360 |
| ggagcagagc ttcagcccgg ggcaggcag cagcgtctgt ctgatgggac ccaggaatct | 420 |
| atcatcaccc tgccccacct caaccacact caggcctttc tcctgctgc ctgaactgg | 480 |
| ggcaacagcc tgcagatcct ggaccaggtt gagctgcgcg caggctaccc tccagccata | 540 |
| ccccacaacc tctcctgcct catgaacctc acaaccagca gcctcatctg ccagtgggag | 600 |

| | |
|---|---|
| ccaggacctg agacccacct acccaccagc ttcactctga agagtttcaa gagccggggc | 660 |
| aactgtcaga cccaagggga ctccatcctg gactgcgtgc ccaaggacgg gcagagccac | 720 |
| tgctgcatcc cacgcaaaca cctgctgttg taccagaata tgggcatctg ggtgcaggca | 780 |
| gagaatgcgc tggggaccag catgtcccca caactgtgtc ttgatcccat ggatgttgtg | 840 |
| aaactggagc cccccatgct gcggaccatg gaccccagcc ctgaagcggc ccctccccag | 900 |
| gcaggctgcc tacagctgtg ctgggagcca tggcagccag gcctgcacat aaatcagaag | 960 |
| tgtgagctgc gccacaagcc gcagcgtgga gaagccagct gggcactggt gggcccctc | 1020 |
| cccttggagg cccttcagta tgagctctgc gggctcctcc cagccacggc ctacaccctg | 1080 |
| cagatacgct gcatccgctg gccctgcct ggccactgga gcgactggag ccccagcctg | 1140 |
| gagctgagaa ctaccgaacg gcccccact gtcagactgg acacatggtg gcggcagagg | 1200 |
| cagctggacc ccaggacagt gcagctgttc tggaagccag tgccctggga ggaagacagc | 1260 |
| ggacggatcc aaggttatgt ggtttcttgg agaccctcag gccaggctgg ggccatcctg | 1320 |
| cccctctgca acaccacaga gctcagctgc accttccacc tgccttcaga agcccaggag | 1380 |
| gtggcccttg tggcctataa ctcagccggg acctctcgcc ccaccccggt ggtcttctca | 1440 |
| gaaagcagag gcccagctct gaccagactc catgccatgg cccgagaccc tcacagcctc | 1500 |
| tgggtaggct gggagccccc caatccatgg cctcagggct atgtgattga gtggggcctg | 1560 |
| ggcccccca gcgcgagcaa tagcaacaag acctggagga tggaacagaa tgggagagcc | 1620 |
| acggggtttc tgctgaagga gaacatcagg cccttcagc tctatgagat catcgtgact | 1680 |
| cccttgtacc aggacaccat gggaccctcc cagcatgtct atgcctactc tcaagaaatg | 1740 |
| gctccctccc atgccccaga gctgcatcta aagcacattg gcaagacctg gcacagctg | 1800 |
| gagtgggtgc ctgagccccc tgagctgggg aagagccccc ttacccacta ccatcatcttc | 1860 |
| tggaccaacg ctcagaacca gtccttctcc gccatcctga atgcctcctc ccgtggcttt | 1920 |
| gtcctccatg gcctggagcc cgccagtctg tatcacatcc acctcatggc tgccagccag | 1980 |
| gctggggcca ccaacagtac agtcctcacc ctgatgacct tgaccccaga ggggtcggag | 2040 |
| ctacacatca tcctgggcct gttcggcctc ctgctgttgc tcacctgcct ctgtggaact | 2100 |
| gcctggctct gttgcagccc caacaggaag aatcccctct ggccaagtgt cccagaccca | 2160 |
| gctcacagca gcctgggctc ctgggtgccc acaatcatgg aggaggatgc cttccagctg | 2220 |
| cccggccttg gcacgccacc catcaccaag ctcacagtgc tggaggagga tgaaaagaag | 2280 |
| ccggtgccct gggagtccca taacagctca gagacctgtg gcctcccac tctggtccag | 2340 |
| acctatgtgc tccaggggga cccaagagca gtttccaccc agcccaatc ccagtctggc | 2400 |
| accagcgatc aggtccttta tgggcagctg ctgggcagcc cacaagccc agggccaggg | 2460 |
| cactatctcc gctgtgactc cactcagccc ctcttggcgg gcctcacccc cagcccaag | 2520 |
| tcctatgaga acctctggtt ccaggccagc cccttgggga ccctggtaac ccagccccca | 2580 |
| agccaggagg acgactgtgt ctttgggcca ctgctcaact tccccctcct gcagggatc | 2640 |
| cgggtccatg ggatggaggc gctggggagc ttctagggct tcctgggggtt cccttcttgg | 2700 |
| gcctgccttt taaggcctg agctagctgg agaagagggg agggtccata agcccatgac | 2760 |
| taaaaactac cccagcccag gctctcacca tctccagtca ccagcatctc cctctcctcc | 2820 |
| caatctccat aggctgggcc tcccaggcga tctgcatact ttaaggacca gatcatgctc | 2880 |
| catccagccc cacccaatgg cctttgtgc ttgtttccta taacttcagt att | 2933 |

<210> SEQ ID NO 10
<211> LENGTH: 836
<212> TYPE: PRT
<213> ORGANISM: homo sapiens

<400> SEQUENCE: 10

Met Ala Arg Leu Gly Asn Cys Ser Leu Thr Trp Ala Ala Leu Ile Ile
1               5                   10                  15
Leu Leu Leu Pro Gly Ser Leu Glu Glu Cys Gly His Ile Ser Val Ser
                20                  25                  30
Ala Pro Ile Val His Leu Gly Asp Pro Ile Thr Ala Ser Cys Ile Ile
            35                  40                  45
Lys Gln Asn Cys Ser His Leu Asp Pro Glu Pro Gln Ile Leu Trp Arg
    50                  55                  60
Leu Gly Ala Glu Leu Gln Pro Gly Gly Arg Gln Arg Leu Ser Asp
65                  70                  75                  80
Gly Thr Gln Glu Ser Ile Ile Thr Leu Pro His Leu Asn His Thr Gln
                85                  90                  95
Ala Phe Leu Ser Cys Cys Leu Asn Trp Gly Asn Ser Leu Gln Ile Leu
            100                 105                 110
Asp Gln Val Glu Leu Arg Ala Gly Tyr Pro Pro Ala Ile Pro His Asn
        115                 120                 125
Leu Ser Cys Leu Met Asn Leu Thr Thr Ser Ser Leu Ile Cys Gln Trp
130                 135                 140
Glu Pro Gly Pro Glu Thr His Leu Pro Thr Ser Phe Thr Leu Lys Ser
145                 150                 155                 160
Phe Lys Ser Arg Gly Asn Cys Gln Thr Gln Gly Asp Ser Ile Leu Asp
                165                 170                 175
Cys Val Pro Lys Asp Gly Gln Ser His Cys Cys Ile Pro Arg Lys His
            180                 185                 190
Leu Leu Leu Tyr Gln Asn Met Gly Ile Trp Val Gln Ala Glu Asn Ala
        195                 200                 205
Leu Gly Thr Ser Met Ser Pro Gln Leu Cys Leu Asp Pro Met Asp Val
    210                 215                 220
Val Lys Leu Glu Pro Pro Met Leu Arg Thr Met Asp Pro Ser Pro Glu
225                 230                 235                 240
Ala Ala Pro Pro Gln Ala Gly Cys Leu Gln Leu Cys Trp Glu Pro Trp
                245                 250                 255
Gln Pro Gly Leu His Ile Asn Gln Lys Cys Glu Leu Arg His Lys Pro
            260                 265                 270
Gln Arg Gly Glu Ala Ser Trp Ala Leu Val Gly Pro Leu Pro Leu Glu
        275                 280                 285
Ala Leu Gln Tyr Glu Leu Cys Gly Leu Leu Pro Ala Thr Ala Tyr Thr
    290                 295                 300
Leu Gln Ile Arg Cys Ile Arg Trp Pro Leu Pro Gly His Trp Ser Asp
305                 310                 315                 320
Trp Ser Pro Ser Leu Glu Leu Arg Thr Thr Glu Arg Ala Pro Thr Val
                325                 330                 335
Arg Leu Asp Thr Trp Trp Arg Gln Arg Gln Leu Asp Pro Arg Thr Val
            340                 345                 350
Gln Leu Phe Trp Lys Pro Val Pro Leu Glu Glu Asp Ser Gly Arg Ile
        355                 360                 365
Gln Gly Tyr Val Val Ser Trp Arg Pro Ser Gly Gln Ala Gly Ala Ile
    370                 375                 380

-continued

```
Leu Pro Leu Cys Asn Thr Thr Glu Leu Ser Cys Thr Phe His Leu Pro
385                 390                 395                 400

Ser Glu Ala Gln Glu Val Ala Leu Val Ala Tyr Asn Ser Ala Gly Thr
            405                 410                 415

Ser Arg Pro Thr Pro Val Val Phe Ser Glu Ser Arg Gly Pro Ala Leu
            420                 425                 430

Thr Arg Leu His Ala Met Ala Arg Asp Pro His Ser Leu Trp Val Gly
            435                 440                 445

Trp Glu Pro Pro Asn Pro Trp Pro Gln Gly Tyr Val Ile Glu Trp Gly
        450                 455                 460

Leu Gly Pro Pro Ser Ala Ser Asn Ser Asn Lys Thr Trp Arg Met Glu
465                 470                 475                 480

Gln Asn Gly Arg Ala Thr Gly Phe Leu Leu Lys Glu Asn Ile Arg Pro
                485                 490                 495

Phe Gln Leu Tyr Glu Ile Ile Val Thr Pro Leu Tyr Gln Asp Thr Met
                500                 505                 510

Gly Pro Ser Gln His Val Tyr Ala Tyr Ser Gln Glu Met Ala Pro Ser
            515                 520                 525

His Ala Pro Glu Leu His Leu Lys His Ile Gly Lys Thr Trp Ala Gln
530                 535                 540

Leu Glu Trp Val Pro Glu Pro Pro Glu Leu Gly Lys Ser Pro Leu Thr
545                 550                 555                 560

His Tyr Thr Ile Phe Trp Thr Asn Ala Gln Asn Gln Ser Phe Ser Ala
                565                 570                 575

Ile Leu Asn Ala Ser Ser Arg Gly Phe Val Leu His Gly Leu Glu Pro
                580                 585                 590

Ala Ser Leu Tyr His Ile His Leu Met Ala Ala Ser Gln Ala Gly Ala
            595                 600                 605

Thr Asn Ser Thr Val Leu Thr Leu Met Thr Leu Thr Pro Glu Gly Ser
610                 615                 620

Glu Leu His Ile Ile Leu Gly Leu Phe Gly Leu Leu Leu Leu Leu Thr
625                 630                 635                 640

Cys Leu Cys Gly Thr Ala Trp Leu Cys Cys Ser Pro Asn Arg Lys Asn
                645                 650                 655

Pro Leu Trp Pro Ser Val Pro Asp Pro Ala His Ser Ser Leu Gly Ser
                660                 665                 670

Trp Val Pro Thr Ile Met Glu Glu Asp Ala Phe Gln Leu Pro Gly Leu
        675                 680                 685

Gly Thr Pro Pro Ile Thr Lys Leu Thr Val Leu Glu Glu Asp Glu Lys
        690                 695                 700

Lys Pro Val Pro Trp Glu Ser His Asn Ser Ser Glu Thr Cys Gly Leu
705                 710                 715                 720

Pro Thr Leu Val Gln Thr Tyr Val Leu Gln Gly Asp Pro Arg Ala Val
                725                 730                 735

Ser Thr Gln Pro Gln Ser Gln Ser Gly Thr Ser Asp Gln Val Leu Tyr
            740                 745                 750

Gly Gln Leu Leu Gly Ser Pro Thr Ser Pro Gly Pro Gly His Tyr Leu
            755                 760                 765

Arg Cys Asp Ser Thr Gln Pro Leu Leu Ala Gly Leu Thr Pro Ser Pro
770                 775                 780

Lys Ser Tyr Glu Asn Leu Trp Phe Gln Ala Ser Pro Leu Gly Thr Leu
785                 790                 795                 800

Val Thr Pro Ala Pro Ser Gln Glu Asp Asp Cys Val Phe Gly Pro Leu
```

```
                    805                 810                 815
Leu Asn Phe Pro Leu Leu Gln Gly Ile Arg Val His Gly Met Glu Ala
        820                 825                 830

Leu Gly Ser Phe
        835

<210> SEQ ID NO 11
<211> LENGTH: 288
<212> TYPE: DNA
<213> ORGANISM: homo sapiens

<400> SEQUENCE: 11
gagtgcgggc acatcagtgt ctcagccccc atcgtccacc tgggggatcc catcacagcc      60
tcctgcatca tcaagcagaa ctgcagccat ctggacccgg agccacagat tctgtgagag     120
ctgggagcag agcttcagcc cgggggcagg cagcagcgtc tgtctgatgg gacccaggaa     180
tctatcatca ccctgcccca cctcaaccac actcaggcct ttctctcctg ctgcctgaac     240
tggggcaaca gcctgcagat cctggaccag gttgagctgc gcgcaggc                  288

<210> SEQ ID NO 12
<211> LENGTH: 96
<212> TYPE: PRT
<213> ORGANISM: homo sapiens

<400> SEQUENCE: 12

Glu Cys Gly His Ile Ser Val Ser Ala Pro Ile Val His Leu Gly Asp
1               5                   10                  15

Pro Ile Thr Ala Ser Cys Ile Ile Lys Gln Asn Cys Ser His Leu Asp
            20                  25                  30

Pro Glu Pro Gln Ile Leu Trp Arg Leu Gly Ala Glu Leu Gln Pro Gly
        35                  40                  45

Gly Arg Gln Gln Arg Leu Ser Asp Gly Thr Gln Glu Ser Ile Ile Thr
    50                  55                  60

Leu Pro His Leu Asn His Thr Gln Ala Phe Leu Ser Cys Cys Leu Asn
65                  70                  75                  80

Trp Gly Asn Ser Leu Gln Ile Leu Asp Gln Val Glu Leu Arg Ala Gly
                85                  90                  95

<210> SEQ ID NO 13
<211> LENGTH: 20
<212> TYPE: DNA
<213> ORGANISM: artificial
<220> FEATURE:
<223> OTHER INFORMATION: sCSF3R-F1 primer

<400> SEQUENCE: 13
atggcaaggc tgggaaactg                                                  20

<210> SEQ ID NO 14
<211> LENGTH: 21
<212> TYPE: DNA
<213> ORGANISM: artificial
<220> FEATURE:
<223> OTHER INFORMATION: sCSF3R-R1 primer

<400> SEQUENCE: 14
tttagtagag gcggggtttc g                                                21

<210> SEQ ID NO 15
<211> LENGTH: 22
```

<212> TYPE: DNA
<213> ORGANISM: artificial
<220> FEATURE:
<223> OTHER INFORMATION: sCSF3R-F1 nest primer

<400> SEQUENCE: 15
acttgggctg ccctgatcat cc                                            22

<210> SEQ ID NO 16
<211> LENGTH: 22
<212> TYPE: DNA
<213> ORGANISM: artificial
<220> FEATURE:
<223> OTHER INFORMATION: sCFS3R-R1 nest primer

<400> SEQUENCE: 16
tggccaggct gatcatgaac tc                                            22

<210> SEQ ID NO 17
<211> LENGTH: 33
<212> TYPE: DNA
<213> ORGANISM: artificial
<220> FEATURE:
<223> OTHER INFORMATION: sCFS3R-EX1 primer

<400> SEQUENCE: 17
gaaactgcag cctgacttgg gctgccctga tca                                33

<210> SEQ ID NO 18
<211> LENGTH: 40
<212> TYPE: DNA
<213> ORGANISM: artificial
<220> FEATURE:
<223> OTHER INFORMATION: sCSF3R-EX2 primer

<400> SEQUENCE: 18
gaggcggggt tcgccttgc tggccaggct gatcatgaac                           40

<210> SEQ ID NO 19
<211> LENGTH: 31
<212> TYPE: DNA
<213> ORGANISM: artificial
<220> FEATURE:
<223> OTHER INFORMATION: sCSF3R-EX3 primer

<400> SEQUENCE: 19
atggcaaggc tgggaaactg cagcctgact t                                  31

<210> SEQ ID NO 20
<211> LENGTH: 38
<212> TYPE: DNA
<213> ORGANISM: artificial
<220> FEATURE:
<223> OTHER INFORMATION: sCSF3R-EX4 primer

<400> SEQUENCE: 20
atttttttgt atttttagta gaggcggggt tcgccctt                           38

<210> SEQ ID NO 21
<211> LENGTH: 35
<212> TYPE: DNA
<213> ORGANISM: artificial
<220> FEATURE:
<223> OTHER INFORMATION: sCSF3R-EX5 primer

<400> SEQUENCE: 21

```
gcaggcttcg ccaccatggc aaggctggga aactg          35

<210> SEQ ID NO 22
<211> LENGTH: 39
<212> TYPE: DNA
<213> ORGANISM: artificial
<220> FEATURE:
<223> OTHER INFORMATION: sCSF3R-EX6 primer

<400> SEQUENCE: 22
tgatggtgat ggtgattttt ttgtattttt agtagaggc      39

<210> SEQ ID NO 23
<211> LENGTH: 37
<212> TYPE: DNA
<213> ORGANISM: artificial
<220> FEATURE:
<223> OTHER INFORMATION: GCP forward

<400> SEQUENCE: 23
ggggacaagt ttgtacaaaa aagcaggctt cgccacc        37

<210> SEQ ID NO 24
<211> LENGTH: 51
<212> TYPE: DNA
<213> ORGANISM: artificial
<220> FEATURE:
<223> OTHER INFORMATION: GCP Reverse

<400> SEQUENCE: 24
ggggaccact ttgtacaaga aagctgggtt tcaatggtga tggtgatggt g    51

<210> SEQ ID NO 25
<211> LENGTH: 20
<212> TYPE: DNA
<213> ORGANISM: artificial
<220> FEATURE:
<223> OTHER INFORMATION: pEAK12F

<400> SEQUENCE: 25
gccagcttgg cacttgatgt                           20

<210> SEQ ID NO 26
<211> LENGTH: 20
<212> TYPE: DNA
<213> ORGANISM: artificial
<220> FEATURE:
<223> OTHER INFORMATION: pEAK12R

<400> SEQUENCE: 26
gatggaggtg gacgtgtcag                           20

<210> SEQ ID NO 27
<211> LENGTH: 18
<212> TYPE: DNA
<213> ORGANISM: artificial
<220> FEATURE:
<223> OTHER INFORMATION: 21M13

<400> SEQUENCE: 27
tgtaaaacga cggccagt                             18

<210> SEQ ID NO 28
<211> LENGTH: 18
<212> TYPE: DNA
<213> ORGANISM: artificial
```

```
<220> FEATURE:
<223> OTHER INFORMATION: M13REV

<400> SEQUENCE: 28
caggaaacag ctatgacc                                                       18

<210> SEQ ID NO 29
<211> LENGTH: 19
<212> TYPE: DNA
<213> ORGANISM: artificial
<220> FEATURE:
<223> OTHER INFORMATION: T7

<400> SEQUENCE: 29
taatacgact cactatagg                                                      19

<210> SEQ ID NO 30
<211> LENGTH: 18
<212> TYPE: DNA
<213> ORGANISM: artificial
<220> FEATURE:
<223> OTHER INFORMATION: T3

<400> SEQUENCE: 30
attaaccctc actaaagg                                                       18

<210> SEQ ID NO 31
<211> LENGTH: 599
<212> TYPE: DNA
<213> ORGANISM: Homo sapiens
<220> FEATURE:
<221> NAME/KEY: exon
<222> LOCATION: (21)..(587)

<400> SEQUENCE: 31
gtgaacatca agttggtgct atg gca agg ctg gga aac tgc agc ctg act tgg        53
                     Met Ala Arg Leu Gly Asn Cys Ser Leu Thr Trp
                       1               5                  10 gct gcc ctg atc atc ctg ctg ctc ccc gga agt ctg gag gag tgc ggg         101
Ala Ala Leu Ile Ile Leu Leu Leu Pro Gly Ser Leu Glu Glu Cys Gly
            15                  20                  25 cac atc agt gtc tca gcc ccc atc gtc cac ctg ggg gat ccc atc aca         149
His Ile Ser Val Ser Ala Pro Ile Val His Leu Gly Asp Pro Ile Thr
        30                  35                  40 gcc tcc tgc atc atc aag cag aac tgc agc cat ctg gac ccg gag cca         197
Ala Ser Cys Ile Ile Lys Gln Asn Cys Ser His Leu Asp Pro Glu Pro
    45                  50                  55 cag att ctg tgg aga ctg gga gca gag ctt cag ccc ggg ggc agg cag         245
Gln Ile Leu Trp Arg Leu Gly Ala Glu Leu Gln Pro Gly Gly Arg Gln
60                  65                  70                  75 cag cgt ctg tct gat ggg acc cag gaa tct atc atc acc ctg ccc cac         293
Gln Arg Leu Ser Asp Gly Thr Gln Glu Ser Ile Ile Thr Leu Pro His
                80                  85                  90 ctc aac cac act cag gcc ttt ctc tcc tgc tgc ctg aac tgg ggc aac         341
Leu Asn His Thr Gln Ala Phe Leu Ser Cys Cys Leu Asn Trp Gly Asn
            95                 100                 105 agc ctg cag atc ctg gac cag gtt gag ctg cgc gca ggc tgt aag tcc         389
Ser Leu Gln Ile Leu Asp Gln Val Glu Leu Arg Ala Gly Cys Lys Ser
        110                 115                 120 ttc cag cca tcc aac tac tct gcc tcc aac acc ctc ctg cca ata cta         437
Phe Gln Pro Ser Asn Tyr Ser Ala Ser Asn Thr Leu Leu Pro Ile Leu
    125                 130                 135 ata aga ata tta cca gcc ggg cac gtt ggc tca cgc ctg tat tcc cag         485
```

```
Ile Arg Ile Leu Pro Ala Gly His Val Gly Ser Arg Leu Tyr Ser Gln
140                 145                 150                 155 cac ttt ggg agg ccg agg cag gcg gat cac ctg agg tca gga gtt cat     533
His Phe Gly Arg Pro Arg Gln Ala Asp His Leu Arg Ser Gly Val His
                160                 165                 170 gat cag cct ggc cag caa ggc gaa acc ccg cct cta cta aaa ata caa     581
Asp Gln Pro Gly Gln Gln Gly Glu Thr Pro Pro Leu Leu Lys Ile Gln
                175                 180                 185 aaa aat tagccaggca ta                                               599
Lys Asn

<210> SEQ ID NO 32
<211> LENGTH: 500
<212> TYPE: DNA
<213> ORGANISM: Homo sapiens
<220> FEATURE:
<221> NAME/KEY: exon
<222> LOCATION: (1)..(500)

<400> SEQUENCE: 32 act tgg gct gcc ctg atc atc ctg ctc ccc gga agt ctg gag gag          48
Thr Trp Ala Ala Leu Ile Ile Leu Leu Pro Gly Ser Leu Glu Glu
1               5                   10                  15 tgc ggg cac atc agt gtc tca gcc ccc atc gtc cac ctg ggg gat ccc     96
Cys Gly His Ile Ser Val Ser Ala Pro Ile Val His Leu Gly Asp Pro
                20                  25                  30 atc aca gcc tcc tgc atc atc aag cag aac tgc agc cat ctg gac ccg    144
Ile Thr Ala Ser Cys Ile Ile Lys Gln Asn Cys Ser His Leu Asp Pro
            35                  40                  45 gag cca cag att ctg tgg aga ctg gga gca gag ctt cag ccc ggg ggc    192
Glu Pro Gln Ile Leu Trp Arg Leu Gly Ala Glu Leu Gln Pro Gly Gly
        50                  55                  60 agg cag cag cgt ctg tct gat ggg acc cag gaa tct atc atc acc ctg    240
Arg Gln Gln Arg Leu Ser Asp Gly Thr Gln Glu Ser Ile Ile Thr Leu
65                  70                  75                  80 ccc cac ctc aac cac act cag gcc ttt ctc tcc tgc tgc ctg aac tgg    288
Pro His Leu Asn His Thr Gln Ala Phe Leu Ser Cys Cys Leu Asn Trp
                85                  90                  95 ggc aac agc ctg cag atc ctg gac cag gtt gag ctg cgc gca ggc tgt    336
Gly Asn Ser Leu Gln Ile Leu Asp Gln Val Glu Leu Arg Ala Gly Cys
                100                 105                 110 aag tcc ttc cag cca tcc aac tac tct gcc tcc aac acc ctc ctg cca    384
Lys Ser Phe Gln Pro Ser Asn Tyr Ser Ala Ser Asn Thr Leu Leu Pro
            115                 120                 125 ata cta ata aga ata tta cca gcc ggg cac gtt ggc tca cgc ctg tat    432
Ile Leu Ile Arg Ile Leu Pro Ala Gly His Val Gly Ser Arg Leu Tyr
        130                 135                 140 tcc cag cac ttt ggg agg ccg agg cag gcg gat cac ctg agg tca gga    480
Ser Gln His Phe Gly Arg Pro Arg Gln Ala Asp His Leu Arg Ser Gly
145                 150                 155                 160 gtt cat gat cag cct ggc ca                                          500
Val His Asp Gln Pro Gly
                165
```